United States Patent
Tabuchi et al.

(10) Patent No.: US 9,068,212 B2
(45) Date of Patent: *Jun. 30, 2015

(54) METHOD FOR PRODUCING A POLYPEPTIDE USING A CELL THAT OVEREXPRESSES A BICARBONATE TRANSPORTER

(75) Inventors: Hisahiro Tabuchi, Tokyo (JP); Satoshi Tainaka, Tokyo (JP); Tomoya Sugiyama, Tokyo (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 12/734,283

(22) PCT Filed: Oct. 23, 2008

(86) PCT No.: PCT/JP2008/069184

§ 371 (c)(1),
(2), (4) Date: Apr. 22, 2010

(87) PCT Pub. No.: WO2009/054433

PCT Pub. Date: Apr. 30, 2009

(65) Prior Publication Data

US 2011/0014654 A1 Jan. 20, 2011

(30) Foreign Application Priority Data

Oct. 24, 2007 (JP) ................................. 2007-276182

(51) Int. Cl.

| | | |
|---|---|---|
| C12P 21/02 | (2006.01) | |
| C12N 5/00 | (2006.01) | |
| C12N 5/07 | (2010.01) | |
| C12N 5/16 | (2006.01) | |
| C07K 16/28 | (2006.01) | |
| C07K 16/30 | (2006.01) | |

(52) U.S. Cl.
CPC ............. *C12P 21/02* (2013.01); *C07K 16/2866* (2013.01); *C07K 16/303* (2013.01); *C07K 2317/14* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 5,658,786 A | 8/1997 | Smith et al. | |
| 6,184,007 B1 | 2/2001 | Dusch et al. | |
| 6,225,115 B1 | 5/2001 | Smith et al. | |
| 6,251,613 B1 | 6/2001 | Kishimoto et al. | |
| 6,316,238 B1 | 11/2001 | Nakamura et al. | |
| 6,812,339 B1 | 11/2004 | Venter et al. | |
| 7,413,536 B1 | 8/2008 | Dower et al. | |
| 7,919,086 B2 | 4/2011 | Nakano et al. | |
| 8,741,601 B2 * | 6/2014 | Tabuchi et al. | 435/69.6 |
| 2003/0165495 A1 | 9/2003 | Carulli et al. | |
| 2005/0221466 A1 | 10/2005 | Liao et al. | |
| 2005/0265983 A1 | 12/2005 | Melamed et al. | |
| 2006/0014937 A1 | 1/2006 | Kang et al. | |
| 2007/0162995 A1 | 7/2007 | Good et al. | |
| 2007/0166362 A1 | 7/2007 | Sakuma et al. | |
| 2007/0190599 A1 | 8/2007 | Nakano et al. | |
| 2009/0191591 A1 | 7/2009 | Tabuchi et al. | |
| 2009/0221442 A1 | 9/2009 | Dower et al. | |
| 2010/0167346 A1 | 7/2010 | Tabuchi et al. | |
| 2010/0233759 A1 | 9/2010 | Tabuchi et al. | |
| 2010/0248359 A1 | 9/2010 | Nakano et al. | |
| 2011/0003334 A1 | 1/2011 | Tabuchi et al. | |
| 2012/0045795 A1 | 2/2012 | Tabuchi et al. | |

FOREIGN PATENT DOCUMENTS

| | | |
|---|---|---|
| CN | 1612689 A | 5/2005 |
| CN | 1838969 A | 9/2006 |
| EP | 1 212 619 B1 | 5/2007 |
| EP | 2 213 746 A1 | 8/2010 |
| JP | 08-191693 A | 7/1996 |
| JP | 10-075787 A | 3/1998 |
| JP | 10-191984 A | 7/1998 |
| JP | 2000-228990 A | 8/2000 |
| JP | 2005-525100 A | 8/2005 |
| JP | 2006-506086 A | 2/2006 |
| WO | WO 92/04381 * | 3/1992 |
| WO | WO-97/27485 A1 | 7/1997 |
| WO | WO-01/20331 A1 | 3/2001 |
| WO | WO-02/092768 A2 | 11/2002 |
| WO | WO-03/039485 A2 | 5/2003 |
| WO | WO-2005/076015 A1 | 8/2005 |
| WO | WO-2006/006693 A1 | 1/2006 |
| WO | WO-2006/119115 A2 | 11/2006 |
| WO | WO-2007/056507 A1 | 5/2007 |
| WO | WO-2007/119774 A1 | 10/2007 |
| WO | WO-2008/114673 A1 | 9/2008 |
| WO | WO-2009/020144 A1 | 2/2009 |
| WO | WO-2009/051109 A1 | 4/2009 |
| WO | WO-2009/054433 A1 | 4/2009 |

OTHER PUBLICATIONS

Yang et al., J. Biol. Chem. 281:34525-34536, 2006.*
Wu et al., Chinese J. Physiol. 49:192-198, 2006.*
Lux et al., Proc. Natl. Acad. Sci. USA 86:9089-9093, 1989.*
GenBank Accession No. EGW01898, Aug. 2011, 2 pages.*
GenBank Accession No. AEQ38544, Oct. 2011, 2 pages.*
Kondo et al., Oncogene 17:2585-2591, 1998.*
Shen et al., Neoplasia 9:812-819, Oct. 2007.*
Romero et al., Mol. Aspects Med. 34:159-182, 2013.*
Chambard et al., J. Physiol. 550.3:667-677, 2003.*
International Search Report mailed Nov. 25, 2008 in PCT/JP2008/069184, 5 pages.
Alper, Seth L., "Molecular physiology of SLC4 anion exchangers," Exp. Physiol., 2006, 91:153-161.

(Continued)

*Primary Examiner* — David J Steadman
(74) *Attorney, Agent, or Firm* — Foley & Lardner LLP

(57) ABSTRACT

The present invention provides a method capable of producing a protein efficiently. A method of producing a polypeptide, comprising culturing a cell which strongly expresses a bicarbonate transporter and has a transferred DNA encoding a desired polypeptide and thereby allowing the cell to produce said polypeptide.

7 Claims, 10 Drawing Sheets

(56) References Cited

OTHER PUBLICATIONS

Database DDBJ/EMBL/GenBank [online], Accession No. NM_000342, uploaded Sep. 25, 2007, Keskanokwong et al., Definition: *Homo sapiens* solute carrier family 4, anion exchanger, member 1 (erythrocyte membrane protein band 3, Diego blood group) (SLC4A1), mRNA, retrieved Nov. 11, 2008, 12 pages.

Fu et al., "Direct interaction and cooperative role of tumor suppressor p16 with band 3 (AE1)," FEBS Letters, 2005, 579:2105-2110.

Supplementary European Search Report dated Oct. 21, 2010, in corresponding European Application No. 08841014.7, 6 pages.

Morgan et al., "Interactions of transmembrane carbonic anhydrase, CAIX, with bicarbonate transporters," Am. J. Physiol. Cell Physiol., Aug. 2007, 293(2):C738-C748.

Beckmann et al., "Coexpression of band 3 mutants and Rh polypeptides: differential effects of band 3 on the expression of the Rh complex containing D polypeptide and the Rh complex containing CcEe polypeptide," Blood, Apr. 15, 2001, 97(8):2496-2505.

Han et al., "Regulation of TauT by cisplatin in LLC-PK1 renal cells," Pediatr. Nephrol., 2005, 20:1067-1072.

Ishiguro et al., "CO2 permeability and bicarbonate transport in microperfused interlobular ducts isolated from guinea-pig pancreas," Journal of Physiology, 2000, 528.2:305-315.

Mount et al., "The SLC26 gene family of multifuntional anion exchangers," Pflugers Arch.-Eur. J. Physiol., 2004, 447: 710-721.

Pushkin et al., "SLC4 base (HCO-3, CO-23) transporters: classification, function, structure, genetic diseases, and knockout models," Am. J. Physiol. Renal Physiol., 2006, 290:F580-F599.

Final Office Action dated May 24, 2013 in U.S. Appl. No. 13/368,945.

Tanner et al., "The complete amino acid sequence of the human erythrocyte membrane anion-transport protein deduced from the cDNA sequence," Biochem. J., 1988, 256:703-712.

Final Office Action dated Dec. 17, 2010 in U.S. Appl. No. 12/226,195.

Final Office Action dated Aug. 23, 2011 in U.S. Appl. No. 12/733,815.

Notice of Allowance dated Dec. 20, 2012, in U.S. Appl. No. 12/733,052.

Office Action dated Jan. 6, 2011 in U.S. Appl. No. 12/733,815.

Office Action dated May 18, 2010 in U.S. Appl. No. 12/226,195.

Office Action dated Sep. 21, 2012 in U.S. Appl. No. 13/368,945.

Shibayama et al., "Effect of Methotrexate Treatment on Expression Levels of Organic Anion Transporter Polypeptide 2,P-Glycoprotein and Bile Salt Export Pump in Rats," Biol. Pharm. Bull., Mar. 2009, 32(3):493-496.

Office Action dated Feb. 27, 2013 in U.S. Appl. No. 13/138,909.

U.S. Appl. No. 13/368,945, filed Feb. 8, 2012, Tabuchi et al.

Arden et al., "Life and death in mammalian cell culture: strategies for apoptosis inhibition," Trends in Biotechnology, Apr. 2004, 22(4):174-180.

Bell et al., "Genetic Engineering of Hybridoma Glutamine Metabolism," Enzyme and Microbial Technology, 1995, 17(2):98-106.

Butler, Michael, "Animal cell cultures: recent achievements and perspectives in the production of biopharmaceuticals," Appl. Microbiol. Biotechnol., Aug. 2005, 68(3):283-291.

Christensen et al., "High expression of the taurine transporter TauT in primary cilic of NIH3T3 fibroblasts," Cell Biology International, 2005, 29:347-351.

Christie et al., "The Adaptation of BHK Cells to a Non-Ammoniagenic Glutamate-Based Culture Medium," Biotechnology and Bioengineering, Aug. 5, 1999, 64(3):298-309.

Database EMBL [Online] Jul. 23, 1992, XP002593029, retrieved from EBI accession No. EMBL:M95495, 3 pages.

Database Uniprot [Online] Jan. 10, 2006, XP002593032, retrieved from EBI accession No. UNIPROT:Q2VRP7, 1 page.

Database UniProt [Online] Jul. 1, 1993, XP002593028, retrieved from EBI accession No. UNIPROT:Q00589, 2 pages.

Database UniProt [Online] Jun. 1, 2001, "RecName: Full=Cysteine sulfinic acid decarboxylase; EC=4.1.1.29; AltName: Full=Cysteine-sulfinate decarboxylase; AltName: Full=Sulfinoalanine decarboxylase;" XP002597738 retrieved from EBI accession No. UNIPROT:Q9DBE0 Database accession No. Q9DBEO, 2 pages.

Database Uniprot [Online] Mar. 15, 2005, XP002593030, retrieved from EBI accession No. UNIPROT:Q5F431, 1 page.

Database Uniprot [Online] Oct. 1, 2000, XP002593031, retrieved from EBI accession No. UNIPROT:Q9MZ34, 2 pages.

de la Cruz Edmonds et al., "Development of Transfection and High-Producer Screening Protocols for the CHOK1SV Cell System." Molecular Biology, Oct. 1, 2006, 34(2):179-190.

de la Rosa et al., "Evidence for a Rate-Limiting Role of Cysteinesulfinate Decarboxylase Activity in Taurine Biosynthesis In Vivo," Comp. Biochem. Physiol., 1985, 81B(3):565-571.

Dusch et al., "Expression of the Corynebacterium glutamicum panD Gene Encoding L-Aspartate-alpha-Decarboxylase Leads to Pantothenate Overproduction in *Escherichia coli*," Applied and Environmental Microbiology, Apr. 1999, 65(4):1530-1539.

Final Office Action dated Mar. 1, 2012 in U.S. Appl. No. 12/733,052.

Ganapathy et al., "Expression and Regulation of the Taurine Transporter in Cultured Cell Lines of Human Origin," Advances in Experimental Medicine and Biology, 1994, 359:51-57, XP009123192.

Good et al., "Engineering nitrogen use efficiency with alanine aminotransferase," Canadian Journal of Botany, Mar. 1, 2007, 85(3):252-262.

Griffith, Owen W., "Crysteinesulfinate Metabolism, Altered Partitioning Between Transamination and Decarboxylation Following Administration of β-Methyleneaspartate," J. Biol. Chem., Feb. 10, 1983, 258(3):1591-1598.

Hammer et al., "β-Alanine but not taurine can function as an organic osmolyte in preimplantation mouse embryos cultured from fertilized eggs," Molecular Reproduction and Development, Oct. 2003, 66(2):153-161.

Han et al., "Is TauT an Anti-Apoptotic Gene?" Taurine 6, Oja et al. Eds., 2006, 59-67.

Hwang et al., "Expression and purification of recombinant human angiopoietin-2 produced in Chinese hamster ovary cells," Protein Expression and Purification, 2005, 39:175-183.

Ifandi et al., "Regulation of Cell Proliferation and Apoptosis in CHO-K1 Cells by the Coexpression of c-Myc and Bcl-2," Biotechnol. Prog., 2005, 21:671-677.

Ito et al., "Expression of taurine transporter is regulated through the TonE (tonicity-responsive element)/TonEBP (TonE-binding protein) pathway and contributes to cytoprotection in HepG2 cells," Biochem. J., 2004, 382:177-182.

Jhiang et al., "Cloning of the human taurine transporter and characterization of taurine uptake in thyroid cells," FEBS, Mar. 1, 1993, 318(2):139-144.

Kalwy et al., "Toward More Efficient Protein Expression," Molecular Biotechnology, Oct. 2006, 34(2):151-156.

Kennell et al,. "Principles and Practices of Nucleic Acid Hybridization," Prog. Nucleic Acid Res. Mol. Biol., 1971, 11:259-270.

Kim et al., "Response of recombinant Chinese hamster ovary cells to hyperosmotic pressure: effect of Bcl-2 overexpression," Journal of Biotechnology, 2002, 95:237-248.

Kim et al., "Characterization of Chimeric Antibody Producing CHO Cells in the Course of Dihydrofolate Reductase-Mediated Gene Amplification and Their Stability in the Absence of Selective Pressure," Biotechnology and Bioengineering, Apr. 5, 1998, 58(1):73-84.

Lee et al., "Development of Apoptosis-Resistant Dihydrofolate Reductase-Deficient Chinese Hamster Ovary Cell Line," Biotechnol. Bioengineer., 2003, 82:872-876.

Liu et al., "Cloning and expression of a cDNA encoding the transporter of taurine and β-alanine in mouse brain," Proc. Natl. Acad. Sci. USA, Dec. 1992, 89(24):12145-12149.

Miyasaka et al., "Characterization of Human Taurine Transporter Expressed in Insect Cells Using a Recombinant Baculovirus," Protein Expression and Purification, 2001, 23(3):389-397.

Ngo et al., "Computational Complexity, Protein Structure Prediction, and the Levinthal Paradox," The Protein Folding Problem and Tertiary Structure Prediction, Merz et al. (Eds.), 1994, 433 and 492-495.

Office Action dated May 12, 2011 in U.S. Appl. No. 12/733,052.

Office Action dated Aug. 9, 2011 in U.S. Appl. No. 12/450,161.

(56) References Cited

OTHER PUBLICATIONS

Porter et al., "Non-steady-state kinetics of brain glutamate decarboxylase resulting from interconversion of the apo- and holoenzyme," Biochimica et Biophysica Acta, 1988, 874:235-244.

Ramamoorthy et al., "Functional characterization and chromosomal localization of a cloned taurine transporter from human placenta," Biochem. J., 1994, 300:893-900.

Reymond et al., "Molecular cloning and sequence analysis of the cDNA encoding rat liver cysteine sulfinate decarboxylase (CSD)," Biochimica et Biophysica Acta, 1996, 1307:152-156.

Rudinger, J., "Characteristics of the amino acids as components of a peptide hormone sequence," Peptide Hormones, Parsons (Ed.), 1976, 1-7.

Smith et al., "Cloning and Expression of a High Affinity Taurine Transporter from Rat Brain," Mol. Pharmacol., 1992, 42(4):563-569.

Tabuchi et al., "Overexpression of Taurine Transporter in Chinese Hamster Ovary cells Can Enhance Cell Viability and Product Yield, While Promoting Glutamine Consumption," Biotechnology and Bioengineering, 2010, 107(6):998-1003.

Tang et al., "Protein Phosphorylation and Taurine Biosynthesis In Vivo and In Vitro," Journal of Neuroscience, Sep. 15, 1997, 17(18):6947-6951.

Tappaz et al., "Characterization of the cDNA Coding for Rat Brain Cysteine Sulfinate Decarboxylase: Brain and Liver Enzymes are Identical Proteins Encoded by Two Distince mRNAs," J. Neurochem., 1999, 73(3):903-912.

Tinland et al., "*Agrobacterium tumefaciens* transfers single-stranded transferred DNA (T-DNA) into the plant cell nucleus," Proc. Natl. Acad. Sci. USA, Aug. 1994, 91:8000-8004.

Trill et al., "Production of monoclonal antibodies in COS and CHO cells," Current Opinion in Biotechnology, 1995, 6:553-560.

Uchida et al., "Molecular cloning of the cDNA for an MDCK cell Na+- and Cl—dependent taurine transporter that is regulated by hypertonicity," Proc. Natl. Acad. Sci. USA, Sep. 1992, 89:8230-8234.

Voss et al., "Regulation of the expression and subcellular localization of the taurine transporter TauT in mouse NIH3T3 fibroblasts," Eur. J. Biochem., 2004, 271:4646-4658.

Wirth et al., "Isolation of overproducing recombinant mammalian cell lines by a fast and simple selection procedure," Gene, 1988, 73:419-426.

Yang et al., "cDNA Cloning, Genomic Structure, Chromosomal Mapping, and Functional Expression of a Novel Human Alanine Aminotransferase," Genomics, Mar. 1, 2002, 79(3):445-450.

Zhang et al., "Metabolic characteristics of recombinant Chinese hamster ovary cells expressing glutamine synthetase in presence and absence of glutamine," Cytotechnology, 2006, 51(1):21-28.

Han et al., "Mechanisms of regulation of taurine transporter activity," Taurine 6, Edited by Oja and Saransaari, 2006, 79-90.

Herman et al., "Low dose methotrexate induces apoptosis with reactive oxygen species involvement in T lymphocytic cell lines to a greater extent than in monocytic lines," Inflammation Research, 2005, 54:273-280.

\* cited by examiner

Antibody Yield

AE1/CSAD ( n = 9 )
( 1098 ± 139 ) mg/L

AE1/pPur ( n = 8 )
( 975 ± 122 ) mg/L t Test    P<0.05

Survival Ratio

AE1/CSAD ( n = 9 )
( 69 ± 4 ) %

AE1/pPur ( n = 8 )
( 56 ± 4 ) % t Test    P<0.01

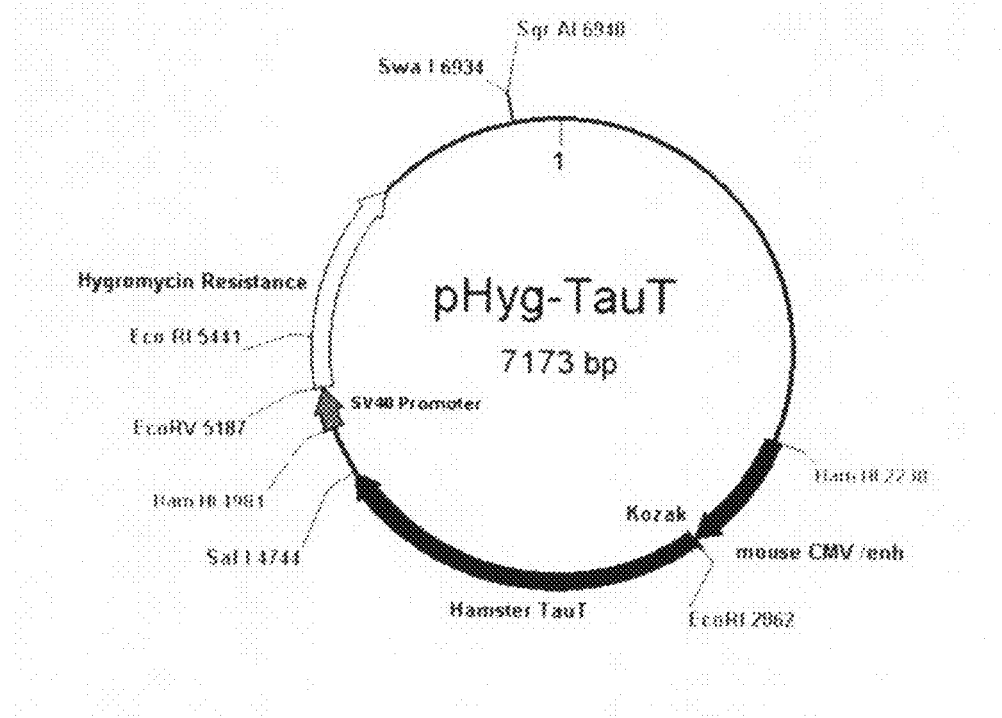

```
                        SEQUENCE LISTING

<160> NUMBER OF SEQ ID NOS: 11

<210> SEQ ID NO 1
<211> LENGTH: 2736
<212> TYPE: DNA
<213> ORGANISM: Homo sapiens

<400> SEQUENCE: 1
atggaggagc tgcaggatga ttatgaagac atgatggagg agaatctgga gcaggaggaa      60
tatgaagacc cagacatccc cgagtcccag atggaggagc cggcagctca cgacaccgag     120
gcaacagcca cagactacca caccacatca caccccggta cccacaaggt ctatgtggag     180
ctgcaggagc tggtgatgga cgaaaagaac caggagctga gatggatgga ggcggcgcgc     240
tgggtgcaac tggaggagaa cctgggggag aatggggcct ggggccgccc gcacctctct     300
cacctcacct tctggagcct cctagagctg cgtagagtct tcaccaaggg tactgttctc     360
ctagacctgc aagagacctc cctggctgga gtggccaacc aactgctaga caggtttatc     420
tttgaagacc agatccggcc tcaggaccga gaggagctgc tccgggccct gctgcttaaa     480
cacagccacg ctggagagct ggaggccctg gggggtgtga agcctgcagt cctgacacgc     540
tctggggatc cttcacagcc tctgctcccc caacactcct cactggagac acagctcttc     600
tgtgagcagg gagatggggg cacagaaggg cactcaccat ctggaattct ggaaaagatt     660
cccccggatt cagaggccac gttggtgcta gtgggccgcg ccgacttcct ggagcagccg     720
gtgctgggct tcgtgaggct gcaggaggca gcggagctgg aggcggtgga gctgccggtg     780
cctatacgct tcctctttgt gttgctggga cctgaggccc cccacatcga ttacacccag     840
cttggccggg ctgctgccac cctcatgtca gagagggtgt tccgcataga tgcctacatg     900
gctcagagcc gaggggagct gctgcactcc ctagagggct tcctggactg cagcctagtg     960
ctgcctccca ccgatgcccc ctccgagcag gcactgctca gtctggtgcc tgtgcagagg    1020
gagctacttc gaaggcgcta tcagtccagc cctgccaagc cagactccag cttctacaag    1080
ggcctagact taaatggggg cccagatgac cctctgcagc agacaggcca gctcttcggg    1140
ggcctggtgc gtgatatccg gcgccgctac ccctattacc tgagtgacat cacagatgca    1200
ttcagccccc aggtcctggc tgccgtcatc ttcatctact ttgctgcact gtcacccgcc    1260
atcaccttcg gcggcctcct gggagaaaag acccggaacc agatgggagt gtcggagctg    1320
ctgatctcca ctgcagtgca gggcattctc ttcgccctgc tggggctcca gcccctgctt    1380
gtggtcggct tctcaggacc cctgctggtg ttggaggaag ccttcttctc gttctgcgag    1440
accaacggtc tagagtacat cgtgggccgc gtgtggatcg gcttctggct catcctgctg    1500
gtggtgttgg tggtggcctt cgagggtagc ttcctggtcc gcttcatctc ccgctatacc    1560
```

```
caggagatct tctccttcct catttccctc atcttcatct atgagacttt ctccaagctg   1620
atcaagatct tccaggacca cccactacag aagacttata actacaacgt gttgatggtg   1680
cccaaacctc agggccccct gcccaacaca gccctcctct cccttgtgct catggccggt   1740
accttcttct ttgccatgat gctgcgcaag ttcaagaaca gctcctattt ccctggcaag   1800
ctgcgtcggg tcatcgggga cttcggggtc ccatctcca tcctgatcat ggtcctggtg   1860
gatttcttca ttcaggatac ctacacccag aaactctcgg tgcctgatgg cttcaaggtg   1920
tccaactcct cagcccgggg ctgggtcatc cacccactgg gcttgcgttc cgagtttccc   1980
atctggatga tgtttgcctc cgccctgcct gctctgctgg tcttcatcct catattcctg   2040
gagtctcaga tcaccacgct gattgtcagc aaacctgagc gcaagatggt caagggctcc   2100
ggcttccacc tggacctgct gctggtagta ggcatgggtg gggtggccgc cctctttggg   2160
atgccctggc tcagtgccac caccgtgcgt tccgtcaccc atgccaacgc cctcactgtc   2220
atgggcaaag ccagcacccc aggggctgca gcccagatcc aggaggtcaa agagcagcgg   2280
atcagtggac tcctggtcgc tgtgcttgtg ggcctgtcca tctcatgga gcccatcctg   2340 tcccgcatcc ccctggctgt actgtttggc atcttcctct acatgggggt cacgtcgctc   2400
agcggcatcc agctctttga ccgcatcttg cttctgttca gccacccaa gtatcaccca   2460 gatgtgccct acgtcaagcg ggtgaagacc tggcgcatgc acttattcac gggcatccag   2520
atcatctgcc tggcagtgct gtgggtggtg aagtccacgc cggcctccct ggccctgccc   2580
ttcgtcctca tctcactgt gccgctgcgg cgcgtcctgc tgccgctcat cttcaggaac   2640
gtggagcttc agtgtctgga tgctgatgat gccaaggcaa cctttgatga ggaggaaggt   2700
cgggatgaat acgacgaagt ggccatgcct gtgtga                            2736

<210> SEQ ID NO 2
<211> LENGTH: 911
<212> TYPE: PRT
<213> ORGANISM: Homo sapiens

<400> SEQUENCE: 2

Met Glu Glu Leu Gln Asp Asp Tyr Glu Asp Met Met Glu Glu Asn Leu
1               5                   10                  15

Glu Gln Glu Glu Tyr Glu Asp Pro Asp Ile Pro Glu Ser Gln Met Glu
            20                  25                  30

Glu Pro Ala Ala His Asp Thr Glu Ala Thr Ala Thr Asp Tyr His Thr
        35                  40                  45

Thr Ser His Pro Gly Thr His Lys Val Tyr Val Glu Leu Gln Glu Leu
    50                  55                  60

Val Met Asp Glu Lys Asn Gln Glu Leu Arg Trp Met Glu Ala Ala Arg
65                  70                  75                  80

Trp Val Gln Leu Glu Glu Asn Leu Gly Glu Asn Gly Ala Trp Gly Arg
                85                  90                  95

Pro His Leu Ser His Leu Thr Phe Trp Ser Leu Leu Glu Leu Arg Arg
            100                 105                 110

Val Phe Thr Lys Gly Thr Val Leu Leu Asp Leu Gln Glu Thr Ser Leu
        115                 120                 125

Ala Gly Val Ala Asn Gln Leu Leu Asp Arg Phe Ile Phe Glu Asp Gln
    130                 135                 140

Ile Arg Pro Gln Asp Arg Glu Glu Leu Leu Arg Ala Leu Leu Leu Lys
145                 150                 155                 160
```

```
His Ser His Ala Gly Glu Leu Glu Ala Leu Gly Gly Val Lys Pro Ala
            165                 170                 175

Val Leu Thr Arg Ser Gly Asp Pro Ser Gln Pro Leu Leu Pro Gln His
            180                 185                 190

Ser Ser Leu Glu Thr Gln Leu Phe Cys Glu Gln Gly Asp Gly Gly Thr
            195                 200                 205

Glu Gly His Ser Pro Ser Gly Ile Leu Glu Lys Ile Pro Pro Asp Ser
            210                 215                 220

Glu Ala Thr Leu Val Leu Val Gly Arg Ala Asp Phe Leu Glu Gln Pro
225                 230                 235                 240

Val Leu Gly Phe Val Arg Leu Gln Glu Ala Ala Glu Leu Glu Ala Val
            245                 250                 255

Glu Leu Pro Val Pro Ile Arg Phe Leu Phe Val Leu Leu Gly Pro Glu
            260                 265                 270

Ala Pro His Ile Asp Tyr Thr Gln Leu Gly Arg Ala Ala Ala Thr Leu
            275                 280                 285

Met Ser Glu Arg Val Phe Arg Ile Asp Ala Tyr Met Ala Gln Ser Arg
            290                 295                 300

Gly Glu Leu Leu His Ser Leu Glu Gly Phe Leu Asp Cys Ser Leu Val
305                 310                 315                 320

Leu Pro Pro Thr Asp Ala Pro Ser Glu Gln Ala Leu Leu Ser Leu Val
            325                 330                 335

Pro Val Gln Arg Glu Leu Leu Arg Arg Arg Tyr Gln Ser Ser Pro Ala
            340                 345                 350

Lys Pro Asp Ser Ser Phe Tyr Lys Gly Leu Asp Leu Asn Gly Gly Pro
            355                 360                 365

Asp Asp Pro Leu Gln Gln Thr Gly Gln Leu Phe Gly Gly Leu Val Arg
            370                 375                 380

Asp Ile Arg Arg Arg Tyr Pro Tyr Tyr Leu Ser Asp Ile Thr Asp Ala
385                 390                 395                 400

Phe Ser Pro Gln Val Leu Ala Ala Val Ile Phe Ile Tyr Phe Ala Ala
            405                 410                 415

Leu Ser Pro Ala Ile Thr Phe Gly Gly Leu Leu Gly Glu Lys Thr Arg
            420                 425                 430

Asn Gln Met Gly Val Ser Glu Leu Leu Ile Ser Thr Ala Val Gln Gly
            435                 440                 445

Ile Leu Phe Ala Leu Leu Gly Ala Gln Pro Leu Leu Val Val Gly Phe
            450                 455                 460

Ser Gly Pro Leu Leu Val Phe Glu Glu Ala Phe Phe Ser Phe Cys Glu
465                 470                 475                 480

Thr Asn Gly Leu Glu Tyr Ile Val Gly Arg Val Trp Ile Gly Phe Trp
            485                 490                 495

Leu Ile Leu Leu Val Val Leu Val Ala Phe Glu Gly Ser Phe Leu
            500                 505                 510

Val Arg Phe Ile Ser Arg Tyr Thr Gln Glu Ile Phe Ser Phe Leu Ile
            515                 520                 525

Ser Leu Ile Phe Ile Tyr Glu Thr Phe Ser Lys Leu Ile Lys Ile Phe
            530                 535                 540

Gln Asp His Pro Leu Gln Lys Thr Tyr Asn Tyr Asn Val Leu Met Val
545                 550                 555                 560

Pro Lys Pro Gln Gly Pro Leu Pro Asn Thr Ala Leu Leu Ser Leu Val
            565                 570                 575

Leu Met Ala Gly Thr Phe Phe Phe Ala Met Met Leu Arg Lys Phe Lys
```

```
                580             585             590
Asn Ser Ser Tyr Phe Pro Gly Lys Leu Arg Val Ile Gly Asp Phe
                595             600             605

Gly Val Pro Ile Ser Ile Leu Ile Met Val Leu Val Asp Phe Phe Ile
610                 615                 620

Gln Asp Thr Tyr Thr Gln Lys Leu Ser Val Pro Asp Gly Phe Lys Val
625                 630                 635                 640

Ser Asn Ser Ser Ala Arg Gly Trp Val Ile His Pro Leu Gly Leu Arg
                645                 650                 655

Ser Glu Phe Pro Ile Trp Met Met Phe Ala Ser Ala Leu Pro Ala Leu
                660                 665                 670

Leu Val Phe Ile Leu Ile Phe Leu Glu Ser Gln Ile Thr Thr Leu Ile
                675                 680                 685

Val Ser Lys Pro Glu Arg Lys Met Val Lys Gly Ser Gly Phe His Leu
                690                 695                 700

Asp Leu Leu Val Val Gly Met Gly Gly Val Ala Ala Leu Phe Gly
705                 710                 715                 720

Met Pro Trp Leu Ser Ala Thr Thr Val Arg Ser Val Thr His Ala Asn
                725                 730                 735

Ala Leu Thr Val Met Gly Lys Ala Ser Thr Pro Gly Ala Ala Ala Gln
                740                 745                 750

Ile Gln Glu Val Lys Glu Gln Arg Ile Ser Gly Leu Leu Val Ala Val
                755                 760                 765

Leu Val Gly Leu Ser Ile Leu Met Glu Pro Ile Leu Ser Arg Ile Pro
                770                 775                 780

Leu Ala Val Leu Phe Gly Ile Phe Leu Tyr Met Gly Val Thr Ser Leu
785                 790                 795                 800

Ser Gly Ile Gln Leu Phe Asp Arg Ile Leu Leu Leu Phe Lys Pro Pro
                805                 810                 815

Lys Tyr His Pro Asp Val Pro Tyr Val Lys Arg Val Lys Thr Trp Arg
                820                 825                 830

Met His Leu Phe Thr Gly Ile Gln Ile Ile Cys Leu Ala Val Leu Trp
                835                 840                 845

Val Val Lys Ser Thr Pro Ala Ser Leu Ala Leu Pro Phe Val Leu Ile
                850                 855                 860

Leu Thr Val Pro Leu Arg Arg Val Leu Leu Pro Leu Ile Phe Arg Asn
865                 870                 875                 880

Val Glu Leu Gln Cys Leu Asp Ala Asp Ala Lys Ala Thr Phe Asp
                885                 890                 895

Glu Glu Glu Gly Arg Asp Glu Tyr Asp Glu Val Ala Met Pro Val
                900                 905                 910

<210> SEQ ID NO 3
<211> LENGTH: 1482
<212> TYPE: DNA
<213> ORGANISM: Cricetulus griseus
<220> FEATURE:
<221> NAME/KEY: CDS
<222> LOCATION: (1)..(1479)

<400> SEQUENCE: 3 atg gct gac tca aaa cca ctc aat gcc ctg gat ggg gac cct gtg gct    48
Met Ala Asp Ser Lys Pro Leu Asn Ala Leu Asp Gly Asp Pro Val Ala
1               5                   10                  15 gtg gag tcc tta ctc cgg gat gtg ttt ggg att gtt gta gat gag gcc    96
Val Glu Ser Leu Leu Arg Asp Val Phe Gly Ile Val Val Asp Glu Ala
```

```
                      20                     25                      30
att cgg aaa ggg acc agt gcc tcg gag aag gtt tgt gaa tgg aag gag        144
Ile Arg Lys Gly Thr Ser Ala Ser Glu Lys Val Cys Glu Trp Lys Glu
         35                      40                      45 cct gaa gag ctc aag cat ctg ctg gat ttg gag ctg cag agc cag ggc        192
Pro Glu Glu Leu Lys His Leu Leu Asp Leu Glu Leu Gln Ser Gln Gly
 50                      55                      60 gag tct caa gag cag att cta gag cgc tgc cgg gct gtg att cac tac        240
Glu Ser Gln Glu Gln Ile Leu Glu Arg Cys Arg Ala Val Ile His Tyr
 65                      70                      75                  80 agt gtc aag act ggt cac ccc cgg ttc ttc aac cag ctc ttc tca ggg        288
Ser Val Lys Thr Gly His Pro Arg Phe Phe Asn Gln Leu Phe Ser Gly
                 85                      90                      95 tta gac ccc cat gct ctg gct ggg cgc atc atc aca gaa agc ctc aac        336
Leu Asp Pro His Ala Leu Ala Gly Arg Ile Ile Thr Glu Ser Leu Asn
                100                     105                     110 acc agc cag tac aca tat gag att gcc cct gtg ttt gtc ctc atg gaa        384
Thr Ser Gln Tyr Thr Tyr Glu Ile Ala Pro Val Phe Val Leu Met Glu
            115                     120                     125 gag gag gtg ctg aag aaa ctc cgt gcc ctg gtg ggc tgg aac tct ggg        432
Glu Glu Val Leu Lys Lys Leu Arg Ala Leu Val Gly Trp Asn Ser Gly
130                     135                     140 gat ggg gtc ttc tgt cct ggt ggc tcc atc tcg aac atg tat gcc atg        480
Asp Gly Val Phe Cys Pro Gly Gly Ser Ile Ser Asn Met Tyr Ala Met
145                     150                     155                 160 aac ctg gcc cgc tat cag cgc tac cca gac tgc aag caa aga ggc ctc        528
Asn Leu Ala Arg Tyr Gln Arg Tyr Pro Asp Cys Lys Gln Arg Gly Leu
                165                     170                     175 cgg gcc ctg ccg ccc ttg gct ctc ttc act tca aag gag tgt cac tac        576
Arg Ala Leu Pro Pro Leu Ala Leu Phe Thr Ser Lys Glu Cys His Tyr
                180                     185                     190 tcc atc agt aag gga gct gct ttt ctg gga ctt ggc act gac agt gtc        624
Ser Ile Ser Lys Gly Ala Ala Phe Leu Gly Leu Gly Thr Asp Ser Val
            195                     200                     205 cga gtg gtc aag gct gat gag aga ggg aaa atg atc cct gag gat ctg        672
Arg Val Val Lys Ala Asp Glu Arg Gly Lys Met Ile Pro Glu Asp Leu
210                     215                     220 gag agg cag atc agt ctg gct gag gca gag ggc tct gtg cca ttt ctg        720
Glu Arg Gln Ile Ser Leu Ala Glu Ala Glu Gly Ser Val Pro Phe Leu
225                     230                     235                 240 gtc agt acc acc tct ggt acc acc gtg cta ggg gcc ttt gac ccc ctg        768
Val Ser Thr Thr Ser Gly Thr Thr Val Leu Gly Ala Phe Asp Pro Leu
                245                     250                     255 gat gca att gct gat gtt tgc cag cgt cac gga tta tgg tta cac gtg        816
Asp Ala Ile Ala Asp Val Cys Gln Arg His Gly Leu Trp Leu His Val
                260                     265                     270 gat gcc gcc tgg ggt ggg agc gtc ctg ctg tcc cgg aca cac agg cat        864
Asp Ala Ala Trp Gly Gly Ser Val Leu Leu Ser Arg Thr His Arg His
            275                     280                     285 ctc ctg gat ggg atc cag agg gct gac tct gtg gcc tgg aac cct cac        912
Leu Leu Asp Gly Ile Gln Arg Ala Asp Ser Val Ala Trp Asn Pro His
290                     295                     300 aag ctt ctc ggt gca ggg ctg cag tgc tct gct ctt ctc cgg gac            960
Lys Leu Leu Gly Ala Gly Leu Gln Cys Ser Ala Leu Leu Arg Asp
305                     310                     315                 320 acc tcg aac ctg ctc aag cgc tgc cat ggg tcc cag gcc agc tac ctg       1008
Thr Ser Asn Leu Leu Lys Arg Cys His Gly Ser Gln Ala Ser Tyr Leu
                325                     330                     335 ttc cag cag gac aaa ttc tat gac gtg gct ctt gac act gga gac aag       1056
Phe Gln Gln Asp Lys Phe Tyr Asp Val Ala Leu Asp Thr Gly Asp Lys
```

```
Phe Gln Gln Asp Lys Phe Tyr Asp Val Ala Leu Asp Thr Gly Asp Lys
                340                 345                 350 gtg gtg cag tgt ggc cgc cgt gtg gac tgt ctg aag ttg tgg ctc atg       1104
Val Val Gln Cys Gly Arg Arg Val Asp Cys Leu Lys Leu Trp Leu Met
            355                 360                 365 tgg aag gca cag ggt ggg caa gga ctg gag cgg cgc atc gac cag gcc       1152
Trp Lys Ala Gln Gly Gly Gln Gly Leu Glu Arg Arg Ile Asp Gln Ala
370                 375                 380 ttt gct ctc acc cgg tac ctg gtg gag gag ata aaa aag cgg gaa gga       1200
Phe Ala Leu Thr Arg Tyr Leu Val Glu Glu Ile Lys Lys Arg Glu Gly
385                 390                 395                 400 ttt gag ttg gtc atg gag cct gag ttt gtc aat gtg tgc ttc tgg ttt       1248
Phe Glu Leu Val Met Glu Pro Glu Phe Val Asn Val Cys Phe Trp Phe
            405                 410                 415 gtg cct ccc agc ctg cgg ggg aag aaa gag agt cca gat tac agc aaa       1296
Val Pro Pro Ser Leu Arg Gly Lys Lys Glu Ser Pro Asp Tyr Ser Lys
        420                 425                 430 agg ctg tct cag gtg gcg cct gta ctc aag gag cgc atg gtg aag aag       1344
Arg Leu Ser Gln Val Ala Pro Val Leu Lys Glu Arg Met Val Lys Lys
    435                 440                 445 ggc tcc atg atg att ggc tac cag ccc cat ggg acc cgg gcc aac ttc       1392
Gly Ser Met Met Ile Gly Tyr Gln Pro His Gly Thr Arg Ala Asn Phe
450                 455                 460 ttc cgg atg gtg gtg gcc aac ccc aca ctg acc cag gct gat ata gac       1440
Phe Arg Met Val Val Ala Asn Pro Thr Leu Thr Gln Ala Asp Ile Asp
465                 470                 475                 480 ttc ctt ctg ggc gag ctg gag cgt ctg ggc cag gac ctg tga              1482
Phe Leu Leu Gly Glu Leu Glu Arg Leu Gly Gln Asp Leu
            485                 490

<210> SEQ ID NO 4
<211> LENGTH: 493
<212> TYPE: PRT
<213> ORGANISM: Cricetulus griseus

<400> SEQUENCE: 4

Met Ala Asp Ser Lys Pro Leu Asn Ala Leu Asp Gly Asp Pro Val Ala
1               5                   10                  15

Val Glu Ser Leu Leu Arg Asp Val Phe Gly Ile Val Val Asp Glu Ala
            20                  25                  30

Ile Arg Lys Gly Thr Ser Ala Ser Glu Lys Val Cys Glu Trp Lys Glu
        35                  40                  45

Pro Glu Glu Leu Lys His Leu Leu Asp Leu Glu Leu Gln Ser Gln Gly
    50                  55                  60

Glu Ser Gln Glu Gln Ile Leu Glu Arg Cys Arg Ala Val Ile His Tyr
65                  70                  75                  80

Ser Val Lys Thr Gly His Pro Arg Phe Phe Asn Gln Leu Phe Ser Gly
                85                  90                  95

Leu Asp Pro His Ala Leu Ala Gly Arg Ile Ile Thr Glu Ser Leu Asn
            100                 105                 110

Thr Ser Gln Tyr Thr Tyr Glu Ile Ala Pro Val Phe Val Leu Met Glu
        115                 120                 125

Glu Glu Val Leu Lys Lys Leu Arg Ala Leu Val Gly Trp Asn Ser Gly
    130                 135                 140

Asp Gly Val Phe Cys Pro Gly Gly Ser Ile Ser Asn Met Tyr Ala Met
145                 150                 155                 160

Asn Leu Ala Arg Tyr Gln Arg Tyr Pro Asp Cys Lys Gln Arg Gly Leu
                165                 170                 175
```

Arg Ala Leu Pro Pro Leu Ala Leu Phe Thr Ser Lys Glu Cys His Tyr
           180                 185                 190

Ser Ile Ser Lys Gly Ala Ala Phe Leu Gly Leu Gly Thr Asp Ser Val
        195                 200                 205

Arg Val Val Lys Ala Asp Glu Arg Gly Lys Met Ile Pro Glu Asp Leu
    210                 215                 220

Glu Arg Gln Ile Ser Leu Ala Glu Ala Glu Gly Ser Val Pro Phe Leu
225                 230                 235                 240

Val Ser Thr Thr Ser Gly Thr Thr Val Leu Gly Ala Phe Asp Pro Leu
                245                 250                 255

Asp Ala Ile Ala Asp Val Cys Gln Arg His Gly Leu Trp Leu His Val
            260                 265                 270

Asp Ala Ala Trp Gly Gly Ser Val Leu Leu Ser Arg Thr His Arg His
        275                 280                 285

Leu Leu Asp Gly Ile Gln Arg Ala Asp Ser Val Ala Trp Asn Pro His
    290                 295                 300

Lys Leu Leu Gly Ala Gly Leu Gln Cys Ser Ala Leu Leu Leu Arg Asp
305                 310                 315                 320

Thr Ser Asn Leu Leu Lys Arg Cys His Gly Ser Gln Ala Ser Tyr Leu
                325                 330                 335

Phe Gln Gln Asp Lys Phe Tyr Asp Val Ala Leu Asp Thr Gly Asp Lys
            340                 345                 350

Val Val Gln Cys Gly Arg Arg Val Asp Cys Leu Lys Leu Trp Leu Met
        355                 360                 365

Trp Lys Ala Gln Gly Gly Gln Gly Leu Glu Arg Arg Ile Asp Gln Ala
    370                 375                 380

Phe Ala Leu Thr Arg Tyr Leu Val Glu Glu Ile Lys Lys Arg Glu Gly
385                 390                 395                 400

Phe Glu Leu Val Met Glu Pro Glu Phe Val Asn Val Cys Phe Trp Phe
                405                 410                 415

Val Pro Pro Ser Leu Arg Gly Lys Lys Glu Ser Pro Asp Tyr Ser Lys
            420                 425                 430

Arg Leu Ser Gln Val Ala Pro Val Leu Lys Glu Arg Met Val Lys Lys
        435                 440                 445

Gly Ser Met Met Ile Gly Tyr Gln Pro His Gly Thr Arg Ala Asn Phe
    450                 455                 460

Phe Arg Met Val Val Ala Asn Pro Thr Leu Thr Gln Ala Asp Ile Asp
465                 470                 475                 480

Phe Leu Leu Gly Glu Leu Glu Arg Leu Gly Gln Asp Leu
                485                 490

<210> SEQ ID NO 5
<211> LENGTH: 1491
<212> TYPE: DNA
<213> ORGANISM: Homo sapiens

<400> SEQUENCE: 5
atggcctcga gcacaggtga ccggagccag gcggtgaggc atggactgag ggcgaaggtg    60
ctgacgctgg acggcatgaa cccgcgtgtg cggagagtgg agtacgcagt gcgtggcccc   120
atagtgcagc gagccttgga gctggagcag agctgcgcc agggtgtgaa gaagcctttc   180
accgaggtca tccgtgccaa catcggggac gcacaggcta tggggcagag gcccatcacc   240
ttcctgcgcc aggtcttggc cctctgtgtt aaccctgatc ttctgagcag ccccaacttc   300

-continued

```
cctgacgatg ccaagaaaag ggcggagcgc atcttgcagg cgtgtggggg ccacagtctg    360
ggggcctaca cgtcagctc cggcatccag ctgatccggg aggacgtggc gcggtacatt     420
gagaggcgtg acggaggcat ccctgcggac cccaacaacg tcttcctgtc cacaggggcc    480
agcgatgcca tcgtgacggt gctgaagctg ctggtggccg gcgagggcca cacgcacg      540
ggtgtgctca tccccatccc ccagtaccca ctctactcgg ccacgctggc agagctgggc    600
gcagtgcagg tggattacta cctggacgag gagcgtgcct gggcgctgga cgtgccgag     660
cttcaccgtg cactgggcca ggcgcgtgac cactgccgcc ctcgtgcgct ctgtgtcatc    720
aaccctggca ccccaccgg gcaggtgcag acccgcgagt gcatcgaggc cgtgatccgc     780
ttcgccttcg aagagcggct ctttctgctg gcggacgagg tgtaccagga caacgtgtac    840
gccgcgggtt cgcagttcca ctcattcaag aaggtgctca tggagatggg ccgcccctac    900
gccgggcagc aggagcttgc ctccttccac tccacctcca agggctacat gggcgagtgc    960
gggttccgcg cggctatgt ggaggtggtg aacatggacg ctgcagtgca gcagcagatg    1020
ctgaagctga tgagtgtgcg gctgtgcccg ccggtgccag acaggccct gctggacctg    1080
gtggtcagcc cgcccgcgcc caccgacccc tcctttgcgc agttccaggc tgagaagcag   1140
gcagtgctgg cagagctggc ggccaaggcc aagctcaccg agcaggtctt caatgaggct    1200
cctggcatca gctgcaaccc agtgcagggc gccatgtact ccttcccgcg cgtgcagctg   1260
ccccgcggg cggtggagcg cgctcaggag ctgggcctgg ccccgatat gttcttctgc    1320
ctgcgcctcc tggaggagac cggcatctgc gtggtgccag ggagcggctt tgggcagcgg   1380
gaaggcacct accacttccg gatgaccatt ctgcccccct ggagaaaact gcggctgctg    1440
ctggagaagc tgagcaggtt ccatgccaag ttcaccctcg agtactcctg a             1491
```

<210> SEQ ID NO 6
<211> LENGTH: 992
<212> TYPE: PRT
<213> ORGANISM: Homo sapiens

<400> SEQUENCE: 6

```
Met Ala Ser Ser Thr Gly Asp Arg Ser Gln Ala Val Arg His Gly Leu
1               5                   10                  15

Arg Ala Lys Val Leu Thr Leu Asp Gly Met Asn Pro Arg Val Arg Arg
            20                  25                  30

Val Glu Tyr Ala Val Arg Gly Pro Ile Val Gln Arg Ala Leu Glu Leu
        35                  40                  45

Glu Gln Glu Leu Arg Gln Gly Val Lys Lys Pro Phe Thr Glu Val Ile
    50                  55                  60

Arg Ala Asn Ile Gly Asp Ala Gln Ala Met Gly Gln Arg Pro Ile Thr
65                  70                  75                  80

Phe Leu Arg Gln Val Leu Ala Leu Cys Val Asn Pro Asp Leu Leu Ser
                85                  90                  95

Ser Pro Asn Phe Pro Asp Asp Ala Lys Lys Arg Ala Glu Arg Ile Leu
            100                 105                 110

Gln Ala Cys Gly Gly His Ser Leu Gly Ala Tyr Ser Val Ser Ser Gly
        115                 120                 125

Ile Gln Leu Ile Arg Glu Asp Val Ala Arg Tyr Ile Glu Arg Arg Asp
    130                 135                 140

Gly Gly Ile Pro Ala Asp Pro Asn Asn Val Phe Leu Ser Thr Gly Ala
145                 150                 155                 160

Ser Asp Ala Ile Val Thr Val Leu Lys Leu Leu Val Ala Gly Glu Gly
```

-continued

```
                  165                 170                 175
His Thr Arg Thr Gly Val Leu Ile Pro Ile Pro Gln Tyr Pro Leu Tyr
                180                 185                 190

Ser Ala Thr Leu Ala Glu Leu Gly Ala Val Gln Val Asp Tyr Tyr Leu
                195                 200                 205

Asp Glu Glu Arg Ala Trp Ala Leu Asp Val Ala Glu Leu His Arg Ala
                210                 215                 220

Leu Gly Gln Ala Arg Asp His Cys Arg Pro Arg Ala Leu Cys Val Ile
225                 230                 235                 240

Asn Pro Gly Asn Pro Thr Gly Gln Val Gln Thr Arg Glu Cys Ile Glu
                245                 250                 255

Ala Val Ile Arg Phe Ala Phe Glu Glu Arg Leu Phe Leu Leu Ala Asp
                260                 265                 270

Glu Val Tyr Gln Asp Asn Val Tyr Ala Ala Gly Ser Gln Phe His Ser
                275                 280                 285

Phe Lys Lys Val Leu Met Glu Met Gly Pro Pro Tyr Ala Gly Gln Gln
                290                 295                 300

Glu Leu Ala Ser Phe His Ser Thr Ser Lys Gly Tyr Met Gly Glu Cys
305                 310                 315                 320

Gly Phe Arg Gly Gly Tyr Val Glu Val Val Asn Met Asp Ala Ala Val
                325                 330                 335

Gln Gln Gln Met Leu Lys Leu Met Ser Val Arg Leu Cys Pro Pro Val
                340                 345                 350

Pro Gly Gln Ala Leu Leu Asp Leu Val Val Ser Pro Pro Ala Pro Thr
                355                 360                 365

Asp Pro Ser Phe Ala Gln Phe Gln Ala Glu Lys Gln Ala Val Leu Ala
                370                 375                 380

Glu Leu Ala Ala Lys Ala Lys Leu Thr Glu Gln Val Phe Asn Glu Ala
385                 390                 395                 400

Pro Gly Ile Ser Cys Asn Pro Val Gln Gly Ala Met Tyr Ser Phe Pro
                405                 410                 415

Arg Val Gln Leu Pro Pro Arg Ala Val Glu Arg Ala Gln Glu Leu Gly
                420                 425                 430

Leu Ala Pro Asp Met Phe Phe Cys Leu Arg Leu Leu Glu Glu Thr Gly
                435                 440                 445

Ile Cys Val Val Pro Gly Ser Gly Phe Gly Gln Arg Glu Gly Thr Tyr
                450                 455                 460

His Phe Arg Met Thr Ile Leu Pro Pro Leu Glu Lys Leu Arg Leu Leu
465                 470                 475                 480

Leu Glu Lys Leu Ser Arg Phe His Ala Lys Phe Thr Leu Glu Tyr Ser
                485                 490                 495

Met Ala Ser Ser Thr Gly Asp Arg Ser Gln Ala Val Arg His Gly Leu
                500                 505                 510

Arg Ala Lys Val Leu Thr Leu Asp Gly Met Asn Pro Arg Val Arg Arg
                515                 520                 525

Val Glu Tyr Ala Val Arg Gly Pro Ile Val Gln Arg Ala Leu Glu Leu
                530                 535                 540

Glu Gln Glu Leu Arg Gln Gly Val Lys Lys Pro Phe Thr Glu Val Ile
545                 550                 555                 560

Arg Ala Asn Ile Gly Asp Ala Gln Ala Met Gly Gln Arg Pro Ile Thr
                565                 570                 575

Phe Leu Arg Gln Val Leu Ala Leu Cys Val Asn Pro Asp Leu Leu Ser
                580                 585                 590
```

```
Ser Pro Asn Phe Pro Asp Asp Ala Lys Lys Arg Ala Glu Arg Ile Leu
    595                 600                 605

Gln Ala Cys Gly Gly His Ser Leu Gly Ala Tyr Ser Val Ser Ser Gly
    610                 615                 620

Ile Gln Leu Ile Arg Glu Asp Val Ala Arg Tyr Ile Glu Arg Arg Asp
625                 630                 635                 640

Gly Gly Ile Pro Ala Asp Pro Asn Asn Val Phe Leu Ser Thr Gly Ala
                645                 650                 655

Ser Asp Ala Ile Val Thr Val Leu Lys Leu Leu Val Ala Gly Glu Gly
                660                 665                 670

His Thr Arg Thr Gly Val Leu Ile Pro Ile Pro Gln Tyr Pro Leu Tyr
    675                 680                 685

Ser Ala Thr Leu Ala Glu Leu Gly Ala Val Gln Val Asp Tyr Tyr Leu
    690                 695                 700

Asp Glu Glu Arg Ala Trp Ala Leu Asp Val Ala Glu Leu His Arg Ala
705                 710                 715                 720

Leu Gly Gln Ala Arg Asp His Cys Arg Pro Arg Ala Leu Cys Val Ile
                725                 730                 735

Asn Pro Gly Asn Pro Thr Gly Gln Val Gln Thr Arg Glu Cys Ile Glu
                740                 745                 750

Ala Val Ile Arg Phe Ala Phe Glu Glu Arg Leu Phe Leu Leu Ala Asp
    755                 760                 765

Glu Val Tyr Gln Asp Asn Val Tyr Ala Ala Gly Ser Gln Phe His Ser
    770                 775                 780

Phe Lys Lys Val Leu Met Glu Met Gly Pro Pro Tyr Ala Gly Gln Gln
785                 790                 795                 800

Glu Leu Ala Ser Phe His Ser Thr Ser Lys Gly Tyr Met Gly Glu Cys
                805                 810                 815

Gly Phe Arg Gly Gly Tyr Val Glu Val Val Asn Met Asp Ala Ala Val
                820                 825                 830

Gln Gln Gln Met Leu Lys Leu Met Ser Val Arg Leu Cys Pro Pro Val
    835                 840                 845

Pro Gly Gln Ala Leu Leu Asp Leu Val Val Ser Pro Pro Ala Pro Thr
    850                 855                 860

Asp Pro Ser Phe Ala Gln Phe Gln Ala Glu Lys Gln Ala Val Leu Ala
865                 870                 875                 880

Glu Leu Ala Ala Lys Ala Lys Leu Thr Glu Gln Val Phe Asn Glu Ala
                885                 890                 895

Pro Gly Ile Ser Cys Asn Pro Val Gln Gly Ala Met Tyr Ser Phe Pro
                900                 905                 910

Arg Val Gln Leu Pro Pro Arg Ala Val Glu Arg Ala Gln Glu Leu Gly
    915                 920                 925

Leu Ala Pro Asp Met Phe Phe Cys Leu Arg Leu Leu Glu Glu Thr Gly
    930                 935                 940

Ile Cys Val Val Pro Gly Ser Gly Phe Gly Gln Arg Glu Gly Thr Tyr
945                 950                 955                 960

His Phe Arg Met Thr Ile Leu Pro Pro Leu Glu Lys Leu Arg Leu Leu
                965                 970                 975

Leu Glu Lys Leu Ser Arg Phe His Ala Lys Phe Thr Leu Glu Tyr Ser
                980                 985                 990

<210> SEQ ID NO 7
<211> LENGTH: 1869
```

<212> TYPE: DNA
<213> ORGANISM: Cricetulus griseus
<220> FEATURE:
<221> NAME/KEY: CDS
<222> LOCATION: (1)..(1866)

<400> SEQUENCE: 7

```
atg gcc acc aag gag aag ctg cag tgt ctg aaa gac ttc cac aaa gac        48
Met Ala Thr Lys Glu Lys Leu Gln Cys Leu Lys Asp Phe His Lys Asp
1               5                   10                  15 atc ctg aag cct tct cca ggg aag agc cca ggc aca cgg cct gag gat        96
Ile Leu Lys Pro Ser Pro Gly Lys Ser Pro Gly Thr Arg Pro Glu Asp
                20                  25                  30 gag gct gag ggg aag ccc cct cag agg gag aag tgg tcc agc aag att        144
Glu Ala Glu Gly Lys Pro Pro Gln Arg Glu Lys Trp Ser Ser Lys Ile
            35                  40                  45 gac ttt gtg ctg tct gtg gcc gga ggc ttc gtg ggt ttg ggc aac gtt        192
Asp Phe Val Leu Ser Val Ala Gly Gly Phe Val Gly Leu Gly Asn Val
    50                  55                  60 tgg cgt ttc ccg tac ctc tgc tac aaa aat ggt gga ggt gct ttc ctc        240
Trp Arg Phe Pro Tyr Leu Cys Tyr Lys Asn Gly Gly Gly Ala Phe Leu
65                  70                  75                  80 ata ccg tat ttt att ttc ctg ttt ggg agt ggc ctg cct gtg ttt ttc        288
Ile Pro Tyr Phe Ile Phe Leu Phe Gly Ser Gly Leu Pro Val Phe Phe
                85                  90                  95 ctg gag gtc ata ata ggc cag tac acc tca gaa ggg gga atc acc tgc        336
Leu Glu Val Ile Ile Gly Gln Tyr Thr Ser Glu Gly Gly Ile Thr Cys
                100                 105                 110 tgg gag aag atc tgc ccc ttg ttc tct ggc att ggc tac gca tcc atc        384
Trp Glu Lys Ile Cys Pro Leu Phe Ser Gly Ile Gly Tyr Ala Ser Ile
            115                 120                 125 gtc atc gtg tcc ctc ctg aat gtg tac tac att gtc atc ctg gcc tgg        432
Val Ile Val Ser Leu Leu Asn Val Tyr Tyr Ile Val Ile Leu Ala Trp
    130                 135                 140 gcc aca tac tac cta ttt cac tcc ttc cag aca gag ctt ccc tgg gcc        480
Ala Thr Tyr Tyr Leu Phe His Ser Phe Gln Thr Glu Leu Pro Trp Ala
145                 150                 155                 160 cac tgc aac cac agc tgg aac aca cca cat tgc atg gag gac acc ctg        528
His Cys Asn His Ser Trp Asn Thr Pro His Cys Met Glu Asp Thr Leu
                165                 170                 175 cgt agg aat gag agt ctc tgg gtc tcc ctt agc gcc tcc aac ttc acc        576
Arg Arg Asn Glu Ser Leu Trp Val Ser Leu Ser Ala Ser Asn Phe Thr
                180                 185                 190 tcg cct gtc atc gag ttc tgg gag cgc aat gta ctc agc ctg tct tcc        624
Ser Pro Val Ile Glu Phe Trp Glu Arg Asn Val Leu Ser Leu Ser Ser
            195                 200                 205 gga atc gac gaa cca ggc gct ctg aaa tgg gac ctt gcg ctc tgc ctc        672
Gly Ile Asp Glu Pro Gly Ala Leu Lys Trp Asp Leu Ala Leu Cys Leu
    210                 215                 220 ctc tta gtc tgg ctt gtc tgt ttt ttc tgc ata tgg aag ggt gtt cga        720
Leu Leu Val Trp Leu Val Cys Phe Phe Cys Ile Trp Lys Gly Val Arg
225                 230                 235                 240 tcc aca ggc aag gtt gtc tac ttc acc gcc act ttc ccg ttt gcc atg        768
Ser Thr Gly Lys Val Val Tyr Phe Thr Ala Thr Phe Pro Phe Ala Met
                245                 250                 255 ctt ctg gtg ctg ctg gtc cgt gga ctg acc ctg ccg gga gct ggc gaa        816
Leu Leu Val Leu Leu Val Arg Gly Leu Thr Leu Pro Gly Ala Gly Glu
                260                 265                 270 ggc atc aaa ttc tac ctg tac cct gac atc agc cgc ctt gag gac cca        864
Gly Ile Lys Phe Tyr Leu Tyr Pro Asp Ile Ser Arg Leu Glu Asp Pro
            275                 280                 285
```

```
cag gtg tgg atc gac gcc gga acc cag ata ttc ttt tcc tat gcc atc    912
Gln Val Trp Ile Asp Ala Gly Thr Gln Ile Phe Phe Ser Tyr Ala Ile
    290             295             300 tgc ctg ggg gcc atg acc tca ctg gga agc tac aac aag tac aag tat    960
Cys Leu Gly Ala Met Thr Ser Leu Gly Ser Tyr Asn Lys Tyr Lys Tyr
305             310             315             320 aac tcg tac agg gac tgt atg ctg ctg gga tgc ctg aac agt ggt acc   1008
Asn Ser Tyr Arg Asp Cys Met Leu Leu Gly Cys Leu Asn Ser Gly Thr
            325             330             335 agt ttt gtg tct ggc ttc gca gtt ttt tcc atc ctg ggc ttc atg gca   1056
Ser Phe Val Ser Gly Phe Ala Val Phe Ser Ile Leu Gly Phe Met Ala
        340             345             350 caa gag caa ggg gtg gac att gct gat gtg gct gag tca ggt cct ggc   1104
Gln Glu Gln Gly Val Asp Ile Ala Asp Val Ala Glu Ser Gly Pro Gly
            355             360             365 ttg gcc ttc att gcc tat cca aaa gct gtg act atg atg ccg ctg ccc   1152
Leu Ala Phe Ile Ala Tyr Pro Lys Ala Val Thr Met Met Pro Leu Pro
370             375             380 acc ttt tgg tcc att ctg ttt ttt att atg ctc ctc ttg ctt gga ctg   1200
Thr Phe Trp Ser Ile Leu Phe Phe Ile Met Leu Leu Leu Leu Gly Leu
385             390             395             400 gac agc cag ttt gtt gaa gtc gaa gga cag atc aca tcc ttg gtt gat   1248
Asp Ser Gln Phe Val Glu Val Glu Gly Gln Ile Thr Ser Leu Val Asp
            405             410             415 ctt tac ccg tcc ttc cta agg aag ggt tat cgt cgg gaa gtc ttc atc   1296
Leu Tyr Pro Ser Phe Leu Arg Lys Gly Tyr Arg Arg Glu Val Phe Ile
        420             425             430 gcc atc ctg tgt agc atc agc tac ctg ctg ggg ctg tcg atg gtg acg   1344
Ala Ile Leu Cys Ser Ile Ser Tyr Leu Leu Gly Leu Ser Met Val Thr
            435             440             445 gag ggt ggc atg tat gtg ttt caa ctc ttt gac tac tat gca gct agt   1392
Glu Gly Gly Met Tyr Val Phe Gln Leu Phe Asp Tyr Tyr Ala Ala Ser
450             455             460 ggt gta tgc ctt ttg tgg gtt gca ttc ttt gaa tgt ttt gtt att gcc   1440
Gly Val Cys Leu Leu Trp Val Ala Phe Phe Glu Cys Phe Val Ile Ala
465             470             475             480 tgg ata tat ggt ggt gat aac tta tat gac ggt att gag gac atg att   1488
Trp Ile Tyr Gly Gly Asp Asn Leu Tyr Asp Gly Ile Glu Asp Met Ile
            485             490             495 ggc tat cgg cct ggg ccc tgg atg aag tac agc tgg gct gtc atc act   1536
Gly Tyr Arg Pro Gly Pro Trp Met Lys Tyr Ser Trp Ala Val Ile Thr
        500             505             510 cca gtt ctc tgt gct gga tgt ttc atc ttc tct ctt gtc aag tat gta   1584
Pro Val Leu Cys Ala Gly Cys Phe Ile Phe Ser Leu Val Lys Tyr Val
            515             520             525 ccc ctg acc tac aac aaa gtc tac gtg tat cct gat tgg gca att ggg   1632
Pro Leu Thr Tyr Asn Lys Val Tyr Val Tyr Pro Asp Trp Ala Ile Gly
530             535             540 ctg ggc tgg ggc ctg gcc cta tcc tcc atg gtg tgt atc ccc ttg gtc   1680
Leu Gly Trp Gly Leu Ala Leu Ser Ser Met Val Cys Ile Pro Leu Val
545             550             555             560 att gcc atc ctc ctc tgc cgg acg gag gga ccg ttc cgc gtg aga atc   1728
Ile Ala Ile Leu Leu Cys Arg Thr Glu Gly Pro Phe Arg Val Arg Ile
            565             570             575 caa tac ctg ata acc ccc agg gag ccc aac cgc tgg gct gtg gag cgt   1776
Gln Tyr Leu Ile Thr Pro Arg Glu Pro Asn Arg Trp Ala Val Glu Arg
        580             585             590 gag ggg gcc aca ccc ttc cac tcc cgc aca agc ctc gtc atg aac ggc   1824
Glu Gly Ala Thr Pro Phe His Ser Arg Thr Ser Leu Val Met Asn Gly
```

```
                    595                 600                 605
        gca ctc atg aaa ccc agt cac gtc att gtg gag acc atg atg tga           1869
        Ala Leu Met Lys Pro Ser His Val Ile Val Glu Thr Met Met
            610                 615                 620
```

<210> SEQ ID NO 8
<211> LENGTH: 622
<212> TYPE: PRT
<213> ORGANISM: Cricetulus griseus

<400> SEQUENCE: 8

```
Met Ala Thr Lys Glu Lys Leu Gln Cys Leu Lys Asp Phe His Lys Asp
1               5                   10                  15

Ile Leu Lys Pro Ser Pro Gly Lys Ser Pro Gly Thr Arg Pro Glu Asp
            20                  25                  30

Glu Ala Glu Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Gly Ala Phe Leu
65                  70                  75                  80

Ile Pro Tyr Phe Ile Phe Leu Phe Gly Ser Gly Leu Pro Val Phe Phe
                85                  90                  95

Leu Glu Val Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Ile
        115                 120                 125

Val Ile Val Ser Leu Leu Asn Val Tyr Tyr Ile Val Ile Leu Ala Trp
    130                 135                 140

Ala Thr Tyr Tyr Leu Phe His Ser Phe Gln Thr Glu Leu Pro Trp Ala
145                 150                 155                 160

His Cys Asn His Ser Trp Asn Thr Pro His Cys Met Glu Asp Thr Leu
                165                 170                 175

Arg Arg Asn Glu Ser Leu Trp Val Ser Leu Ser Ala Ser Asn Phe Thr
            180                 185                 190

Ser Pro Val Ile Glu Phe Trp Glu Arg Asn Val Leu Ser Leu Ser Ser
        195                 200                 205

Gly Ile Asp Glu Pro Gly Ala Leu Lys Trp Asp Leu Ala Leu Cys Leu
    210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Glu
            260                 265                 270

Gly Ile Lys Phe Tyr Leu Tyr Pro Asp Ile Ser Arg Leu Glu Asp Pro
        275                 280                 285

Gln Val Trp Ile Asp Ala Gly Thr Gln Ile Phe Phe Ser Tyr Ala Ile
    290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Val Phe Ser Ile Leu Gly Phe Met Ala
            340                 345                 350
```

```
Gln Glu Gln Gly Val Asp Ile Ala Asp Val Ala Glu Ser Gly Pro Gly
            355                 360                 365

Leu Ala Phe Ile Ala Tyr Pro Lys Ala Val Thr Met Met Pro Leu Pro
        370                 375                 380

Thr Phe Trp Ser Ile Leu Phe Phe Ile Met Leu Leu Leu Gly Leu
385                 390                 395                 400

Asp Ser Gln Phe Val Glu Val Glu Gly Gln Ile Thr Ser Leu Val Asp
                405                 410                 415

Leu Tyr Pro Ser Phe Leu Arg Lys Gly Tyr Arg Arg Glu Val Phe Ile
            420                 425                 430

Ala Ile Leu Cys Ser Ile Ser Tyr Leu Leu Gly Leu Ser Met Val Thr
        435                 440                 445

Glu Gly Gly Met Tyr Val Phe Gln Leu Phe Asp Tyr Tyr Ala Ala Ser
    450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
            500                 505                 510

Pro Val Leu Cys Ala Gly Cys Phe Ile Phe Ser Leu Val Lys Tyr Val
        515                 520                 525

Pro Leu Thr Tyr Asn Lys Val Tyr Val Tyr Pro Asp Trp Ala Ile Gly
    530                 535                 540

Leu Gly Trp Gly Leu Ala Leu Ser Ser Met Val Cys Ile Pro Leu Val
545                 550                 555                 560

Ile Ala Ile Leu Leu Cys Arg Thr Glu Gly Pro Phe Arg Val Arg Ile
                565                 570                 575

Gln Tyr Leu Ile Thr Pro Arg Glu Pro Asn Arg Trp Ala Val Glu Arg
            580                 585                 590

Glu Gly Ala Thr Pro Phe His Ser Arg Thr Ser Leu Val Met Asn Gly
        595                 600                 605

Ala Leu Met Lys Pro Ser His Val Ile Val Glu Thr Met Met
    610                 615                 620

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 10

His His His His His His His His His His
1               5                   10
```

<210> SEQ ID NO 11
<211> LENGTH: 911
<212> TYPE: PRT
<213> ORGANISM: Homo sapiens

<400> SEQUENCE: 11

Met Glu Glu Leu Gln Asp Asp Tyr Glu Asp Met Met Glu Glu Asn Leu
1               5                   10                  15

Glu Gln Glu Glu Tyr Glu Asp Pro Asp Ile Pro Glu Ser Gln Met Glu
            20                  25                  30

Glu Pro Ala Ala His Asp Thr Glu Ala Thr Ala Thr Asp Tyr His Thr
        35                  40                  45

Thr Ser His Pro Gly Thr His Lys Val Tyr Val Glu Leu Gln Glu Leu
    50                  55                  60

Val Met Asp Glu Lys Asn Gln Glu Leu Arg Trp Met Glu Ala Ala Arg
65                  70                  75                  80

Trp Val Gln Leu Glu Glu Asn Arg Gly Glu Asn Gly Ala Trp Gly Arg
                85                  90                  95

Pro His Leu Ser His Leu Thr Phe Trp Ser Leu Leu Glu Leu Arg Arg
            100                 105                 110

Val Phe Thr Lys Gly Thr Val Leu Leu Asp Leu Gln Glu Thr Ser Leu
        115                 120                 125

Ala Gly Val Ala Asn Gln Leu Leu Asp Arg Phe Ile Phe Glu Asp Gln
    130                 135                 140

Ile Arg Pro Gln Asp Arg Glu Glu Leu Leu Arg Ala Leu Leu Leu Lys
145                 150                 155                 160

His Ser His Ala Gly Glu Leu Glu Ala Leu Gly Gly Val Lys Pro Ala
                165                 170                 175

Val Leu Thr Arg Ser Gly Asp Pro Ser Gln Pro Leu Leu Pro Gln His
            180                 185                 190

Ser Ser Leu Glu Thr Gln Leu Phe Cys Glu Gln Gly Asp Gly Gly Thr
        195                 200                 205

Glu Gly His Ser Pro Ser Gly Ile Leu Glu Lys Ile Pro Pro Asp Ser
    210                 215                 220

Glu Ala Thr Leu Val Leu Val Gly Arg Ala Asp Phe Leu Glu Gln Pro
225                 230                 235                 240

Val Leu Gly Phe Val Arg Leu Gln Glu Ala Ala Glu Leu Glu Ala Val
                245                 250                 255

Glu Leu Pro Val Pro Ile Arg Phe Leu Phe Val Leu Leu Gly Pro Glu
            260                 265                 270

Ala Pro His Ile Asp Tyr Thr Gln Leu Gly Arg Ala Ala Ala Thr Leu
        275                 280                 285

Met Ser Glu Arg Val Phe Arg Ile Asp Ala Tyr Met Ala Gln Ser Arg
    290                 295                 300

Gly Glu Leu Leu His Ser Leu Glu Gly Phe Leu Asp Cys Ser Leu Val
305                 310                 315                 320

Leu Pro Pro Thr Asp Ala Pro Ser Glu Gln Ala Leu Leu Ser Leu Val
                325                 330                 335

Pro Val Gln Arg Glu Leu Leu Arg Arg Arg Tyr Gln Ser Ser Pro Ala
            340                 345                 350

Lys Pro Asp Ser Ser Phe Tyr Lys Gly Leu Asp Leu Asn Gly Gly Pro
        355                 360                 365

Asp Asp Pro Leu Gln Gln Thr Gly Gln Leu Phe Gly Gly Leu Val Arg

```
            370                 375                 380
Asp Ile Arg Arg Arg Tyr Pro Tyr Tyr Leu Ser Asp Ile Thr Asp Ala
385                 390                 395                 400

Phe Ser Pro Gln Val Leu Ala Ala Val Ile Phe Ile Tyr Phe Ala Ala
                405                 410                 415

Leu Ser Pro Ala Ile Thr Phe Gly Gly Leu Leu Gly Glu Lys Thr Arg
                420                 425                 430

Asn Gln Met Gly Val Ser Glu Leu Leu Ile Ser Thr Ala Val Gln Gly
            435                 440                 445

Ile Leu Phe Ala Leu Leu Gly Ala Gln Pro Leu Leu Val Val Gly Phe
        450                 455                 460

Ser Gly Pro Leu Leu Val Phe Glu Glu Ala Phe Ser Phe Cys Glu
465                 470                 475                 480

Thr Asn Gly Leu Glu Tyr Ile Val Gly Arg Val Trp Ile Gly Phe Trp
                485                 490                 495

Leu Ile Leu Leu Val Val Leu Val Val Ala Phe Glu Gly Ser Phe Leu
            500                 505                 510

Val Arg Phe Ile Ser Arg Tyr Thr Gln Glu Ile Phe Ser Phe Leu Ile
        515                 520                 525

Ser Leu Ile Phe Ile Tyr Glu Thr Phe Ser Lys Leu Ile Lys Ile Phe
    530                 535                 540

Gln Asp His Pro Leu Gln Lys Thr Tyr Asn Tyr Asn Val Leu Met Val
545                 550                 555                 560

Pro Lys Pro Gln Gly Pro Leu Pro Asn Thr Ala Leu Leu Ser Leu Val
                565                 570                 575

Leu Met Ala Gly Thr Phe Phe Phe Ala Met Met Leu Arg Lys Phe Lys
            580                 585                 590

Asn Ser Ser Tyr Phe Pro Gly Lys Leu Arg Arg Val Ile Gly Asp Phe
        595                 600                 605

Gly Val Pro Ile Ser Ile Leu Ile Met Val Leu Val Asp Phe Phe Ile
    610                 615                 620

Gln Asp Thr Tyr Thr Gln Lys Leu Ser Val Pro Asp Gly Phe Lys Val
625                 630                 635                 640

Ser Asn Ser Ser Ala Arg Gly Trp Val Ile His Pro Leu Gly Leu Arg
                645                 650                 655

Ser Glu Phe Pro Ile Trp Met Met Phe Ala Ser Ala Leu Pro Ala Leu
            660                 665                 670

Leu Val Phe Ile Leu Ile Phe Leu Glu Ser Gln Ile Thr Thr Leu Ile
        675                 680                 685

Val Ser Lys Pro Gly Arg Lys Met Val Lys Gly Ser Gly Phe His Leu
    690                 695                 700

Asp Leu Leu Leu Val Val Gly Met Gly Gly Val Ala Ala Leu Phe Gly
705                 710                 715                 720

Met Pro Trp Leu Ser Ala Thr Thr Val Arg Ser Ala Thr His Ala Asn
                725                 730                 735

Ala Leu Thr Val Met Gly Lys Ala Ser Thr Pro Gly Ala Ala Ala Gln
            740                 745                 750

Ile Gln Glu Val Lys Glu Gln Arg Ile Ser Gly Leu Leu Val Ala Val
        755                 760                 765

Leu Val Gly Leu Ser Ile Leu Met Glu Pro Ile Leu Ser Arg Ile Pro
    770                 775                 780

Leu Ala Val Leu Phe Gly Ile Phe Leu Tyr Met Gly Val Thr Ser Leu
785                 790                 795                 800
```

-continued

```
Ser Gly Ile Gln Leu Phe Asp Arg Ile Leu Leu Phe Lys Pro Pro
                805                 810                 815

Lys Tyr His Pro Asp Val Pro Tyr Val Lys Arg Val Lys Thr Trp Arg
            820                 825                 830

Met Tyr Leu Phe Thr Gly Ile Gln Ile Ile Cys Leu Ala Val Leu Trp
        835                 840                 845

Val Val Lys Ser Thr Pro Ala Ser Leu Ala Leu Pro Phe Val Leu Ile
        850                 855                 860

Leu Thr Val Pro Leu Arg Arg Val Leu Leu Pro Leu Ile Phe Arg Asn
865                 870                 875                 880

Val Glu Leu Gln Cys Leu Asp Ala Asp Ala Lys Ala Thr Phe Asp
                885                 890                 895

Glu Glu Glu Gly Arg Asp Glu Tyr Asp Glu Val Ala Met Pro Val
            900                 905                 910
```

METHOD FOR PRODUCING A POLYPEPTIDE USING A CELL THAT OVEREXPRESSES A BICARBONATE TRANSPORTER

CROSS-REFERENCE TO RELATED APPLICATIONS

This application is a National Stage application of PCT/JP2008/069184, filed Oct. 23, 2008, which claims priority from Japanese application JP 2007-276182, filed Oct. 24, 2007.

TECHNICAL FIELD

The present invention relates to a cell to be used in the production of heteroproteins and a production method using the cell. In more detail, the present invention relates to a cell that strongly expresses a bicarbonate transporter and a method for producing a polypeptide using the cell.

BACKGROUND ART

When proteins useful as pharmaceuticals are produced with the recombinant DNA technique, use of animal cells enables complicated post-translational modification and folding which prokaryotic cells can not perform. Therefore, animal cells are frequently used as host cells for producing recombinant proteins.

Recently, a large number of biopharmaceuticals, such as antibodies and physiologically active proteins, have been developed. Techniques that permit efficient production of recombinant proteins by animal cells lead to cost reduction of biopharmaceuticals and promise their stable supply to patients.

Under these circumstances, a method of protein production with higher production efficiency is desired.

An anion exchanger is a transporter that mediates antiport of intracellular and extracellular anions across a plasma membrane (membrane transport protein). An SLC4 family is a family of $HCO_3^-$ transporters, and three members belonging to the SLC4 family, namely AE1, AE2, and AE3, have a function to exchange $Cl^-$ outside a plasma membrane for $HCO_3^-$ inside a plasma membrane.

In a kidney, AE1 is found in a intercalated cells in collecting ducts in the basolateral membrane (Non-Patent Document 1). It has been known that mutations in human AE1 cause distal renal tubular acidosis (Non-Patent Documents 2 and 3).

Further, in a kidney, three isoforms of AE2, namely AE2a, AE2b, and AE2c, have been found. AE2 is considered to regulate intracellular pH homeostasis for cell signal transduction (Non-Patent Document 4). However, an AE2 knockout mouse that dies during the weaning period has been found to suffer no renal phenotypic abnormalities (Non-Patent Document 5).

An SLC26 is a relatively new anion exchanger family, and it has been suggested that a large number of its members (for example, SLC26A3, SLC26A4, SLC26A6, and SLC26A9) are bicarbonate exchangers (Non-Patent Documents 6 to 11).

On the other hand, it has been absolutely unknown that by strongly expressing an anion exchanger having a bicarbonate transporter function, uptake of anions into a cultured cell and excretion of anions to the outside of the cell, as mediated by the anion exchanger, can be artificially promoted, which contributes to improvement in the production of a desired recombinant protein in the cultured cell.

[Non-Patent Document 1]
van Adelsberg J S. et. al., J Biol Chem 1993; 268:11283-11289
[Non-Patent Document 2]
Shayakui C. et. al., Curr Opin Nephrol Hypertens 2000; 9:541-546
[Non-Patent Document 3]
Alper S L. et. al., Annu Rev Physiol 2002; 64:899-923
[Non-Patent Document 4]
Komlosi P. et. al., Am J Physiol Renal Physiol 2005; 288:F380-F386
[Non-Patent Document 5]
Gawenis L R. et. al., J Biol Chem 2004; 279:30531-30539
[Non-Patent Document 6]
Melvin et al, J Biol Chem 1999; 274:22855-22861
[Non-Patent Document 7]
Ko et al., EMBO J. 2002; 21:5662-5672
[Non-Patent Document 8]
Soleimani et al., Am. J. Physiol. Renal Physiol. 2001; 280:F356-F364
[Non-Patent Document 9]
Wang et al., Am. J. Physiol. Gastrointest. Liver Physiol. 2002; 282:G573-G579
[Non-Patent Document 10]
Petrovic et al., Am. J. Physiol. Renal Physiol. 2004; 286:F161-F169
[Non-Patent Document 11]
Xu et al., Am. J. Physiol. Cell Physiol. 2005; 289:C493-C505

DISCLOSURE OF THE INVENTION

Problem for Solution by the Invention

It is an object of the present invention to provide a method which is capable of producing a polypeptide efficiently.

Means to Solve the Problem

As a result of extensive and intensive researches toward the solution of the above problem, the present inventors have found that it is possible to increase the yield of a desired polypeptide by using a cell that strongly expresses a bicarbonate transporter. Thus, the present invention has been achieved. Moreover, the desired polypeptide could be produced in an even greater amount by using cells capable of co-expressing a bicarbonate transporter and cysteine sulfinic acid decarboxylase (hereinafter sometimes referred to as "CSAD") or alanine aminotransferase (hereinafter sometimes referred to as "ALT").

The present invention may be summarized as follows.
(1) A method of producing a polypeptide, comprising culturing a cell which strongly expresses a bicarbonate transporter and has a transferred DNA encoding a desired polypeptide and thereby allowing the cell to produce said polypeptide.
(2) The method of (1) above, wherein the cell which strongly expresses a bicarbonate transporter is a cell into which a DNA encoding the bicarbonate transporter has been transferred.
(3) The production method of (1) or (2) above, wherein the cell that strongly expresses a bicarbonate transporter further expresses cysteine sulfinic acid decarboxylase or alanine aminotransferase strongly.
(4) The production method of any one of (1)-(3) above, wherein the bicarbonate transporter is an SLC4 anion exchanger or SLC26 anion exchanger.
(5) The production method of any one of (1)-(3) above, wherein the bicarbonate transporter is an SLC4 anion exchanger.

(6) The production method of (5) above, wherein the SLC4 anion exchanger is AE1.

(7) The method of any one of (1)-(6) above, wherein the cell is Chinese hamster ovary cells.

(8) The method of any one of (1)-(7) above, wherein the desired polypeptide is an antibody.

(9) The method of any one of (4)-(6) above, wherein the DNA encoding the SLC4 anion exchanger is any one of the following (a) to (e):

(a) a DNA encoding a polypeptide having the amino acid sequence as shown in SEQ ID NO: 2;

(b) a DNA encoding a polypeptide which has an amino acid sequence derived from the amino acid sequence as shown in SEQ ID NO: 2 by substitution, deletion, addition and/or insertion of one or more amino acid residues and yet has SLC4 anion exchanger activity;

(c) a DNA encoding a polypeptide having 50% or more amino acid sequence homology with the amino acid sequence as shown in SEQ ID NO: 2 and yet having SLC4 anion exchanger activity;

(d) a DNA having the nucleotide sequence as shown in SEQ ID NO: 1;

(e) a DNA which hybridizes to a DNA complementary to a DNA having the nucleotide sequence as shown in SEQ ID NO: 1 under stringent conditions and yet encodes a polypeptide having SLC4 anion exchanger activity.

(10) A method of preparing a pharmaceutical containing a polypeptide prepared by the method of any one of (1)-(9) above.

(11) A cell which has a transferred DNA encoding a bicarbonate transporter and a transferred DNA encoding a desired polypeptide.

(12) The cell according to (11) above, which further has a transferred DNA encoding cysteine sulfinic acid decarboxylase or alanine aminotransferase.

(13) A cell which has a transferred DNA encoding a bicarbonate transporter and a transferred DNA encoding cysteine sulfinic acid decarboxylase or alanine aminotransferase.

Effect of the Invention

According to the present invention, it has become possible to produce a desired polypeptide in high yield.

The present specification encompasses the contents disclosed in the specification and/or the drawings of Japanese Patent Application No. 2007-276182 based on which the present patent application claims priority.

The survival rates on day 7 of the culture were also characterized by P<0.01 (data not shown).

Figure 7:
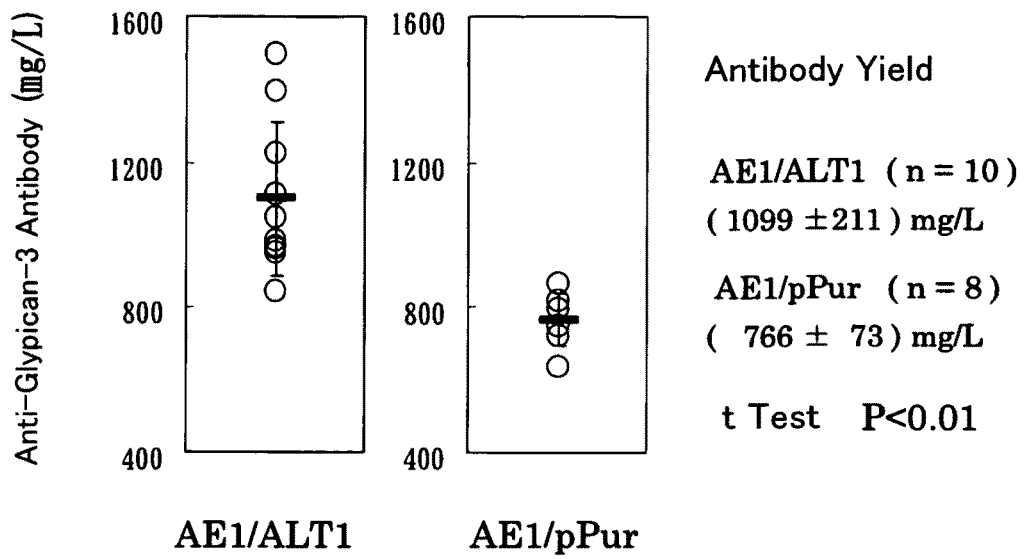

FIG. 7 is a plot of the amount of anti-glypican-3 antibody production on day of 8 fed-batch culture in a 50-mL shaker flask. The amount of an anti-glypican-3 antibody produced by an AE1/ALT co-expressing cell strain (n=10) which was obtained by introducing pPur-ALT1 into a pHyg-AE1-42 strain, or a pHyg-AE1-transformed cell capable of high-yield antibody production, was greater than that produced by an AE1/CSAD strain (n=9), and further, the amount of the anti-glypican-3 antibody produced by an AE1/ALT co-expressing cell strain was significantly greater than that produced by AE1/pPur co-expressing cells (n=8) which were obtained by introducing pPur into a pHyg-AE1-42 strain (P<0.01).

Figure 8:
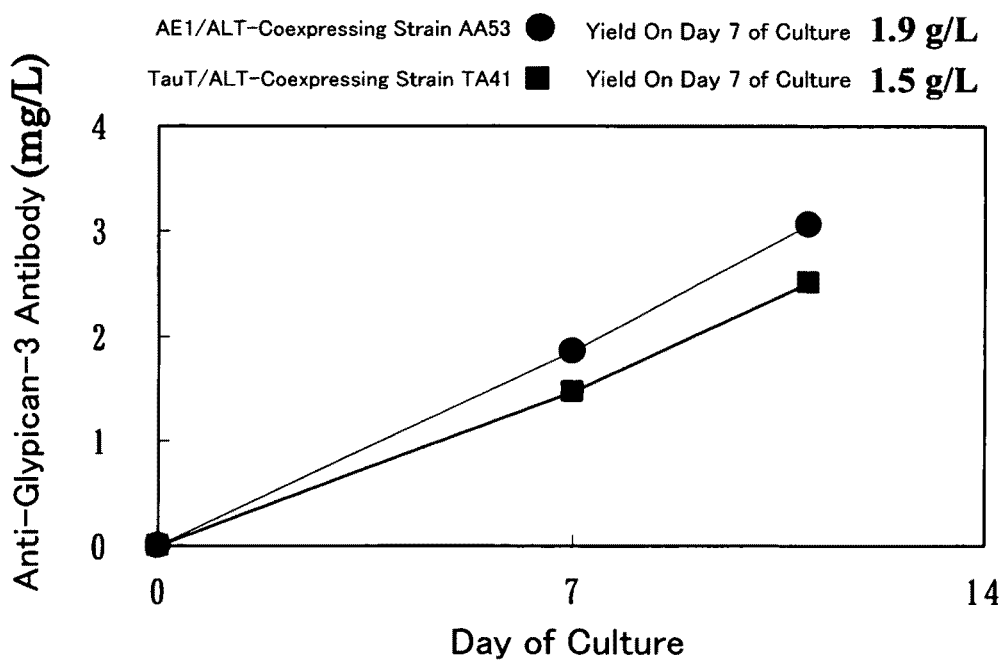

FIG. 8 is a graph showing the amount of an antibody produced by AA53, or an AE1/ALT1 co-expressing strain, during fed-batch culture in a 1 L-jar. The amount of anti-glypican-3 antibody production on day 7 of the culture was 1.9 g/L.

Figures 9, 10:
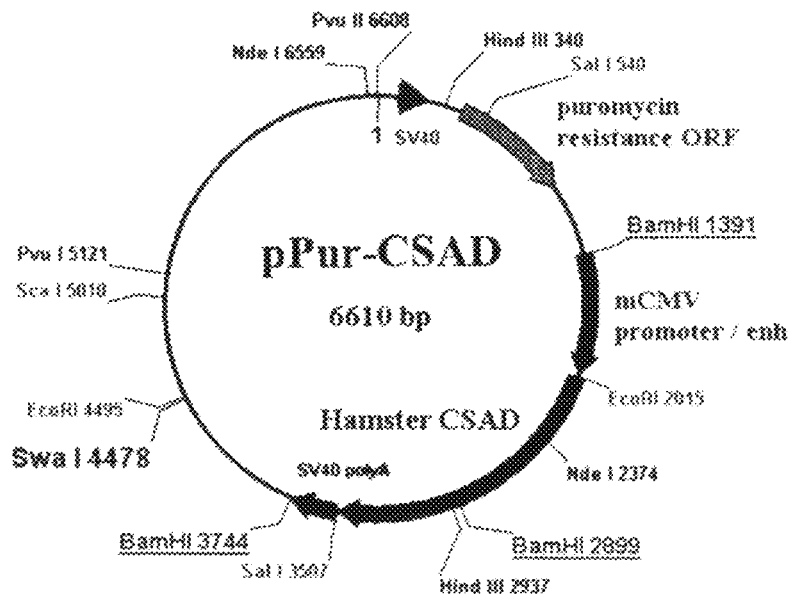

FIG. 9 shows the nucleotide sequence (SEQ ID NO: 3) of a newly cloned, CHO cell-derived hamster CSAD gene and the amino acid sequence (SEQ ID NO: 4) deduced therefrom.

FIG. 10 shows a plasmid for Puromycin selection which was used for expressing hamster CSAD (493 amino acids).

Figure 11:
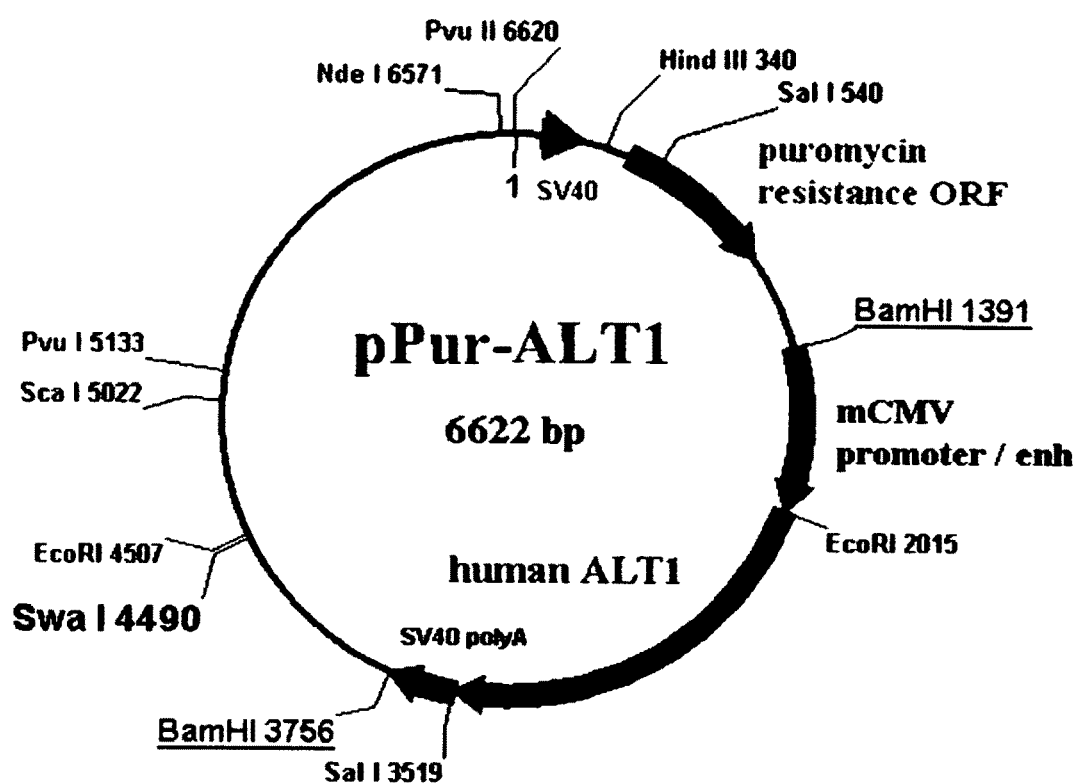

FIG. 11 shows a plasmid for Puromycin selection which was used for expressing human ALT1 (496 amino acids).

Figures 12, 13:
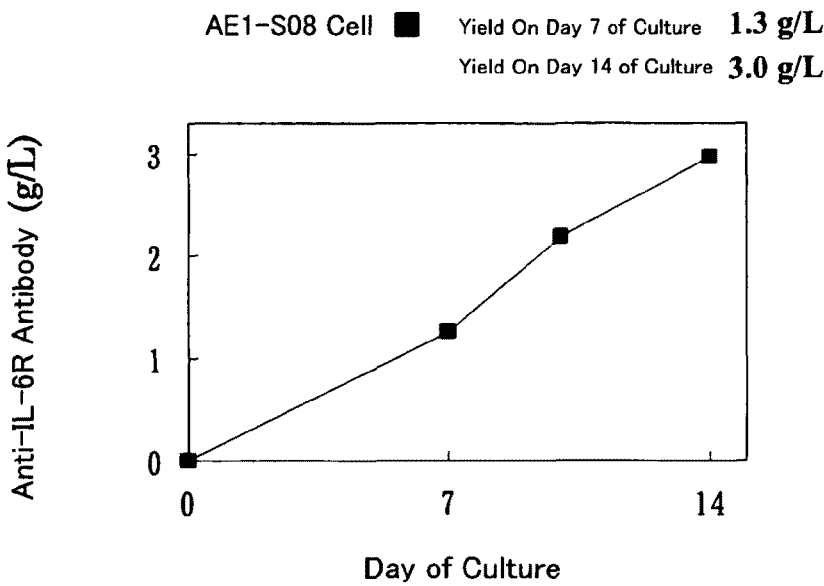

FIG. 12 is a graph showing the amount of an antibody produced by an anti IL-6R antibody producing AE1-S08 cell derived from an AE1 strongly expressing host during fed-batch culture in a 1 L-jar. The amount of anti-IL-6R antibody production on day 14 of the culture was 3.0 g/L.

FIG. 13 shows the nucleotide sequence (SEQ ID NO: 7) of a newly cloned, CHO cell-derived hamster taurine transporter gene and the amino acid sequence (SEQ ID NO: 8) deduced therefrom.

Figure 5:
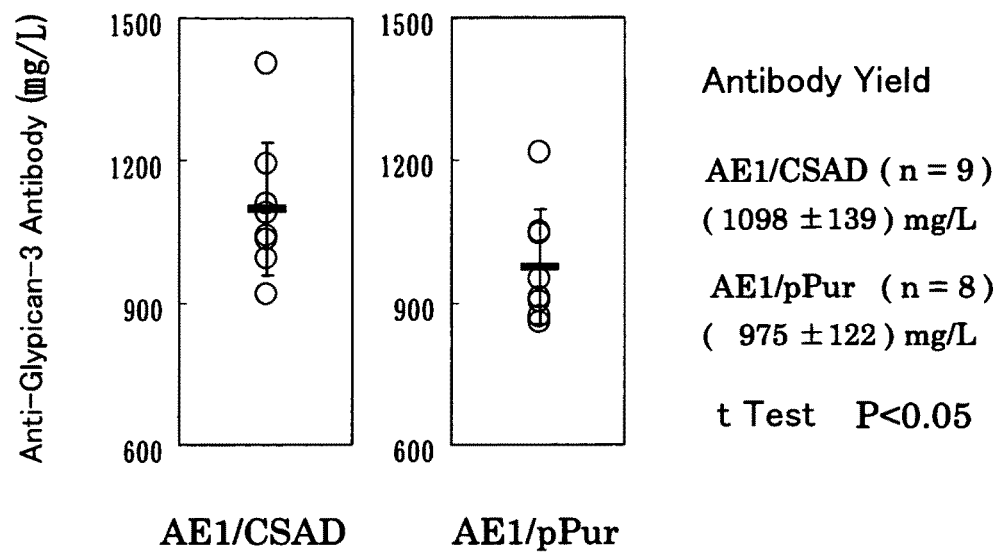
FIG. 5 is a plot of the amount of anti-glypican-3 antibody production on day 10 of fed-batch culture in a 50-mL shaker flask. The amount of an anti-glypican-3 antibody produced by an AE1/CSAD co-expressing cell strain (n=9) which was obtained by introducing pPur-CSAD into a pHyg-AE1-42 strain, or a pHyg-AE1-transformed cell capable of high-yield antibody production, was significantly greater than that produced by AE1/pPur co-expressing cells (n=8) which were obtained by introducing pPur into a pHyg-AE1-42 strain (P<0.05).
Figure 14:
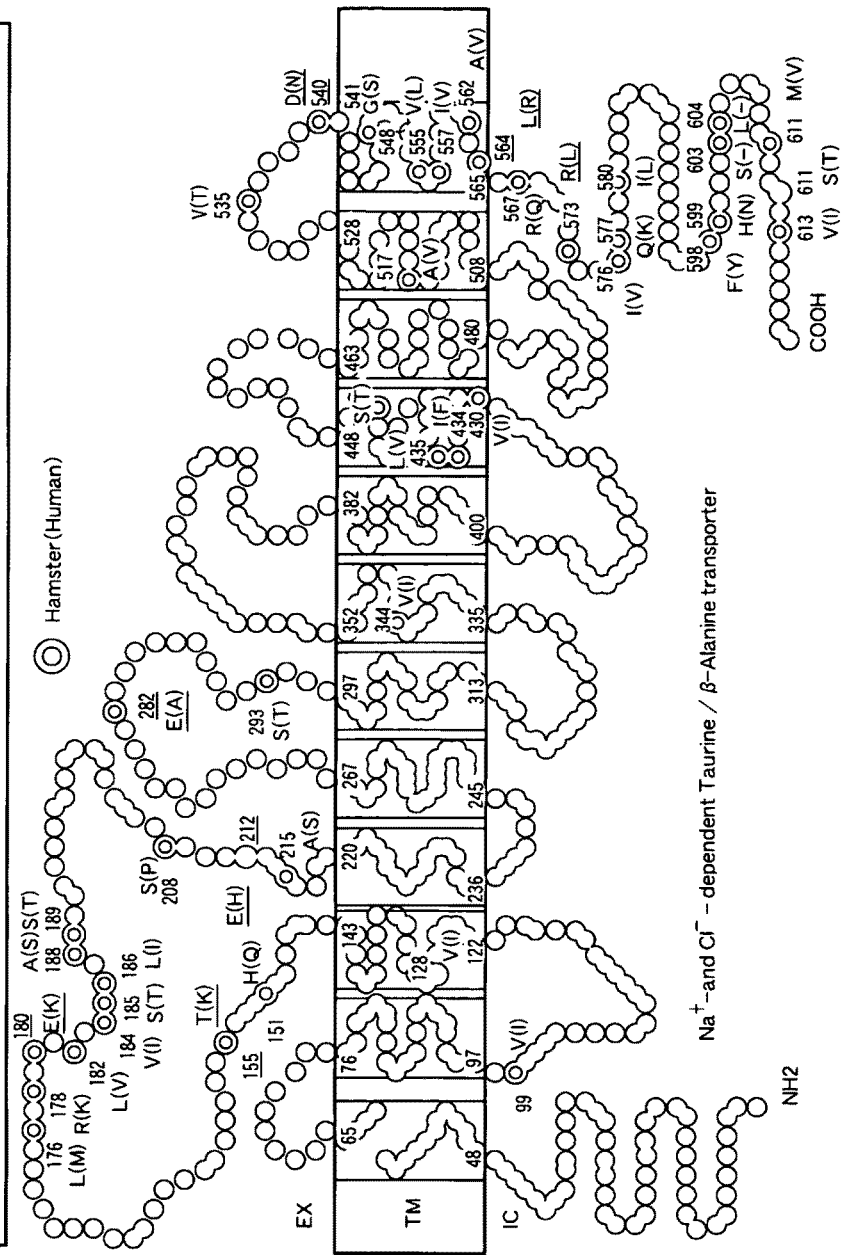

FIG. 14 is a taurine transporter membrane topology which was created based on the transmembrane regions and orientations predicted by TMpred program from the amino acid sequence of a newly cloned, CHO cell-derived hamster TauT with reference to FIG. 5 of Shinichi Uchida et al., Proc. Natl. Acad. Sci. USA Vol. 89, pp. 8230-8234, September 1992. Mark ⊚ indicates hamster TauT specific amino acid residues. A large number of amino acid residues different from those in human TauT are present in the 2nd loop (EX: extra-cell membrane region), the 12th transmembrane region (TM) and the C-terminal (IC: intracellular region).

FIG. 15 shows a plasmid for Hygromycin-selection, which was used for expressing hamster TauT (622 amino acids).

BEST MODE FOR CARRYING OUT THE INVENTION

Hereinbelow, embodiments of the present invention will be described in more detail.

The present invention provides a method of producing a polypeptide, comprising culturing a cell which strongly expresses a bicarbonate transporter and has a transferred DNA encoding a desired polypeptide and thereby allowing the cell to produce the polypeptide.

In the method of the present invention, the cell may be either a natural cell capable of producing the desired polypeptide or a transformed cell into which a DNA encoding the desired polypeptide has been transferred. Preferably, a transformed cell into which a DNA encoding the desired polypeptide has been transferred is used.

In the method of the present invention, the desired polypeptide is not particularly limited. The polypeptide may be any polypeptide such as an antibody (e.g., anti-IL-6 receptor antibody, anti-glypican-3 antibody, anti-CD3 antibody, anti-CD20 antibody, anti-GPIIb/IIIa antibody, anti-TNF antibody, anti-CD25 antibody, anti-EGFR antibody, anti-Her2/neu antibody, anti-RSV antibody, anti-CD33 antibody, anti-CD52 antibody, anti-IgE antibody, anti-CD11a antibody, anti-VEGF antibody, anti-VLA4 antibody, and the like) or a physiologically active protein (e.g., granulocyte-colony stimulating factor (G-CSF), granulocyte macrophage-colony stimulating factor (GM-CSF), erythropoietin, interferon, interleukin such as IL-1 or IL-6, t-PA, urokinase, serum albumin, blood coagulation factor, PTH, and the like). An antibody is particularly preferred, and may be any antibody such as a natural antibody, a low molecular sized antibody (e.g., Fab, scFv, sc(Fv)2), a chimeric antibody, a humanized antibody, etc.

By using strongly a bicarbonate transporter expressing cells, the amount of a polypeptide produced by cells can be increased.

A bicarbonate transporter is a membrane protein that has an antiport function, by which bicarbonate anions ($HCO_3^-$) or carbonate anions ($CO_3^{2-}$) are excreted whereas chloride anions and sulfate anions are taken up. A bicarbonate transporter may be exemplified by an SLC4 anion exchanger and an SLC26 anion exchanger.

An SLC4 anion exchanger is a membrane protein that regulates intracellular pH homeostasis and cell volume. At present, 10 kinds (SLC4A1 (AE1), SLC4A2 (AE2), SLC4A3 (AE3), SLC4A4 (NBCe1), SLC4A5 (NBCe2), SLC4A7 (NBCn1), SLC4A8 (kNBC3), SLC4A9 (NBCn2), SLC4A10 (NBCn3), and SLC4A11 (NaBC1)) of SLC4 families are known, and at least one kind of isoform exists. These SLC4 anion exchangers have different functions; for example, SLC4A1 (AE1), SLC4A2 (AE2), ALC4A3 (AE3), and ALC4A9 (NBCn2 or AE4) are non-$Na^+$-dependent, electrically-neutral exchangers for $Cl^-$ and $HCO_3^-$, ALC4A4 (NBCe1) and ALC4A5 (NBCe2) are electrogenic, ALC4A7 (NBCn1) is an electrically-neutral cotransporter for $Na^+$ and $HCO_3^-$, ALC4A8 (kNBC3) and ALC4A10 (NBCn3) are $Na^+$-dependent, electrically-neutral exchangers for $Cl^-$ and $HCO_3^-$ and ALC4A11 (NaBC1) is an electrogenic cotransporter for $Na^+$ and borate. The above SLC4 anion exchangers have a site-specific action. For example, in a case of AE1, AE1 present in polar epithelial cells contributes to transepithelial secretion and resorption of acids and bases whereas AE1 present in erythrocytes of trout promotes osmolyte transport.

The SLC4 anion exchanger may be exemplified by SLC4A1 (AE1), SLC4A2 (AE2), SLC4A3 (AE3), SLC4A4 (NBCe1), SLC4A5 (NBCe2), SLC4A7 (NBCn1), SLC4A8 (kNBC3), SLC4A9 (NBCn2), SLC4A10 (NBCn3), and SLC4A11 (NaBC1), among which AE1 is preferable.

An SLC26 anion exchanger is a multifunctional membrane protein that acts in almost all organ systems. For the SLC26 anion exchanger, one that mediates antiport of sulfate anions, iodide anions, formate anions, oxalate anions, chloride anions, hydroxyl anions, bicarbonate anions and the like, and a chloride ion channel, or an anion-dependent molecular motor exist. The SLC26 anion exchanger is considered to be involved in homeostasis of various anions and 10 kinds (SLC26A1, SLC26A2, SLC26A3, SLC26A4, SLC26A5, SLC26A6, SLC26A7, SLC26A8, SLC26A9, and SLC26A11) of anion exchanger families have been known. For example, SLC26A3, SLC26A4, SLC26A6 and SLC26A9, which are transporters for hydroxyl anions and bicarbonate anions regulate pH inside as well as outside a membrane in a similar manner to an SLC4 anion exchanger. SLC26A1, SLC26A2, SLC26A4, SLC26A6, SLC26A9 and SLC26A11 are expressed in a kidney. SLC26A1 transports sulfate anions and oxalate anions whereas SLC26A6 mediates antiport of various anions in order to take up sodium chloride. SLC26A1, SLC26A4 and SLC26A6 and SLC26A5 become causative factors for nephrolithiasis, hypertension, and hearing loss, respectively. SLC26A7 is involved in acid-base homeostasis and blood pressure control in a similar manner to SLC26A4. The SLC26 anion exchanger may be exemplified by SLC26A1, SLC26A2, SLC26A3, SLC26A4, SLC26A5, SLC26A6, SLC26A7, SLC26A8, SLC26A9, and SLC26A11.

A cell which strongly expresses a bicarbonate transporter is not particularly limited as long as the cell has an increased expression level of a bicarbonate transporter compared to a corresponding natural cell. The natural cell is not particularly limited. A cell which is used as a host in the production of a recombinant protein (e.g., CHO cells) may be used.

A bicarbonate transporter to be strongly expressed in a cell may be derived from any organism and no particular limitation is imposed thereon. Specifically, the bicarbonate transporter may be derived from organisms including a human, rodents such as a mouse, a rat, and a hamster, mammals such as a chimpanzee, a cow, a horse, a dog, and a wolf, birds such as a chicken, fishes such as a zebrafish and an eel, and insects such as *Drosophila*; the bicarbonate transporter is preferably derived from a human, rodents, or the same species as the host cell. For example, in a case where the cell in which a bicarbonate transporter is to be strongly expressed is a Chinese hamster ovary cell (CHO cell), the bicarbonate transporter is preferably derived from a human or a hamster.

The cell which strongly expresses a bicarbonate transporter may be any cell, for example, eukaryotic cell such as animal, plant and yeast cells, prokaryotic cell such as *E. coli* and *B. subtilis*, etc. Preferably, animal cells such as CHO and COS cells are used, CHO cells are particularly preferred. In order to prepare a desired polypeptide, cells suitable for transfer of a gene encoding the desired polypeptide such as CHO-dhfr-cells are preferred.

As a cell which strongly expresses a bicarbonate transporter, a cell into which a bicarbonate transporter gene (e.g., SLC4 anion exchanger gene, SLC26 anion exchanger gene, etc.) has been artificially transferred may be given. A cell into which a bicarbonate transporter gene has been artificially transferred can be prepared by methods known to those skilled in the art. For example, such a cell may be prepared by incorporating a bicarbonate transporter into a vector and transforming the vector into a cell. Furthermore, the concept of "cells into which a bicarbonate transporter gene has been artificially transferred" encompasses herein cells in which an endogenous bicarbonate transporter gene has been activated by gene activation technology (see, for example, International Publication WO94/12650) so that the bicarbonate transporter is strongly expressed.

As an SLC4 anion exchanger gene to be transferred in a cell, any one of the following DNAs (a) to (e) encoding an SLC4 anion exchanger may be used.

(a) a DNA encoding a polypeptide having the amino acid sequence as shown in SEQ ID NO: 2;

(b) a DNA encoding a polypeptide which has an amino acid sequence derived from the amino acid sequence as shown in SEQ ID NO: 2 by substitution, deletion, addition and/or insertion of one or more amino acid residues and yet has SLC4 anion exchanger activity;

(c) a DNA encoding a polypeptide having 50% or more amino acid sequence homology with the amino acid sequence as shown in SEQ ID NO: 2 and yet having SLC4 anion exchanger activity;

(d) a DNA having the nucleotide sequence as shown in SEQ ID NO: 1;

(e) a DNA which hybridizes to a DNA complementary to a DNA having the nucleotide sequence as shown in SEQ ID NO: 1 under stringent conditions and yet encodes a polypeptide having SLC4 anion exchanger activity.

The concept of an SLC4 anion exchanger activity encompasses an activity to take up $Cl^-$ and $SO_4^{2-}$ present in the medium and excrete intracellular $HCO_3^-$ and borate in order to maintain intracellular pH homeostasis and cell volume.

The SLC4 anion exchanger activity can be measured as follows.

Cells in which SLC4 is functionally expressed are treated with BCECF-AM which is a pH-sensitive dye. Then, fluorescent intensity is compared between cells that have been perfused with a medium containing $CF^-$ and $Na^+$ and cells that have been perfused with a medium free of $Cl^-$ and $Na^+$, whereby changes in intracellular pH (pHi) can be measured (Dahl N K. et. al., J Biol Chem 2003; 278:44949-44958; Fujinaga J. et. al., J Biol Chem 1999; 274:6626-6633).

In the present invention, a DNA encoding a polypeptide having the amino acid sequence of SEQ ID NO: 2 is advantageously used as a DNA encoding an SLC4 anion exchanger. Besides that, a DNA encoding a polypeptide having the amino acid sequence of SEQ ID NO: 2 in which one or a plurality (for example, several) of amino acid(s) is/are substituted, deleted, added, and/or inserted, and also having an SLC4 anion exchanger activity may be used. The amino acid sequence of SEQ ID NO: 2 is an amino acid sequence of human AE1. Aside from the sequence information of human AE1, the counterpart information about a mouse, a rat, a chimpanzee, a cow, a horse, a dog, a wolf, a chicken, a zebrafish, and the like has been registered as mouse; GenBank NM_011403, rat; GeneBank NM_012651, chimpanzee; GenBank XM_001151353, cow; GeneBank NM_181036, horse; GeneBank NM_001081788, dog; GenBank AB242566, wolf; GeneBank NM_001048031, chicken; GenBank NM_205522, and zebrafish; GenBank NM_198338. Thus, AE1 as described above can also be used. Other SLC4 anion exchangers can also be used since the sequence information thereof has been registered in various databases.

The polypeptide which has an amino acid sequence derived from the amino acid sequence as shown in SEQ ID NO: 2 by substitution, deletion, addition and/or insertion of one or more amino acid residues and yet has SLC4 anion exchanger activity is functionally equivalent to an SLC4 anion exchanger derived from human, mouse, rat, chimpanzee, cow, horse, dog, wolf, chicken or zebrafish (hereinafter sometimes referred to as "SLC4 anion exchanger derived from human or the like"). Such a polypeptide encompasses, for example, mutants of the SLC4 anion exchanger derived from human or the like. In Example described below, a mutant in which four out of 911 amino acids were replaced (L88R, E693G, V732A and H834Y) was used.

As methods well-known to those skilled in the art for preparing polypeptides functionally equivalent to a specific polypeptide, methods of introducing mutations into polypeptides may be given. For example, those skilled in the art could prepare polypeptides functionally equivalent to the SLC4 anion exchanger derived from human or the like by appropriately introducing mutations into amino acids of the SLC4 anion exchanger derived from human or the like by site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc Natl Acad Sci USA. 82, 488-492; Kunkel (1988) Methods Enzymol. 85, 2763-2766). Mutations in amino acids may also occur in nature.

Specific examples of polypeptides functionally equivalent to the SLC4 anion exchanger derived from human or the like include, but are not limited to, a polypeptide having an amino acid sequence derived from the amino acid sequence (e.g., SEQ ID NOS: 2) of the SLC4 anion exchanger derived from human or the like by deletion of one or more amino acids, preferably 1-30 amino acids, more preferably 1-10 amino acids; a polypeptide having an amino acid sequence derived from the amino acid sequence of the SLC4 anion exchanger derived from human or the like by addition of one or more amino acids, preferably 1-30 amino acids, more preferably 1-10 amino acids; and a polypeptide having an amino acid sequence derived from the amino acid sequence of the SLC4 anion exchanger derived from human or the like by substitution of one or more amino acids, preferably 1-30 amino acids, more preferably 1-10 amino acids, with other amino acids.

Amino acid residues to be mutated are not particularly limited. Preferably, amino acid residues are mutated to other amino acids in which the nature of the initial amino acid side chain is conserved. Specific examples of the nature of amino acid side chain include hydrophobic amino acids (A, I, L, M, F, P, W, Y and V), hydrophilic amino acids (R, D, N, C, E, Q, C, H, K, S and T), amino acids with an aliphatic side chain (G; A, V, L, I and P), amino acids with a hydroxyl group-containing side chain (S, T and Y), amino acids with a sulfur atom-containing side chain (C and M), amino acids with a carboxylic acid and amide-containing side chain (D, N, E and Q), amino acids with a base-containing side chain (R, K and H) and amino acids with an aromatic-containing side chain (H, F, Y and W) (In parentheses are one-letter codes for amino acids).

It has been reported that a polypeptide having an amino acid sequence derived from an original amino acid sequence by modification (such as deletion, addition and/or substitution of one or more amino acids) maintains the biological activity of the original polypeptide (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G et al., Proc. Natl. Acad. Sci. USA (1982) 79, 6409-6413).

As one example of the polypeptide in which one or more amino acid residues are added to the SLC4 anion exchanger derived from human or the like, a fusion polypeptide comprising the SLC4 anion exchanger derived from human or the like may be given. Such a fusion polypeptide is composed of the SLC4 anion exchanger derived from human or the like and other polypeptide fused thereto. Such a fusion polypeptide may be prepared by linking a gene encoding the SLC4 anion exchanger derived from human or the like in frame with a gene encoding the other polypeptide, transferring the resultant DNA into an expression vector and expressing the DNA in a host cell. Techniques known to those skilled in the art may be used. There is no limitation on the polypeptide to be fused to the SLC4 anion exchanger derived from human or the like.

Examples of polypeptides to be fused to the SLC4 anion exchanger derived from human or the like include, but are not limited to, FLAG (Hopp, T. P. et al., BioTechnology (1988) 6, 1204-1210), 6×His comprising six histidine (His) residues (SEQ ID NO: 9), 10×His (SEQ ID NO: 10), influenza hemagglutinin (HA), human c-myc fragment, VSV-GP fragment, p18HIV fragment, T7-tag, HSV-tag, E-tag, SV40T antigen fragment, 1ck tag, α-tubulin fragment, B-tag, protein C fragment, glutathione-S-transferase (GST), influenza hemagglutinin (HA), immunoglobulin constant region, β-galactosidase and maltose-binding protein (MBP).

A commercially available gene encoding such polypeptide is fused to the gene encoding the SLC4 anion exchanger derived from human or the like. The fused gene thus prepared is expressed to prepare a fused polypeptide.

An alternative method known to those skilled in the art for preparing polypeptides functionally equivalent to a specific polypeptide is a method using the hybridization technique (Sambrook, J et al., Molecular Cloning 2nd ed., 9.47-9.58, Cold Spring Harbor Lab. Press, 1989). Those skilled in the art could routinely isolate a DNA highly homologous to the DNA sequence (e.g., SEQ ID NOS: 1) of the SLC4 anion exchanger derived from human or the like based on that DNA sequence or a part thereof, and isolate polypeptides functionally equivalent to the SLC4 anion exchanger derived from human or the like from that DNA.

Hybridization conditions for isolating a DNA encoding a polypeptide functionally equivalent to the SLC4 anion exchanger derived from human or the like can be appropriately selected by those skilled in the art. For example, low stringent hybridization conditions may be given. Low stringent hybridization conditions are, for example, 42° C., 2×SSC and 0.1% SDS, preferably 50° C., 2×SSC and 0.1% SDS. More preferably, high stringent conditions may be given. For example, high stringent conditions are 65° C., 2×SSC and 0.1% SDS. Under these conditions, as the hybridization temperature is lowered, not only DNAs with high homology but also DNAs with only low homology are obtained. Conversely, it is expected that only those DNAs with high homology are obtained as the hybridization temperature is elevated. However, not only the temperature but also a plurality of factors (such as salt concentrations) affect the stringency of hybridization. Those skilled in the art could appropriately select these factors to realize similar stringency.

The polypeptide encoded by a DNA isolated by these hybridization techniques may have 70% or more homology and usually has high homology with the SLC4 anion exchanger derived from human or the like in the amino acid sequence. The term "high homology" refers to usually 97% or more homology, preferably 98% or more homology, more preferably 99% or more homology. For determination of the homology of polypeptides, the algorithm described in Wilbur, W. J. and Lipman, D. J., Proc. Natl. Acad. Sci. USA (1983) 80, 726-730 may be followed.

The polypeptide may vary in amino acid sequence, molecular weight, isoelectric point, presence or absence of sugar chains, morphology, etc. depending on the cell or host that produce the polypeptide or the purification method that will be described later. However, as long as the resultant polypeptide has functions equivalent to the functions of the SLC4 anion exchanger derived from human or the like, a DNA encoding the polypeptide can be used in the present invention. For example, when the polypeptide of the present invention is expressed in a prokaryote (e.g., Escherichia coli), a methionine reside is added to the N-terminus of the initial amino acid sequence of the polypeptide. When the polypeptide is expressed in a eukaryote (e.g., a mammalian cell), the N-terminal signal sequence is removed. These polypeptides can be used in the present invention.

In the present invention, as a DNA encoding an SLC4 anion exchanger, a DNA having the nucleotide sequence as shown in SEQ ID NO: 1 may be used. Alternatively, a DNA which hybridizes to a DNA complementary to a DNA having the nucleotide sequence as shown in SEQ ID NO: 1 under stringent conditions and yet encodes a polypeptide having SLC4 anion exchanger activity, may be used. SEQ ID NO. 1 shows the nucleotide sequence of human AE1. Aside from the sequence information of human AE1, the counterpart information about a mouse, a rat, a chimpanzee, a cow, a horse, a dog, a wolf, a chicken, a zebrafish, and the like has been registered as mouse; GenBank NM_011403, rat; GeneBank NM_012651, chimpanzee; GenBank XM_001151353, cow; GeneBank NM_181036, horse; GeneBank NM_001081788, dog; GenBank AB242566, wolf; GeneBank NM_001048031, chicken; GenBank NM_205522, and zebrafish; GenBank NM_198338. Thus, AE1 as described above can also be used. Other SLC4 anion exchangers can also be used since the sequence information thereof has been registered in various databases.

The DNA encoding an SLC4 anion exchanger can be used in the in vivo or in vitro production of a desired polypeptide as described above. Further, the DNA encoding an SLC4 anion exchanger may be used in the creation of a cell which strongly expresses an SLC4 anion exchanger. The DNA encoding an SLC4 anion exchanger may take any form as long as it is capable of encoding an SLC4 anion exchanger. That is, the DNA may be, for example, a cDNA synthesized from mRNA, a genomic DNA or a chemically synthesized DNA. It should be noted that, as long as the DNA is capable of encoding an SLC4 anion exchanger, the DNA may have any nucleotide sequence based on the degeneracy of genetic codes.

The DNA encoding an SLC4 anion exchanger may be prepared by methods known to those skilled in the art. For example, the DNA may be prepared by preparing a cDNA library from a cell expressing an SLC4 anion exchanger and performing hybridization using a part of the DNA sequence of an SLC4 anion exchanger (e.g., SEQ ID NO: 1) as a probe. The cDNA library may be prepared, for example, by the method described in Sambrook, J. et al., Molecular Cloning, Cold Spring Harbor Laboratory Press (1989). Alternatively, a commercial cDNA library may be used. It is also possible to prepare the DNA encoding an SLC4 anion exchanger by preparing RNA from a cell expressing an SLC4 anion exchanger, synthesizing oligo DNA molecules based on the DNA sequence of an SLC4 anion exchanger (e.g., SEQ ID NO: 1), and performing PCR using the oligo DNA molecules as primers to thereby amplify a cDNA encoding an SLC4 anion exchanger.

Further, by determining the nucleotide sequence of the resultant cDNA, it is possible to determine the translation region encoding an SLC4 anion exchanger and to obtain the amino acid sequence of the SLC4 anion exchanger. Further, by screening a genomic library using the resultant cDNA as a probe, it is possible to isolate a genomic DNA.

Specifically, the following procedures may be used. First, mRNA is isolated from cells, tissues or the like expressing an SLC4 anion exchanger. For the isolation of mRNA, the total RNA is prepared by known methods, for example, the guanidine ultracentrifugation method (Chirgwin, J. M. et al., Biochemistry (1979) 18, 5294-5299), the AGPC method (Chomczynski, P. and Sacchi, N., Anal. Biochem. (1987) 162, 156-159) or the like, and then mRNA is purified from the total RNA using mRNA Purification Kit (Pharmacia), etc. Alternatively, mRNA may be prepared directly using QuickPrep mRNA Purification Kit (Pharmacia).

From the resultant mRNA, cDNA is synthesized using a reverse transcriptase. Alternatively, cDNA may be synthesized using a kit such as AMV Reverse Transcriptase First-Strand cDNA Synthesis Kit (SEIKAGAKU CORPORATION). It is also possible to synthesize and amplify cDNA according to the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) using 5'-Ampli FINDER RACE Kit (Clontech) and polymerase chain reaction (PCR) with primers.

A DNA fragment of interest is prepared from the resultant PCR product and ligated to a vector DNA to thereby prepare a recombinant vector. The vector is introduced into a host (e.g., E. coli), followed by selection of resultant colonies to thereby obtain a desired recombinant vector. The nucleotide sequence of the DNA of interest may be confirmed by a known method such as the dideoxynucleotide chain termination method.

Further, a nucleotide sequence of higher expression efficiency can be designed for the DNA encoding an SLC4 anion exchanger by considering the frequency of codon usage in the host to be used for expression (Grantham, R. et al., Nucleic Acids Research (1981) 9, p. 43-74). Further, the DNA encoding an SLC4 anion exchanger can be modified using commercially available kits or known methods. Examples of such modifications include, but are not limited to, digestion with restriction enzymes, insertion of synthetic oligonucleotides or appropriate DNA fragments, addition of linkers, and insertion of an initiation codon (ATG) and/or a termination codon (TAA, TGA or TAG).

The DNA encoding an SLC4 anion exchanger also includes a DNA which hybridizes to a DNA having the nucleotide sequence as shown in SEQ ID NO: 1 under stringent conditions and encodes a polypeptide functionally equivalent to an SLC4 anion exchanger.

Stringent conditions can be appropriately selected by those skilled in the art, including, for example, low stringent conditions. Low stringent conditions refer to, for example, 42° C., 2×SSC and 0.1% SDS, preferably 50° C., 2×SSC and 0.1% SDS. More preferably, high stringent conditions may be selected. High stringent conditions refer to, for example, 65° C., 2×SSC and 0.1% SDS. Under these conditions, as the hybridization temperature is elevated, DNAs with a higher homology can be obtained. The above-described DNA which hybridizes is preferably a DNA derived from nature, e.g., cDNA or chromosomal DNA.

These DNAs isolated by hybridization techniques usually have a high nucleotide sequence identity with a DNA encoding the SLC4 anion exchanger derived from human or the like. The DNA encoding an SLC4 anion exchanger also includes a DNA which encodes a polypeptide functionally equivalent to the SLC4 anion exchanger derived from human or the like and has high identity with a DNA encoding the SLC4 anion exchanger derived from human or the like. The term "high identity" refers to usually 96% or more homology, preferably 98% or more homology, more preferably 99% or more identity. The identity of nucleotide sequences may be determined by algorithm BLAST (Karlin and Altschul, Proc. Natl. Acad. Sci. USA 90:5873-5877, 1993). Based on this algorithm, programs such as BLASTN and BLASTX have been developed (Altschul et al. J. Mol. Biol. 215:403-410, 1990). When nucleotide sequences are analyzed by BLASTN based on BLAST, parameters may be set as score=100 and wordlength=12, for example. Specific procedures for these analysis methods are known (.nlm.nih.gov.).

A bicarbonate transporter gene to be incorporated into a cell may be an SLC26 anion exchanger gene. Information of a nucleotide sequence of an SLC26 anion exchanger gene and an amino acid encoded by the gene has been registered as GenBank AF331525 (human putative SLC26A9), GenBank NM_052934 (human SLC26A9 variant 1), GenBank NM_134325 (human SLC26A9 variant 2), GenBank NM_134420(mouse SLC26A6), GenBank NM_177243 (mouse SLC26A9), GenBank AY240025 (Drosophila Slc26d9702), GenBank AY240023 (Drosophila Slc26d6928), GenBank AY240022 (Drosophila Slc26d6125), GenBank AY240021 (Drosophila Slc26d5002), and GenBank AB084425 (eel Slc26A6). Thus, the SLC26 anion exchanger gene described as above can be used.

The DNA encoding an SLC4 anion exchanger may be inserted into a vector.

When the host cell to be used is E. coli, it is preferable that the vector has a replication origin ("ori") so that the vector is largely amplified in E. coli (e.g., JM109, DH5α, HB101 and XL1-Blue) and prepared in large quantity, and also genes for selecting transformed E. coli (e.g., drug resistance genes that enable discrimination of transformant with some drugs such as ampicillin, tetracycline, kanamycin or chloramphenicol). Examples of preferable vectors include, but are not limited to, M13 vectors, pUC vectors, pBR322, pBluescript and pCR-Script. In addition to these vectors, pGEM-T, pDIRECT, pT7, etc. may be enumerated when the vector is used for the purpose of subcloning a cDNA and cutting off the subcloned cDNA. When the vector is used for the purpose of producing the polypeptide of the present invention, an expression vector is especially useful. When expression in E. coli is intended, the expression vector preferably has the above-described features so that the vector is amplified in E. coli, and it also preferably has a promoter which allows efficient expression in E. coli such as JM109, DH5α, HB101 or XL1-Blue, e.g., lacZ promoter (Ward et al, Nature (1989) 341, 544-546; FASEB J. (1992) 6, 2422-2427), araB promoter (Better et al, Science (1988) 240, 1041-1043) or T7 promoter. Specific examples of such vector include, in addition to those listed above, pGEX-5×-1 (Pharmacia), QIAexpress system (Qiagen), pEGFP, or pET (for its host, T7 RNA polymerase-expressing BL21 is preferred).

The vector may comprise signal sequences for polypeptide secretion. When the polypeptide is to be produced in the periplasm of E. coli, pelB signal sequence (Lei, S. P et al., J. Bacteriol. (1987) 169, 4379) may be used as a signal sequence for polypeptide secretion. Introduction of the vector into a host cell may be performed, for example, by the calcium chloride method or electroporation.

In cases where a host cell other than E. coli is used, vectors useful for producing a desired polypeptide include, but are not limited to, mammal-derived expression vectors [e.g., pcDNA3 from Invitrogen; pEGF-BOS (Nucleic Acids. Res. 1990, 18(17), p. 5322); pEF, pCDM8], insect cell-derived expression vectors (e.g., Bac-to-BAC baculovairus expression system from GIBCO BRL; pBacPAK8), plant-derived expression vectors (e.g., pMH1, pMH2), animal virus-derived expression vectors (e.g., pHSV, pMV, pAdexLcw), retrovirus-derived expression vectors (e.g., pZIpneo), yeast-derived expression vectors (e.g., *Pichia* Expression Kit from Invitrogen; pNV11; SP-Q01), and *Bacillus subtilis*-derived expression vectors (e.g., pPL608, pKTH50).

When expression of the polypeptide in animal cells (such as CHO cells, COS cells, NIH3T3 cells, etc.) is intended, the vector preferably has a promoter necessary for expressing the polypeptide in those cells. Examples of such promoter include, but are not limited to, SV40 promoter (Mulligan et al, Nature (1979) 277, 108), MMLV-LTR promoter, EF1α promoter ° (Mizushima et al., Nucleic Acids Res. (1990) 18, 5322) and CMV promoter. More preferably, the vector also has genes for selecting transformed cells (e.g., drug resistance genes that enable discrimination with drugs such as neomycin or G418). Examples of vectors having such properties include, but are not limited to, pMAM, pDR2, pBK-RSV, pBK-CMV, pOPRSV and pOP13.

Further, when stable expression of a gene of interest and intracellular amplification of the copy number of the gene are indented, the following method may be used. Briefly, into CHO cells lacking a nucleic acid synthesis pathway, a vector having DHFR gene that complements the lack (e.g., pCHOI) is introduced, followed by amplification with methotrexate (MTX). On the other hand, when tentative expression of a gene of interest is intended, a method may be used in which COS cells carrying a gene expressing SV40T antigen on the chromosome is transformed with a vector having the replication origin of SV40 (e.g., pcD). As the replication origin, a replication origin derived from polyomavirus, adenovirus or bovine papillomavirus (BPV) may also be used. Further, the expression vector may contain selectable markers for amplifying the copy number of the gene in a host cell system. Examples of such selectable markers include, but are not limited to, aminoglycoside phosphotransferase (APH) gene, thymidine kinase (TK) gene, *E. coli* xanthine-guanine phosphoribosyl transferase (Ecogpt) gene and dihydrofolate reductase (dhfr) gene.

The host cell into which the DNA encoding a bicarbonate transporter (which may be incorporated in a vector) is transferred is not particularly limited. For example, *E. coli* or various animal cells may be used. If a DNA encoding a desired polypeptide is transferred into a host cell into which a DNA encoding a bicarbonate transporter is transferred, this host cell can express the bicarbonate transporter strongly, which leads to an increased production of the desired polypeptide. Into the host cell into which a DNA encoding a bicarbonate transporter is transferred, a DNA encoding CSAD or ALT (which may be incorporated into a vector) may be further transferred. By transferring a DNA encoding a desired polypeptide and a DNA encoding CSAD or ALT into a host cell into which a DNA encoding a bicarbonate transporter is transferred, the yield of the desired polypeptide can be increased. For the production of the polypeptide, there are in vivo and in vitro production systems. Examples of in vitro production systems include systems using eukaryotes and systems using prokaryotes.

When a desired polypeptide is produced using a cell into which a bicarbonate transporter gene has been artificially transferred, the order of the transfer of a bicarbonate transporter gene and the transfer of a gene encoding a desired polypeptide is not particularly limited. A gene encoding a desired polypeptide may be transferred after the transfer of a bicarbonate transporter gene. Alternatively, a bicarbonate transporter gene may be transferred after the transfer of a gene encoding a desired polypeptide. It is also possible to transfer a bicarbonate transporter gene and a gene encoding a desired polypeptide simultaneously.

A bicarbonate transporter gene and a gene encoding a desired polypeptide may be transferred simultaneously in a single vector. Alternatively, they may be transferred separately using a plurality of vectors.

Preferably, the cell which strongly expresses a bicarbonate transporter further expresses cysteine sulfinic acid decarboxylase (CSAD) or alanine aminotransferase (ALT) strongly in order to prepare a desired polypeptide. By transferring a gene encoding the desired polypeptide into the cell and culturing the resultant cell in a medium, the desired polypeptide can be produced in a greater amount.

CSAD is originally known as an enzyme that converts alanine-3-sulfinic acid to hypotaurine. If cysteine sulfinic acid decarboxylase is strongly expressed in a CHO cell, the cell synthesizes an excess amount of β-alanine.

A cell which strongly expresses CSAD is not particularly limited as long as the cell has an increased expression level of CSAD compared to a corresponding natural cell. The natural cell is not particularly limited. A cell which is used as a host in the production of a recombinant protein (e.g., CHO cells) may be used.

As CSAD to be strongly expressed in a cell, CSAD derived from any organism may be used. Specifically, CSAD derived from human, a rodent (such as mouse, rat or hamster), a puffer (such as Tiger puffer) or a sea squirt (such as *Ciona intestnalis*) may be used. Preferably, CSAD derived from human, a rodent or the same species as the host cell may be used. For example, when the cell which is allowed to strongly express CSAD is Chinese hamster ovary cells (CHO cells), the CSAD is preferably derived from human or hamster.

As a cell which strongly expresses CSAD, a cell into which a CSAD gene has been artificially transferred may be given. A cell into which a CSAD gene has been artificially transferred can be prepared by methods known to those skilled in the art. For example, such a cell may be prepared by incorporating a CSAD gene into a vector and transforming the vector into a cell. Furthermore, the concept of "cells into which a CSAD gene has been artificially transferred" encompasses herein cells in which an endogenous CSAD gene has been activated by gene activation technology (see, for example, International Publication WO94/12650) so that CSAD is strongly expressed.

As a CSAD gene to be transferred in a cell, any one of the following DNAs (a1) to (e1) may be used.

(a1) a DNA encoding a polypeptide having the amino acid sequence as shown in SEQ ID NO: 4 or the amino acid sequence of UniProt Knowledgebase (Swiss-Prot and TrEMBL) rat CSAD (Q64611), mouse CSAD_(Q9 DBE0) or human CSAD_(Q9Y600);

(b1) a DNA encoding a polypeptide which has an amino acid sequence derived from the amino acid sequence as shown in SEQ ID NO: 4 or the amino acid sequence of UniProt Knowledgebase (Swiss-Prot and TrEMBL) rat CSAD (Q64611), mouse CSAD_(Q9 DBE0) or human CSAD_(Q9Y600) by substitution, deletion, addition and/or insertion of one or more amino acid residues and yet has CSAD activity;

(c1) a DNA encoding a polypeptide having 70% or more amino acid sequence homology with the amino acid sequence as shown in SEQ ID NO: 4 or the amino acid sequence of UniProt Knowledgebase (Swiss-Prot and TrEMBL) rat CSAD (Q64611), mouse CSAD_(Q9 DBE0) or human CSAD_(Q9Y600) and yet having CSAD activity;

(d1) a DNA having the nucleotide sequence as shown in SEQ ID NO: 3 or the nucleotide sequence of GenBank rat CSAD NM_021750, mouse CSAD NM_144942 or human CSAD NM_015989;

(e1) a DNA which hybridizes to a DNA complementary to a DNA having the nucleotide sequence as shown in SEQ ID NO: 3 or the nucleotide sequence of GenBank rat CSAD NM_021750, mouse CSAD NM_144942 or human CSAD NM_015989 under stringent conditions and yet encodes a polypeptide having CSAD activity.

The concept of a CSAD activity encompasses an activity to catalyze 3-sulfino-L-alanine=hypotaurine+$CO_2$ for decarboxylation. It is also an activity to decarboxylate L-cysteic acid. (EC-Number 4.1.1.29).

The CSAD activity can be measured as follows.
As taught by Davis K. et. al., J Biomed Sci 2001; 8:359-364, $^{14}CO_2$ produced from L-[1-$^{14}C$]cysteic acid by a decarboxylase activity of CSAD is quantitated.

In the present invention, a DNA encoding a polypeptide having the amino acid sequence of SEQ ID NO: 4 or the amino acid sequence of UniProt Knowledgebase (Swiss-Prot and TrEMBL) rat CSAD (Q64611), mouse CSAD_(Q9DBE0) or human CSAD_(Q9Y600) may be used as a DNA encoding CSAD. Besides that, a DNA encoding a polypeptide having the amino acid sequence of SEQ ID NO: 4 or the amino acid sequence of UniProt Knowledgebase (Swiss-Prot and TrEMBL) rat CSAD (Q64611), mouse CSAD_(Q9 DBE0) or human CSAD_(Q9Y600) in which one or a plurality of amino acid(s) is/are substituted, deleted, added, and/or inserted, and also having CSAD activity may be used.

The polypeptide having the amino acid sequence of SEQ ID NO: 4 or the amino acid sequence of UniProt Knowledgebase (Swiss-Prot and TrEMBL) rat CSAD (Q64611), mouse CSAD_(Q9 DBE0) or human CSAD_(Q9Y600) in which one or a plurality of amino acid(s) is/are substituted, deleted, added, and/or inserted, and also having CSAD activity is functionally equivalent to CSAD derived from hamster, rat, mouse or human (hereinafter sometimes referred to as "CSAD derived from hamster or the like). Such a polypeptide encompasses, for example, mutants of CSAD derived from hamster or the like.

As methods well-known to those skilled in the art for preparing polypeptides functionally equivalent to a specific polypeptide, methods of introducing mutations into polypeptides may be given. For example, those skilled in the art could prepare polypeptides functionally equivalent to CSAD derived from hamster or the like by appropriately introducing mutations into amino acids of CSAD derived from hamster or the like by site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc Natl Acad Sci USA. 82, 488-492; Kunkel (1988) Methods Enzymol. 85, 2763-2766). Mutations in amino acids may also occur in nature.

Specific examples of polypeptides functionally equivalent to CSAD derived from hamster or the like include, but are not limited to, a polypeptide having an amino acid sequence derived from the amino acid sequence of CSAD derived from hamster or the like (e.g., the amino acid sequence of SEQ ID NO: 4 or the amino acid sequence of UniProt Knowledgebase (Swiss-Prot and TrEMBL) rat CSAD (Q64611), mouse CSAD_(Q9 DBE0) or human CSAD_(Q9Y600)) by deletion of one or more amino acids, preferably 1-30 amino acids, more preferably 1-10 amino acids; a polypeptide having an amino acid sequence derived from the amino acid sequence of CSAD derived from hamster or the like by addition of one or more amino acids, preferably 1-30 amino acids, more preferably 1-10 amino acids; and a polypeptide having an amino acid sequence derived from the amino acid sequence of CSAD derived from hamster or the like by substitution of one or more amino acids, preferably 1-30 amino acids, more preferably 1-10 amino acids, with other amino acids.

Amino acid residues to be mutated are not particularly limited. Preferably, amino acid residues are mutated to other amino acids in which the nature of the initial amino acid side chain is conserved. Specific examples of the nature of amino acid side chain include hydrophobic amino acids (A, I, L, M, F, P, W, Y and V), hydrophilic amino acids (R, D, N, C, E, Q, C, H, K, S and T), amino acids with an aliphatic side chain (G A, V, L, I and P), amino acids with a hydroxyl group-containing side chain (S, T and Y), amino acids with a sulfur atom-containing side chain (C and M), amino acids with a carboxylic acid and amide-containing side chain (D, N, E and Q), amino acids with a base-containing side chain (R, K and H) and amino acids with an aromatic-containing side chain (H, F, Y and W) (In parentheses are one-letter codes for amino acids).

It has been reported that a polypeptide having an amino acid sequence derived from an original amino acid sequence by modification (such as deletion, addition and/or substitution of one or more amino acids) maintains the biological activity of the original polypeptide (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G et al., Proc. Natl. Acad. Sci. USA (1982) 79, 6409-6413).

As one example of the polypeptide in which one or more amino acid residues are added to CSAD derived from hamster or the like, a fusion polypeptide comprising CSAD derived from hamster or the like may be given. Such a fusion polypeptide is composed of CSAD derived from hamster or the like and other polypeptide fused thereto. Such a fusion polypeptide may be prepared by linking a gene encoding CSAD derived from hamster or the like in frame with a gene encoding the other polypeptide, transferring the resultant DNA into an expression vector and expressing the DNA in a host cell. Techniques known to those skilled in the art may be used. There is no limitation on the polypeptide to be fused to CSAD derived from hamster or the like.

Examples of polypeptides to be fused to CSAD derived from hamster or the like include, but are not limited to, FLAG (Hopp, T. P. et al., BioTechnology (1988) 6, 1204-1210), 6×His comprising six histidine (His) residues (SEQ ID NO: 9), 10×His (SEQ ID NO: 10, influenza hemagglutinin (HA), human c-myc fragment, VSV-GP fragment, p18HIV fragment, T7-tag, HSV-tag, E-tag, SV40T antigen fragment, 1ck tag, α-tubulin fragment, β-tag, protein C fragment, glutathione-S-transferase (GST), influenza hemagglutinin (HA), immunoglobulin constant region, β-galactosidase and maltose-binding protein (MBP).

A commercially available gene encoding such polypeptide is fused to the gene encoding CSAD derived from hamster or the like. The fused gene thus prepared is expressed to prepare a fused polypeptide.

An alternative method known to those skilled in the art for preparing polypeptides functionally equivalent to a specific polypeptide is a method using the hybridization technique (Sambrook, J et al., Molecular Cloning 2nd ed., 9.47-9.58, Cold Spring Harbor Lab. Press, 1989). Those skilled in the art could routinely isolate a DNA highly homologous to the DNA sequence of CSAD derived from hamster or the like (e.g., the DNA sequence of SEQ ID NO: 3 or the DNA sequence of GenBank rat CSAD NM_021750, mouse CSAD NM_144942 or human CSAD NM_015989), based on that DNA sequence or a part thereof, and isolate polypeptides functionally equivalent to CSAD derived from hamster or the like from that DNA.

Hybridization conditions for isolating a DNA encoding a polypeptide functionally equivalent to CSAD derived from hamster or the like can be appropriately selected by those skilled in the art. For example, low stringent hybridization conditions may be given. Low stringent hybridization conditions are, for example, 42° C., 2×SSC and 0.1% SDS, preferably 50° C., 2×SSC and 0.1% SDS. More preferably, high stringent conditions may be given. For example, high stringent conditions are 65° C., 2×SSC and 0.1% SDS. Under these conditions, as the hybridization temperature is lowered, not only DNAs with high homology but also DNAs with only low homology are obtained. Conversely, it is expected that only those DNAs with high homology are obtained as the hybridization temperature is elevated. However, not only the temperature but also a plurality of factors (such as salt concentrations) affect the stringency of hybridization. Those skilled in the art could appropriately select these factors to realize similar stringency.

The polypeptide encoded by a DNA isolated by these hybridization techniques may have 70% or more homology and usually has high homology with CSAD derived from hamster or the like in the amino acid sequence. The term "high homology" refers to usually 97% or more homology, preferably 98% or more homology, more preferably 99% or more homology. For determination of the homology of polypeptides, the algorithm described in Wilbur, W. J. and Lipman, D. J., Proc. Natl. Acad. Sci. USA (1983) 80, 726-730 may be followed.

The polypeptide may vary in amino acid sequence, molecular weight, isoelectric point, presence or absence of sugar chains, morphology, etc. depending on the cell or host that produce the polypeptide or the purification method that will be described later. However, as long as the resultant polypeptide has functions equivalent to the functions of CSAD derived from hamster or the like, a DNA encoding the polypeptide can be used in the present invention. For example, when the polypeptide is expressed in a prokaryote (e.g., *Escherichia coli*), a methionine reside is added to the N-terminus of the initial amino acid sequence of the polypeptide. When the polypeptide is expressed in a eukaryote (e.g., a mammalian cell), the N-terminal signal sequence is removed. A DNA encoding such a polypeptide can be used in the present invention.

In the present invention, a DNA having the nucleotide sequence of SEQ ID NO: 3 or the nucleotide sequences of GenBank rat CSAD NM_021750, mouse CSAD NM_144942, or human CSAD NM_015989 may be used as a DNA that encodes CSAD. Besides that, a DNA encoding a polypeptide hybridizing with a DNA complementary to DNA having the nucleotide sequence of SEQ ID NO: 3 or the nucleotide sequences of GenBank rat CSAD NM_021750, mouse CSAD NM_144942, or human CSAD NM_015989 under a stringent condition, and also having CSAD activity may be used.

The DNA encoding CSAD is used to prepare a cell which strongly expresses CSAD and thereafter used in the in vivo or in vitro production of a desired polypeptide as described above. The DNA encoding CSAD may take any form as long as it is capable of encoding CSAD. That is, the DNA may be, for example, a cDNA synthesized from mRNA, a genomic DNA or a chemically synthesized DNA. It should be noted that, as long as the DNA is capable of encoding CSAD, the DNA may have any nucleotide sequence based on the degeneracy of genetic codes.

The DNA encoding CSAD may be prepared by methods known to those skilled in the art. For example, the DNA may be prepared by preparing a cDNA library from a cell expressing CSAD and performing hybridization using a part of the DNA sequence of CSAD (e.g., the nucleotide sequence of SEQ ID NO: 3 or the nucleotide sequence of GenBank rat CSAD NM_021750, mouse CSAD NM_144942 or human CSAD NM_015989) as a probe. The cDNA library may be prepared, for example, by the method described in Sambrook, J. et al., Molecular Cloning, Cold Spring Harbor Laboratory Press (1989). Alternatively, a commercial cDNA library may be used. It is also possible to prepare the DNA encoding CSAD by preparing RNA from a cell expressing CSAD, synthesizing oligo DNA molecules based on the DNA sequence of CSAD (e.g., the nucleotide sequence of SEQ ID NO: 3 or the nucleotide sequence of GenBank rat CSAD NM_021750, mouse CSAD NM_144942 or human CSAD NM_015989), and performing PCR using the oligo DNA molecules as primers to thereby amplify a cDNA encoding CSAD.

Further, by determining the nucleotide sequence of the resultant cDNA, it is possible to determine the translation region encoding the polypeptide and to obtain the amino acid sequence of CSAD. Further, by screening a genomic library using the resultant cDNA as a probe, it is possible to isolate a genomic DNA.

Specifically, the following procedures may be used. First, mRNA is isolated from cells, tissues or the like expressing CSAD. For the isolation of mRNA, the total RNA is prepared by known methods, for example, the guanidine ultracentrifugation method (Chirgwin, J. M. et al., Biochemistry (1979) 18, 5294-5299), the AGPC method (Chomczynski, P. and Sacchi, N., Anal. Biochem. (1987) 162, 156-159) or the like, and then mRNA is purified from the total RNA using mRNA Purification Kit (Pharmacia), etc. Alternatively, mRNA may be prepared directly using QuickPrep mRNA Purification Kit (Pharmacia).

From the resultant mRNA, cDNA is synthesized using a reverse transcriptase. Alternatively, cDNA may be synthesized using a kit such as AMV Reverse Transcriptase First-Strand cDNA Synthesis Kit (SEIKAGAKU CORPORATION). It is also possible to synthesize and amplify cDNA according to the 5'-RACE method (Frohman, M. A. et al., Proc. Natl. Acad. Sci. USA (1988) 85, 8998-9002; Belyavsky, A. et al., Nucleic Acids Res. (1989) 17, 2919-2932) using 5'-Ampli FINDER RACE Kit (Clontech) and polymerase chain reaction (PCR) with primers.

A DNA fragment of interest is prepared from the resultant PCR product and ligated to a vector DNA to thereby prepare a recombinant vector. The vector is introduced into a host (e.g., *E. coli*), followed by selection of resultant colonies to thereby obtain a desired recombinant vector. The nucleotide sequence of the DNA of interest may be confirmed by a known method such as the dideoxynucleotide chain termination method.

Further, a nucleotide sequence of a higher expression efficiency can be designed for the DNA encoding CSAD by considering the frequency of codon usage in the host to be used for expression (Grantham, R. et al., Nucleic Acids Research (1981) 9, p. 43-74). Further, the DNA encoding CSAD can be modified using commercially available kits or known methods. Examples of such modifications include, but are not limited to, digestion with restriction enzymes, insertion of synthetic oligonucleotides or appropriate DNA fragments, addition of linkers, and insertion of an initiation codon (ATG) and/or a termination codon (TAA, TGA or TAG).

The DNA encoding CSAD also includes a DNA which hybridizes to a DNA complementary to a DNA having the nucleotide sequence as shown in SEQ ID NO: 3 or the nucleotide sequence of GenBank rat CSAD NM_021750, mouse CSAD NM_144942 or human CSAD NM_015989 under stringent conditions and encodes a polypeptide functionally equivalent to CSAD.

Stringent conditions can be appropriately selected by those skilled in the art, including, for example, low stringent conditions. Low stringent conditions refer to, for example, 42° C., 2×SSC and 0.1% SDS, preferably 50° C., 2×SSC and 0.1% SDS. More preferably, high stringent conditions may be selected. High stringent conditions refer to, for example, 65° C., 2×SSC and 0.1% SDS. Under these conditions, as the hybridization temperature is elevated, DNAs with a higher homology can be obtained. The above-described DNA which hybridizes is preferably a DNA derived from nature, e.g., cDNA or chromosomal DNA.

These DNAs isolated by hybridization techniques usually have a high nucleotide sequence identity with a DNA encoding CSAD derived from hamster or the like. The DNA encoding CSAD also includes a DNA which encodes a polypeptide functionally equivalent to CSAD derived from hamster or the like and has high identity with a DNA encoding CSAD derived from hamster or the like. The term "high identity" refers to usually 96% or more homology, preferably 98% or more homology, more preferably 99% or more identity. The identity of nucleotide sequences may be determined by algorithm BLAST (Karlin and Altschul, Proc. Natl. Acad. Sci. USA 90:5873-5877, 1993). Based on this algorithm, programs such as BLASTN and BLASTX have been developed (Altschul et al. J. Mol. Biol. 215:403-410, 1990). When nucleotide sequences are analyzed by BLASTN based on BLAST, parameters may be set as score=100 and wordlength=12, for example. Specific procedures for these analysis methods are known (ncbi.nlm.nih.gov.).

ALT is fundamentally known as an enzyme that produces glutamate by transferring an amino group from alanine to 2-oxoglutarate. If the reaction of biosynthesizing pyruvate and glutamate from alanine could be promoted by strongly expressing ALT in host cells such as CHO cells, the products might be utilized in metabolism during a TCA cycle and glucose production by glycogenesis, and this might improve cell culture behavior, leading to high-yield production of the desired polypeptide.

The strongly ALT expressing cells are not particularly limited as long as they are capable of ALT expression at higher levels than natural cells. Natural cells include, but are not particularly limited to, cells that are used as hosts in the production of recombinant proteins and may be exemplified by CHO cells.

As a cell which strongly expresses ALT, a cell into which an ALT gene has been artificially transferred may be given. A cell into which an ALT gene has been artificially transferred can be prepared by methods known to those skilled in the art. For example, such a cell may be prepared by incorporating an ALT gene into a vector and transforming the vector into a cell. Furthermore, the concept of "cells into which an ALT gene has been artificially transferred" encompasses herein cells in which an endogenous ALT gene has been activated by gene activation technology (see, for example, International Publication WO94/12650) so that ALT is strongly expressed.

As ALT to be strongly expressed in a cell, ALT derived from any organism may be used. Specifically, ALTs derived from human, mouse, rat, dog, African clawed frog, fruit fly, nematode, Japanese rice, *Cyanidioschyzon merolae*, *Saccharomyces cerevisiae*, *Ashbya gossypii*, *Candida albicans*, *Schizosaccharomyces pombe*, *Aspergillus nidulans*, *Aspergillus fumigatus*, *Aspergillus oryzae*, *Cryptococcus neoformans*, *Dictyostelium discoideum*, *Trypanosoma brucei*, *Leishmania major*, *Entamoeba histolytica* and *Trypanosoma cruzi* are known and can be used. Preferably, ALT derived from human, a rodent or the same species as the host cell may be used. For example, when the cell which is allowed to strongly express ALT is Chinese hamster ovary cells (CHO cells), ALT is preferably derived from human or hamster. For ALT in humans, mice, and yeast, variants (ALT1 and ALT2) exist. ALT2 has 80% or greater homology to ALT1 at the amino acid level. ALT1 was forcedly expressed in the Examples and Referential Examples described later.

As an ALT gene to be strongly expressed in a cell, any one of the following DNAs (a2) to (e2) encoding ALT may be used.

(a2) a DNA encoding a polypeptide having the amino acid sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa japonica* (Japanese rice): 4342210, KEGG/ENZYME: 2.6.1.2/*Oryza sativa japonica* (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140;

(b2) a DNA encoding a polypeptide which has an amino acid sequence derived from the amino acid sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila mela-* nogaster (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa japonica* (Japanese rice): 4342210, KEGG/ENZYME: 2.6.1.2/*Oryza sativa japonica* (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430 KEGG/ENZYME: 2.6.1.2/*Trypanosoma cruzi*: 510889.120 or KEGG/ENZYME: 2.6.1.2/*Trypanosoma cruzi*: 510889.140 by substitution, deletion, addition and/or insertion of one or more (e.g., several) amino acid residues and yet has ALT activity;

(c2) a DNA encoding a polypeptide having 70% or more amino acid sequence homology with the amino acid sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa japonica* (Japanese rice): 4342210, KEGG/ENZYME: 2.6.1.2/*Oryza sativa japonica* (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140 and yet having ALT activity;

(d2) a DNA having the nucleotide sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640 KEGG/ENZYME: 2.6.1.2/*Caenorhabditis elegans* (nematode): C32F10.8, KEGG/ENZYME: 2.6.1.2/*Oryza sativa japonica* (Japanese rice): 4342210, KEGG/ENZYME: 2.6.1.2/*Oryza sativa japonica* (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140;

(e2) a DNA which hybridizes to a DNA complementary to a DNA having the nucleotide sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa japonica* (Japanese rice): 4342210, KEGG/ENZYME: 2.6.1.2/*Oryza sativa japonica* (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*:

233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140 under stringent conditions and yet encodes a polypeptide having ALT activity.

The concept of an ALT activity encompasses an enzyme activity to catalyze transfer of an amino group between an amino acid and an α-keto acid.

The ALT activity can be measured as follows.

An ALT activity level is determined by a reagent for automated analyzer for measuring alanine aminotransferase (Runpia liquid S-ALT, approval number 20900AMZ00597000) and the method taught by Rajamohan F. et. al., Protein Expression and Purification (2006) 48, 81-89.

In the present invention, as a gene encoding ALT, a DNA encoding a polypeptide having the amino acid sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa japonica* (Japanese rice): 4342210, KEGG/ENZYME: 2.6.1.2/*Oryza sativa japonica* (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140 may be used. Alternatively, a DNA encoding a polypeptide which has an amino acid sequence derived from the amino acid sequence described above by substitution, deletion, addition and/or insertion of one or more amino acid residues and yet has ALT activity may be used.

The polypeptide which has an amino acid sequence derived from the amino acid sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa japonica* (Japanese rice): 4342210, KEGG/ENZYME: 2.6.1.2/*Oryza sativa japonica* (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140 by substitution, deletion, addition and/or insertion of one or more amino acid residues and yet has ALT activity is functionally equivalent to ALT derived from human, mouse, rat, dog, African clawed frog, fruit fly, nematode, Japanese rice, *Cyanidioschyzon merolae*, *Saccharomyces cerevisiae*, *Ashbya gossypii*, *Candida albicans*, *Schizosaccharomyces pombe*, *Aspergillus nidulans*, *Aspergillus fumigatus*, *Aspergillus oryzae*, *Cryptococcus neoformans*, *Dictyostelium discoideum*, *Trypanosoma brucei*, *Leishmania major*, *Entamoeba histolytica* or *Trypanosoma cruzi* (hereinafter sometimes referred to as "ALT derived from human or the like"). Such a polypeptide encompasses, for example, mutants of ALT derived from human or the like. In Example and Referential Examples described below, a mutant in which four out of 496 amino acids were replaced (R53S, Q72R, F286S and M332K) was used.

As methods well-known to those skilled in the art for preparing polypeptides functionally equivalent to a specific polypeptide, methods of introducing mutations into polypeptides may be given. For example, those skilled in the art could prepare polypeptides functionally equivalent to ALT derived from human or the like by appropriately introducing mutations into amino acids of ALT derived from human or the like by site-directed mutagenesis (Hashimoto-Gotoh, T. et al. (1995) Gene 152, 271-275; Zoller, M J, and Smith, M. (1983) Methods Enzymol. 100, 468-500; Kramer, W et al. (1984) Nucleic Acids Res. 12, 9441-9456; Kramer W, and Fritz H J (1987) Methods. Enzymol. 154, 350-367; Kunkel, T A (1985) Proc Natl Acad Sci USA. 82, 488-492; Kunkel (1988) Methods Enzymol. 85, 2763-2766). Mutations in amino acids may also occur in nature.

Specific examples of polypeptides functionally equivalent to the ALT derived from human or the like include, but are not limited to, a polypeptide having an amino acid sequence derived from the amino acid sequence (e.g., the amino acid sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus*

(mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/ *Drosophila melanogaster* (fruit fly): Dmel_CG1640 KEGG/ ENZYME: 2.6.1.2/*Caenorhabditis elegans* (nematode): C32F10.8, KEGG/ENZYME: 2.6.1.2/*Oryza sativa japonica* (Japanese rice): 4342210, KEGG/ENZYME: 2.6.1.2/*Oryza sativa japonica* (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/ *Dictyostelium discoideum*: DDB_0232139, KEGG/ENZYME: 2.6.1.2/*Trypanosoma brucei*: Tb927.1.3950, KEGG/ ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/ *Trypanosoma cruzi*: 510889.120 or KEGG/ENZYME: 2.6.1.2/*Trypanosoma cruzi*: 510889.140) of the ALT derived from human or the like by deletion of one or more amino acids, preferably 1-30 amino acids, more preferably 1-10 amino acids; a polypeptide having an amino acid sequence derived from the amino acid sequence of the ALT derived from human or the like by addition of one or more amino acids, preferably 1-30 amino acids, more preferably 1-10 amino acids; and a polypeptide having an amino acid sequence derived from the amino acid sequence of the ALT derived from human or the like by substitution of one or more amino acids, preferably 1-30 amino acids, more preferably 1-10 amino acids, with other amino acids.

Amino acid residues to be mutated are not particularly limited. Preferably, amino acid residues are mutated to other amino acids in which the nature of the initial amino acid side chain is conserved. Specific examples of the nature of amino acid side chain include hydrophobic amino acids (A, I, L, M, F, P, W, Y and V), hydrophilic amino acids (R, D, N, C, E, Q, H, K, S and T), amino acids with an aliphatic side chain (G; A, V, L, I and P), amino acids with a hydroxyl group-containing side chain (S, T and Y), amino acids with a sulfur atom-containing side chain (C and M), amino acids with a carboxylic acid and amide-containing side chain (D, N, E and Q), amino acids with a base-containing side chain (R, K and H) and amino acids with an aromatic-containing side chain (H, F, Y and W) (In parentheses are one-letter codes for amino acids).

It has been reported that a polypeptide having an amino acid sequence derived from an original amino acid sequence by modification (such as deletion, addition and/or substitution of one or more amino acids) maintains the biological activity of the original polypeptide (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G et al., Proc. Natl. Acad. Sci. USA (1982) 79, 6409-6413).

As one example of the polypeptide in which one or more amino acid residues are added to the ALT derived from human or the like, a fusion polypeptide comprising the ALT derived from human or the like may be given. Such a fusion polypeptide is composed of the ALT derived from human or the like and other polypeptide fused thereto. Such a fusion polypeptide may be prepared by linking a gene encoding the ALT derived from human or the like in frame with a gene encoding the other polypeptide, transferring the resultant DNA into an expression vector and expressing the DNA in a host cell. Techniques known to those skilled in the art may be used. There is no limitation on the polypeptide to be fused to the ALT derived from human or the like.

Examples of polypeptides to be fused to the ALT derived from human or the like include, but are not limited to, FLAG (Hopp, T. P. et al., BioTechnology (1988) 6, 1204-1210), 6×His comprising six histidine (His) residues (SEQ ID NO: 9), 10×His (SEQ ID NO: 10), influenza hemagglutinin (HA), human c-myc fragment, VSV-GP fragment, p18HIV fragment, T7-tag, HSV-tag, E-tag, SV40T antigen fragment, lck tag, α-tubulin fragment, β-tag, protein C fragment, glutathione-S-transferase (GST), influenza hemagglutinin (HA), immunoglobulin constant region, β-galactosidase and maltose-binding protein (MBP).

A commercially available gene encoding such polypeptide is fused to the gene encoding the ALT derived from human or the like. The fused gene thus prepared is expressed to prepare a fused polypeptide.

An alternative method known to those skilled in the art for preparing polypeptides functionally equivalent to a specific polypeptide is a method using the hybridization technique (Sambrook, J et al., Molecular Cloning 2nd ed., 9.47-9.58, Cold Spring Harbor Lab. Press, 1989). Those skilled in the art could routinely isolate a DNA highly homologous to the DNA sequence (e.g., the DNA sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa* japonica (Japanese rice): 4342210, KEGG/ENZYME: 2.6.1.2/*Oryza sativa japonica* (Japanese rice): 4348524, KEGG/ENZYME: 2.6.1.2/*Cyanidioschyzon merolae: CMM066C*, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/ *Schizosaccharomyces pombe*: SPBC582.08, KEGG/ENZYME: 2.6.1.2/*Aspergillus nidulans*: AN1923.2, KEGG/ ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/ *Dictyostelium discoideum*: DDB_0232139, KEGG/ENZYME: 2.6.1.2/*Trypanosoma brucei*: Tb927.1.3950, KEGG/ ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi: 506529.430, KEGG/ENZYME: 2.6.1.2/ Trypanosoma cruzi: 510889.120 or KEGG/ENZYME: 2.6.1.2/Trypanosoma cruzi: 510889.140) of the ALT derived from human or the like based on that DNA sequence or a part thereof, and isolate polypeptides functionally equivalent to the ALT derived from human or the like from that DNA.

Hybridization conditions for isolating a DNA encoding a polypeptide functionally equivalent to the ALT derived from human or the like can be appropriately selected by those skilled in the art. For example, low stringent hybridization conditions may be given. Low stringent hybridization conditions are, for example, 42° C., 2×SSC and 0.1% SDS, preferably 50° C., 2×SSC and 0.1% SDS. More preferably, high stringent conditions may be given. For example, high stringent conditions are 65° C., 2×SSC and 0.1% SDS. Under these conditions, as the hybridization temperature is lowered, not only DNAs with high homology but also DNAs with only low homology are obtained. Conversely, it is expected that only those DNAs with high homology are obtained as the hybridization temperature is elevated. However, not only the temperature but also a plurality of factors (such as salt concentrations) affect the stringency of hybridization. Those skilled in the art could appropriately select these factors to realize similar stringency.

The polypeptide encoded by a DNA isolated by these hybridization techniques may have 70% or more homology and usually has high homology with the ALT derived from human or the like in the amino acid sequence. The term "high homology" refers to usually 97% or more homology, preferably 98% or more homology, more preferably 99% or more homology. For determination of the homology of polypeptides, the algorithm described in Wilbur, W. J. and Lipman, D. J., Proc. Natl. Acad. Sci. USA (1983) 80, 726-730 may be followed.

The polypeptide may vary in amino acid sequence, molecular weight, isoelectric point, presence or absence of sugar chains, morphology, etc. depending on the cell or host that produce the polypeptide or the purification method that will be described later. However, as long as the resultant polypeptide has functions equivalent to the functions of the ALT derived from human or the like, a DNA encoding the polypeptide can be used in the present invention. For example, when the polypeptide of the present invention is expressed in a prokaryote (e.g., *Escherichia coli*), a methionine reside is added to the N-terminus of the initial amino acid sequence of the polypeptide. When the polypeptide is expressed in a eukaryote (e.g., a mammalian cell), the N-terminal signal sequence is removed. A DNA encoding such a polypeptide can be used in the present invention.

In the present invention, as a DNA encoding ALT, a DNA having the nucleotide sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa japonica* (Japanese rice): 4342210, KEGG/ENZYME: 2.6.1.2/*Oryza sativa japonica* (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*: 233.t00009, KEGG/ENZYME: 2.6.1.2/*Entamoeba histolytica*: 24.t00016, KEGG/ENZYME: 2.6.1.2/*Trypanosoma cruzi*: 506529.420, KEGG/ENZYME: 2.6.1.2/*Trypanosoma cruzi*: 506529.430, KEGG/ENZYME: 2.6.1.2/*Trypanosoma cruzi*: 510889.120 or KEGG/ENZYME: 2.6.1.2/*Trypanosoma cruzi*: 510889.140 may be used. Alternatively, a DNA which hybridizes to a DNA complementary to a DNA having the nucleotide sequence described above under stringent conditions and yet encodes a polypeptide having ALT activity, may be used.

The DNA encoding ALT can be used in the in vivo or in vitro production of a desired polypeptide as described above. Further, the DNA encoding ALT may be used in the creation of a cell which strongly expresses ALT. The DNA encoding ALT may take any form as long as it is capable of encoding ALT. That is, the DNA may be, for example, a cDNA synthesized from mRNA, a genomic DNA or a chemically synthesized DNA. It should be noted that, as long as the DNA is capable of encoding ALT, the DNA may have any nucleotide sequence based on the degeneracy of genetic codes.

The DNA encoding ALT may be prepared by methods known to those skilled in the art. For example, the DNA may be prepared by preparing a cDNA library from a cell expressing ALT and performing hybridization using a part of the DNA sequence of ALT (e.g., the DNA sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa japonica* (Japanese rice): 4342210, KEGG/ENZYME: 2.6.1.2/*Oryza sativa japonica* (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica*:

233.t00009, KEGG/ENZYME: 2.6.1.2/*Entamoeba histolytica:* 24.t00016, KEGG/ENZYME: 2.6.1.2/*Trypanosoma cruzi:* 506529.420, KEGG/ENZYME: 2.6.1.2/*Trypanosoma cruzi:* 506529.430, KEGG/ENZYME: 2.6.1.2/*Trypanosoma cruzi:* 510889.120 or KEGG/ENZYME: 2.6.1.2/*Trypanosoma cruzi:* 510889.140) as a probe. The cDNA library may be prepared, for example, by the method described in Sambrook, J. et al., Molecular Cloning, Cold Spring Harbor Laboratory Press (1989). Alternatively, a commercial cDNA library may be used. It is also possible to prepare the DNA encoding ALT by preparing RNA from a cell expressing ALT, synthesizing oligo DNA molecules based on the DNA sequence of ALT (e.g., the DNA sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640, KEGG/ENZYME: 2.6.1.2/*Caenorhabditis elegans* (nematode): C32F10.8, KEGG/ENZYME: 2.6.1.2/*Oryza sativa japonica* (Japanese rice): 4342210, KEGG/ENZYME: 2.6.1.2/*Oryza sativa japonica* (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica:* 233.t00009, KEGG/ENZYME: 2.6.1.2/*Entamoeba histolytica:* 24.t00016, KEGG/ENZYME: 2.6.1.2/*Trypanosoma cruzi:* 506529.420, KEGG/ENZYME: 2.6.1.2/*Trypanosoma cruzi:* 506529.430, KEGG/ENZYME: 2.6.1.2/*Trypanosoma cruzi:* 510889.120 or KEGG/ENZYME: 2.6.1.2/*Trypanosoma cruzi:* 510889.140), and performing PCR using the oligo DNA molecules as primers to thereby amplify a cDNA encoding ALT.

Further, by determining the nucleotide sequence of the resultant cDNA, it is possible to determine the translation region encoding ALT and to obtain the amino acid sequence of ALT. Further, by screening a genomic library using the resultant cDNA as a probe, it is possible to isolate a genomic DNA.

Specifically, the following procedures may be used. First, mRNA is isolated from cells, tissues or the like expressing ALT. For the isolation of mRNA, the total RNA is prepared by known methods, for example, the guanidine ultracentrifugation method (Chirgwin, J. M. et al., Biochemistry (1979) 18, 5294-5299), the AGPC method (Chomczynski, P. and Sacchi, N., Anal. Biochem. (1987) 162, 156-159) or the like, and then mRNA is purified from the total RNA using mRNA Purification Kit (Pharmacia), etc. Alternatively, mRNA may be prepared directly using QuickPrep mRNA Purification Kit (Pharmacia).

From the resultant mRNA, cDNA is synthesized using a reverse transcriptase. Alternatively, cDNA may be synthesized using a kit such as AMV Reverse Transcriptase First-Strand cDNA Synthesis Kit (SEIKAGAKU CORPORATION). It is also possible to synthesize and amplify cDNA according to the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) using 5'-Ampli FINDER RACE Kit (Clontech) and polymerase chain reaction (PCR) with primers.

A DNA fragment of interest is prepared from the resultant PCR product and ligated to a vector DNA to thereby prepare a recombinant vector. The vector is introduced into a host (e.g., *E. coli*), followed by selection of resultant colonies to thereby obtain a desired recombinant vector. The nucleotide sequence of the DNA of interest may be confirmed by a known method such as the dideoxynucleotide chain termination method.

Further, a nucleotide sequence of higher expression efficiency can be designed for the DNA encoding ALT by considering the frequency of codon usage in the host to be used for expression (Grantham, R. et al., Nucleic Acids Research (1981) 9, p. 43-74). Further, the DNA encoding ALT can be modified using commercially available kits or known methods. Examples of such modifications include, but are not limited to, digestion with restriction enzymes, insertion of synthetic oligonucleotides or appropriate DNA fragments, addition of linkers, and insertion of an initiation codon (ATG) and/or a termination codon (TAA, TGA or TAG).

The DNA encoding ALT also includes a DNA which hybridizes to a DNA complementary to a DNA having the nucleotide sequence of KEGG/ENZYME: 2.6.1.2/*Homo sapiens* (human): 2875, KEGG/ENZYME: 2.6.1.2/*Homo sapiens* (human): 84706, KEGG/ENZYME: 2.6.1.2/*Mus musculus* (mouse): 76282, KEGG/ENZYME: 2.6.1.2/*Mus musculus* (mouse): 108682, KEGG/ENZYME: 2.6.1.2/*Rattus norvegicus* (rat): 81670, KEGG/ENZYME: 2.6.1.2/*Canis familiaris* (dog): 609510, KEGG/ENZYME: 2.6.1.2/*Xenopus laevis* (African clawed frog): 444533, KEGG/ENZYME: 2.6.1.2/*Drosophila melanogaster* (fruit fly): Dmel_CG1640. KEGG/ENZYME: 2.6.1.2/*Caenorhabditis elegans* (nematode): C32F10.8, KEGG/ENZYME: 2.6.1.2/*Oryza sativa japonica* (Japanese rice): 4342210, KEGG/ENZYME: 2.6.1.2/*Oryza sativa japonica* (Japanese rice): 4348524, KEGG/ENZYME: 2.6.1.2/*Cyanidioschyzon merolae*: CMM066C, KEGG/ENZYME: 2.6.1.2/*Saccharomyces cerevisiae*: YLR089c, KEGG/ENZYME: 2.6.1.2/*Saccharomyces cerevisiae*: YDR111c, KEGG/ENZYME: 2.6.1.2/*Ashbya gossypii* (*Eremothecium gossypii*): AGOS_AGR085W, KEGG/ENZYME: 2.6.1.2/*Candida albicans*: CaO19_346, KEGG/ENZYME: 2.6.1.2/*Schizosaccharomyces pombe*: SPBC582.08, KEGG/ENZYME: 2.6.1.2/*Aspergillus nidulans*: AN1923.2, KEGG/ENZYME: 2.6.1.2/*Aspergillus fumigatus*: AFUA_6G07770, KEGG/ENZYME: 2.6.1.2/*Aspergillus oryzae*: AO090003000164, KEGG/ENZYME: 2.6.1.2/*Cryptococcus neoformans* JEC21: CNG01490, KEGG/ENZYME: 2.6.1.2/*Dictyostelium discoideum*: DDB_0232139, KEGG/ENZYME: 2.6.1.2/*Trypanosoma brucei*: Tb927.1.3950, KEGG/ENZYME: 2.6.1.2/*Leishmania major*: LmjF12.0630, KEGG/ENZYME: 2.6.1.2/*Entamoeba histolytica:* 233.t00009, KEGG/ENZYME: 2.6.1.2/*Entamoeba histolytica:* 24.t00016, KEGG/ENZYME: 2.6.1.2/*Trypanosoma cruzi:* 506529.420, KEGG/ENZYME: 2.6.1.2/*Trypanosoma cruzi:* 506529.430, KEGG/ENZYME: 2.6.1.2/*Trypanosoma cruzi:* 510889.120 or KEGG/ENZYME:

2.6.1.2/*Trypanosoma cruzi*: 510889.140 under stringent conditions and encodes a polypeptide functionally equivalent to ALT.

Stringent conditions can be appropriately selected by those skilled in the art, including, for example, low stringent conditions. Low stringent conditions refer to, for example; 42° C., 2×SSC and 0.1% SDS, preferably 50° C., 2×SSC and 0.1% SDS. More preferably, high stringent conditions may be selected. High stringent conditions refer to, for example, 65° C., 2×SSC and 0.1% SDS. Under these conditions, as the hybridization temperature is elevated, DNAs with a higher homology can be obtained. The above-described DNA which hybridizes is preferably a DNA derived from nature, e.g., cDNA or chromosomal DNA.

These DNAs isolated by hybridization techniques usually have a high nucleotide sequence identity with a DNA encoding the ALT derived from human or the like. The DNA encoding ALT also includes a DNA which encodes a polypeptide functionally equivalent to the ALT derived from human or the like and has high identity with a DNA encoding the ALT derived from human or the like. The term "high identity" refers to usually 96% or more homology, preferably 98% or more homology, more preferably 99% or more identity. The identity of nucleotide sequences may be determined by algorithm BLAST (Karlin and Altschul, Proc. Natl. Acad. Sci. USA 90:5873-5877, 1993). Based on this algorithm, programs such as BLASTN and BLASTX have been developed (Altschul et al. J. Mol. Biol. 215:403-410, 1990). When nucleotide sequences are analyzed by BLASTN based on BLAST, parameters may be set as score=100 and wordlength=12, for example. Specific procedures for these analysis methods are known (ncbi.nlm.nih.gov.).

Production of a desired polypeptide may be performed by transferring a gene encoding the desired polypeptide into a cell which strongly expresses a bicarbonate transporter and CSAD or ALT and culturing the resultant cell in a medium.

When a desired polypeptide is produced using a cell into which a bicarbonate transporter gene and a CSAD or ALT gene have been artificially transferred, the order of the transfer of a bicarbonate transporter gene, the transfer of a CSAD or gene and the transfer of a gene encoding a desired polypeptide is not particularly limited. A gene encoding a desired polypeptide may be transferred after the transfer of a bicarbonate transporter gene and a CSAD or ALT gene. Alternatively, a bicarbonate transporter gene and a CSAD or ALT gene may be transferred after the transfer of a gene encoding a desired polypeptide. It is also possible to transfer a bicarbonate transporter gene, a CSAD or ALT gene and a gene encoding a desired polypeptide simultaneously.

A bicarbonate transporter gene, a CSAD or ALT gene and a gene encoding a desired polypeptide may be transferred simultaneously in a single vector. Alternatively, they may be transferred separately using a plurality of vectors.

For culturing the cell which strongly expresses a bicarbonate transporter (and which may strongly express CSAD or ALT), media used in conventional cell culture (preferably, animal cell culture) may be used. These media usually contain amino acids, vitamins, lipid factors, energy sources, osmotic regulators, iron sources and pH regulators. The contents of these components are usually as follows: amino acids 0.05-1500 mg/L, vitamins 0.001-10 mg/L, lipid factors 0-200 mg/L, energy sources 1-20 g/L, osmotic regulators 0.1-10000 mg/L, iron sources 0.1-500 mg/L, pH regulators 1-10000 mg/L, trace metal elements 0.00001-200 mg/L, surfactants 0-5000 mg/L, growth cofactors 0.05-10000 μg/L and nucleosides 0.001-50 mg/L. However, the contents are not limited to these ranges and may be appropriately selected depending on the type of the cell to be cultured, the type of the desired polypeptide, and so on.

In addition to these components, trace metal elements, surfactants, growth cofactors, nucleosides, and the like may be added.

Specific examples of such components include amino acids, such as L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, preferably, L-alanine, L-arginine, L-asparagine, L-aspartic acid, L-cystine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine; vitamins, such as i-inositol, biotin, folic acid, lipoic acid, nicotinamide, nicotinic acid, p-aminobenzoic acid, calcium pantothenate, pyridoxal hydrochloride, pyridoxine hydrochloride, riboflavin, thiamine hydrochloride, vitamin $B_{12}$ and ascorbic acid, preferably, biotin, folic acid, lipoic acid, nicotinamide, calcium pantothenate, pyridoxal hydrochloride, riboflavin, thiamine hydrochloride, vitamin $B_{12}$ and ascorbic acid; lipid factors, such as choline chloride, choline tartrate, linoleic acid, oleic acid and cholesterol, preferably, choline chloride; energy sources, such as glucose, galactose, mannose, and fructose, preferably, glucose; osmotic regulators, such as sodium chloride, potassium chloride, and potassium nitrate, preferably, sodium chloride; iron sources, such as iron EDTA, ferric citrate, ferrous chloride, ferric chloride, ferrous sulfate, ferric sulfate, and ferric nitrate, preferably, ferric chloride, iron EDTA, and ferric citrate; and pH regulators, such as sodium hydrogencarbonate, calcium chloride, sodium dihydrogenphosphate, HEPES and MOPS, preferably, sodium hydrogencarbonate. Culture media containing any of these components may be given as examples.

Besides the above components, there may be added trace metal elements, such as copper sulfate, manganese sulfate, zinc sulfate, magnesium sulfate, nickel chloride, tin chloride, magnesium chloride and sodium subsilicate, preferably, copper sulfate, zinc sulfate and magnesium sulfate; surfactants, such as Tween 80 and Pluronic F68; growth cofactors, such as recombinant insulin, recombinant IGF-1, recombinant EGF, recombinant FGF, recombinant PDGF, recombinant TGF-α, ethanolamine hydrochloride, sodium selenite, retinoic acid and putrescine dihydrochloride, preferably, sodium selenite, ethanolamine hydrochloride, recombinant IGF-1 and putrescine dihydrochloride; and nucleosides, such as deoxyadenosine, deoxycytidine, deoxyguanosine, adenosine, cytidine, guanosine and uridine. In preferable examples of above media, antibiotics, such as streptomycin, penicillin-G potassium and gentamicin, and pH-indicators, such as Phenol Red, may be contained.

The pH of the medium varies depending on the cell to be cultured. Generally, pH 6.8-7.6 is appropriate. In many cases, pH 7.0-7.4 is appropriate.

It is also possible to use a commercial medium for animal cell culture, e.g., D-MEM (Dulbecco's Modified Eagle Medium), D-MEM/F-12 1:1 Mixture (Dulbecco's Modified Eagle Medium Nutrient Mixture F-12), RPMI1640, CHO-S-SFMII (Invitrogen), CHO-SF (Sigma-Aldrich), EX-CELL 301 (JRH Biosciences), CD-CHO (Invitrogen), IS CHO-V (Irvine Scientific), PF-ACF-CHO (Sigma-Aldrich) or the like.

Alternatively, the medium may be a serum-free medium.

When the cell which strongly expresses a bicarbonate transporter (and which may strongly express CSAD or ALT) is CHO cells, CHO cells may be cultured by methods known to those skilled in the art. For example, CHO cells may be cultured usually in an atmosphere with a $CO_2$ concentration in the gas phase of 0 to 40%, preferably 2 to 10%, at 30 to 39° C., preferably about 37° C.

An appropriate culture period for producing a desired polypeptide using the cell which strongly expresses a bicarbonate transporter (and which may strongly express CSAD or ALT) is usually 1 day to 3 months, preferably 1 day to 2 months, more preferably 1 day to 1 month.

With respect to various culture devices for animal cell culture, a fermentor type tank culture device, an air lift type culture device, a culture flask type culture device, a spinner flask type culture device, a microcarrier type culture device, a fluidized bed type culture device, a hollow fiber type culture device, a roller bottle type culture device, a packed bed type culture device, or the like may be used.

Culture may be performed by any culture method such as batch culture, fed-batch culture or continuous culture. Preferably, fed-batch culture or continuous culture is used. Fed-batch culture is more preferred.

When the polypeptide produced according to the method of the present invention has a biological activity useful as a pharmaceutical, it is possible to produce a pharmaceutical by mixing this polypeptide with pharmaceutically acceptable carriers or additives and formulating into a preparation.

Specific examples of pharmaceutically acceptable carriers and additives include water, organic solvents that are pharmaceutically acceptable, collagen, polyvinyl alcohol, polyvinylpyrrolidone, carboxyvinyl polymer, carboxymethylcellulose sodium, sodium polyacrylate, sodium alginate, water-soluble dextran, carboxymethyl starch sodium, pectin, methylcellulose, ethyl cellulose, xanthan gum, gum Arabic, casein, agar-agar, polyethylene glycol, diglycerin, glycerin, propylene glycol, petrolatum, paraffin, stearyl alcohol, stearic acid, human serum albumin (HSA), mannitol, sorbitol, lactose, and surfactants that are acceptable as pharmaceutical additives.

Actual additives may be selected from the above-mentioned additives singly or in combination according to the dosage form of the therapeutic of the present invention, but are not limited to those listed above. For example, when a polypeptide is used in an injectable formulation, the purified polypeptide may be dissolved in a solvent such as physiological saline, buffer or a glucose solution, and then an adsorption inhibitor such as Tween 80, Tween 20, gelatin or human serum albumin may be added to the solution. Alternatively, a freeze-dried agent may be used to prepare a dosage form which is dissolved and reconstituted prior to use. Examples of the excipient useful for freeze-drying include sugar alcohols and saccharides such as mannitol and glucose.

Effective doses of the polypeptide may be appropriately selected depending on the type of the polypeptide, the type of the disease to be treated or prevented, the age of the patient, the severity of the disease, etc. For example, when the polypeptide is anti-glypican antibody, the effective dose of anti-glypican antibody is selected within a range of 0.001 mg to 1000 mg per kg of body weight per administration. Alternatively, a dose of 0.01-100000 mg/body may be selected per patient. However, effective dose is not limited to these ranges.

The polypeptide may be administered either orally or parenterally, but parenteral administration is preferred. Specifically, injection (e.g., systemic or local administration by intravenous injection, intramuscular injection, intraperitoneal injection, subcutaneous injection, etc:), transnasal administration, transpulmonary administration, transdermal administration and the like may be enumerated.

The present invention provides a cell which has a transferred DNA encoding a bicarbonate transporter and a transferred DNA encoding cysteine sulfinic acid decarboxylase or alanine aminotransferase, both of either of which may be incorporated into a vector.

When eukaryotes are used, animal cells, plant cells, fungal cells, etc. may be used as the host. Specific examples of animal cells include mammalian cells, such as CHO cells (J. Exp. Med. (1995) 108, 945), COS cells, 3T3 cells, myeloma cells, BIM (baby hamster kidney) cells, HeLa cells and Vero cells; amphibian cells, such as oocytes of *Xenopus laevis* (Valle, et al., Nature (1981) 291, 358-340); or insect cells, such as sf9, sf21 and Tn5 cells. Among CHO cells, dhfr-CHO lacking DHFR gene (Proc. Natl. Acad. Sci. USA (1980) 77, 4216-4420) and CHO K-1 (Proc. Natl. Acad. Sci. USA (1968) 60, 1275) are used with particular advantage. When high expression is intended in an animal cell, CHO cells are especially preferred. Introduction of the DNA which may be incorporated into a vector into the host cell may be performed by such methods as the calcium phosphate method, the DEAE dextran method, a method using a cationic ribosome DOTAP (Boehringer-Mannheim), electroporation, lipofection, etc.

As plant cells for polypeptide production, a *Nicotiana tabacum*-derived cell is known as a polypeptide production system and this may be subjected to callus culture. As fungal cells for polypeptide production, specific examples include yeast belonging to the genus *Saccharomyces*, e.g., *Saccharomyces cerevisiae*, and filamentous fungi belonging to the genus *Aspergillus*, e.g., *Aspergillus niger*.

When prokaryotes are used, production systems using bacterial cells are known. Specific examples of such bacterial cells include *E. coli* (such as JM109, DH5α, HB101) and *Bacillus subtilis*.

The polypeptide encoded by a gene of interest may be obtained by transforming these cells with the gene of interest and culturing the transformed cells in vitro. The culture may be performed by known methods. For example, as a culture broth for animal cells, a medium such as DMEM, MEM, RPMI1640 or IMDM may be used. A serum supplement such as fetal calf serum (FCS) may be used jointly. Alternatively, serum-free culture may be performed. The pH during culture is preferably about 6 to 8. The culture is usually performed at about 30-40° C. for about 15-200 hours. If necessary, replacement of the medium, aeration and agitation are carried out.

On the other hand, in vivo production systems include those using animals or plants. A gene of interest is transferred into these animals or plants to produce the polypeptide in the animal bodies or plant bodies. Then, the polypeptide is collected. The term "host" as used herein includes such animals or plants.

When animals are used, available production systems include those using mammals or insects. Goat, pig, sheep, mouse and cattle may be used as mammals (Vicki Glaser, SPECTRUM Biotechnology Applications, 1993). When mammals are used, transgenic animals may be used.

First, a gene of interest is fused to a gene encoding a polypeptide produced inherently in milk (such as goat (β-casein) to thereby prepare a fusion gene. A DNA fragment containing this fusion gene is injected into a goat embryo, which is then implanted in the uterus of a female goat. The polypeptide of interest can be obtained from the milk produced by transgenic goats born from the goat which accepted the embryo or the offspring of the transgenic goats. In order to increase the yield of milk containing the polypeptide produced by the transgenic goats, hormones may be appropriately administered to the transgenic goats (Ebert, K. M. et al., Bio/Technology (1994) 12, 699-702).

Examples of insects which may be used include silkworm. In this case, silkworm is infected with baculovirus carrying a transferred gene encoding the polypeptide of interest. The polypeptide of interest can be obtained from the body fluid of the silkworm (Susumu, M. et al., Nature (1985) 315, 592-594).

Furthermore, when plants are used, tobacco can typically be used. When tobacco is used, a gene encoding the polypeptide of interest is inserted into a plant expression vector (e.g., pMON 530), which is then transferred into a bacterium such as *Agrobacterium tumefaciens*. A tobacco plant (e.g., *Nicotiana tabacum*) is infected with the resultant bacterium. The polypeptide of interest can be obtained from leaves of this plant (Julian, K.-C. Ma et al., Eur. J. Immunol. (1994) 24, 131-138).

The polypeptide thus obtained can be isolated from the inside of the host cell or from its outside (e.g., medium), and purified to a substantially pure and homogeneous polypeptide. Isolation and purification of polypeptides can be performed using conventional isolation and purification methods for polypeptides, and are not limited in any way. For example, polypeptides can be isolated and purified by appropriate selection and combination of various tools and techniques, such as chromatography columns, filters, ultrafiltration, salting-out, precipitation with solvent, extraction with solvent, distillation, immunoprecipitation, SDS-polyacrylamide gel electrophoresis, isoelectric focusing, dialysis, recrystallization, etc.

Examples of chromatography include affinity chromatography, ion exchange chromatography, hydrophobic chromatography, gel filtration, reverse-phase chromatography, adsorption chromatography, etc. (Strategies for Protein Purification and Characterization: A Laboratory Course Manual. Ed. Daniel R. Marshak et al., Cold Spring Harbor Laboratory Press, 1996). These chromatographic techniques can be carried out using liquid phase chromatography, for example, HPLC, FPLC, etc. The present invention also includes those polypeptides highly purified using these purification methods.

Before or after the purification, it is also possible to give optional modifications to the polypeptide or remove a partial peptide therefrom by reacting the polypeptide with an appropriate polypeptide modification enzyme. Examples of such enzyme include, but are not limited to, trypsin, chymotrypsin, lysyl endopeptidase, protein kinase and glucosidase.

In the present invention, the concept of "cells into which DNA has been transferred" encompasses not only cells into which exogenous DNA has been incorporated by genetic recombination technology; but also cells in which endogenous DNA has been activated by gene activation technology (see, for example, International Publication WO94/12650) so that expression of a protein corresponding to the endogenous DNA or transcription of the DNA has been initiated or increased.

EXAMPLES

Hereinbelow, the present invention will be described in more detail with reference to the following Examples. It should be noted that these Examples are provided only for illustrating the present invention and not for limiting the scope of the present invention.

Example 1

Figure 1:
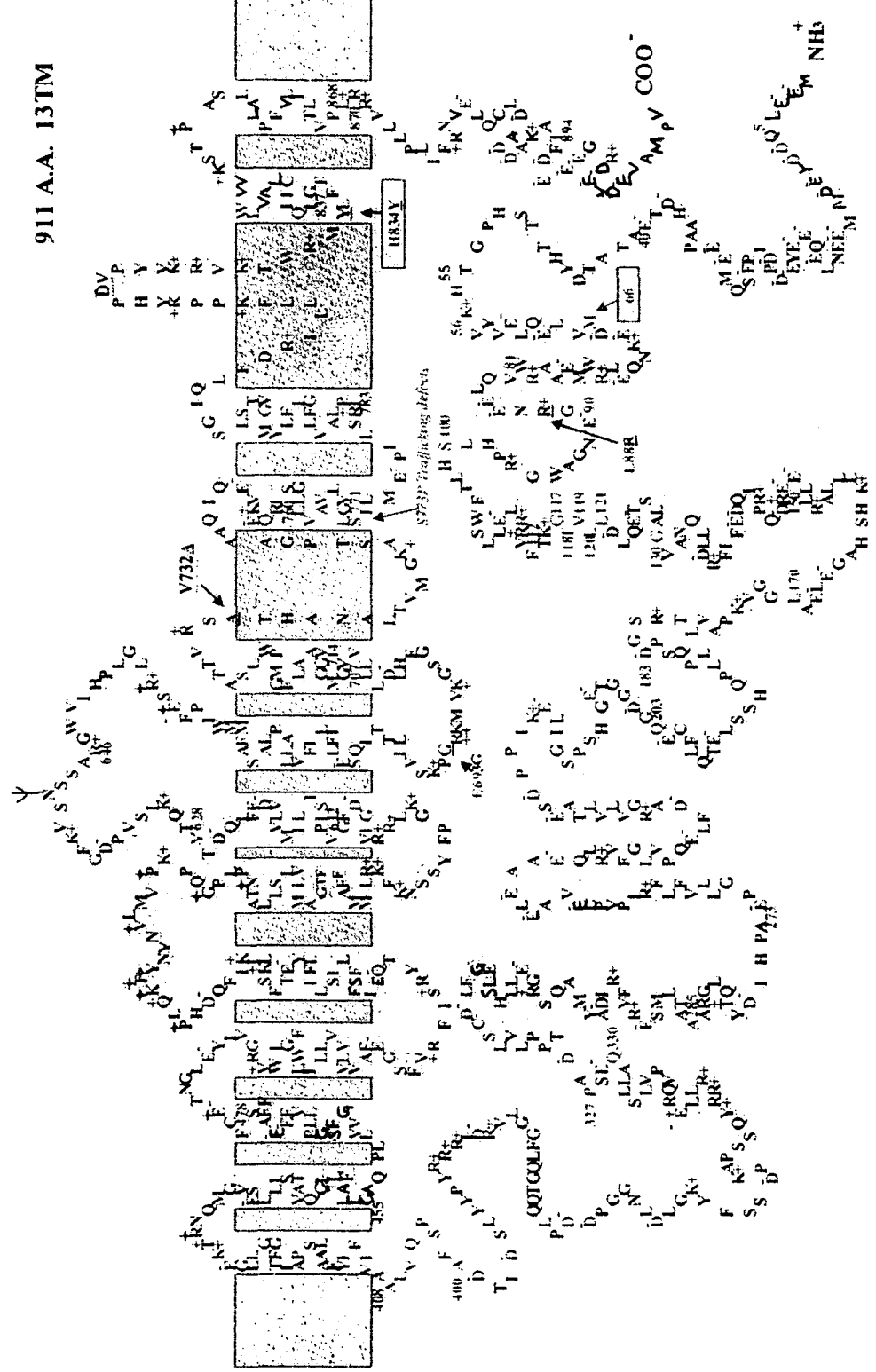
FIG. 1 shows an AE1 membrane topology produced based on a transmembrane domain and direction predicted from an amino acid sequence of human hepatic cell-derived AE1 as obtained by TMpred program with reference to FIG. 1 in Exo Physiol 91.1 pp. 153-161, 2006, Seth L. Alper (SEQ ID NO: 11).

Cloning of a Human Hepatic Cell Anion Exchanger (Anion Exchanger 1, Band 3) Gene Using a commercial Human Liver QUICK-Clone cDNA (Clontech Laboratories, Inc.) as a template, an Anion Exchanger (AE1) gene derived from a human liver was obtained by a PCR method. The gene thus cloned was sequenced to confirm that it encoded AE1 in view of its homology with a published human AE1. The AE1 gene thus obtained had mutations at eight sites in the sequence of 2733 bases (t263g, t357c, a645t, a672c, c951t, a2078g, t2195c, c2500t) and coded for 911 amino acids including four different amino acids (L88R, E693G, V732A, H834Y). However, because a product obtained by the gene was predicted to be a transporter having 13 transmembrane domains (FIG. 1), the gene was used for cell modulation as an AE1 gene derived from a human liver.

Example 2

Figure 2:
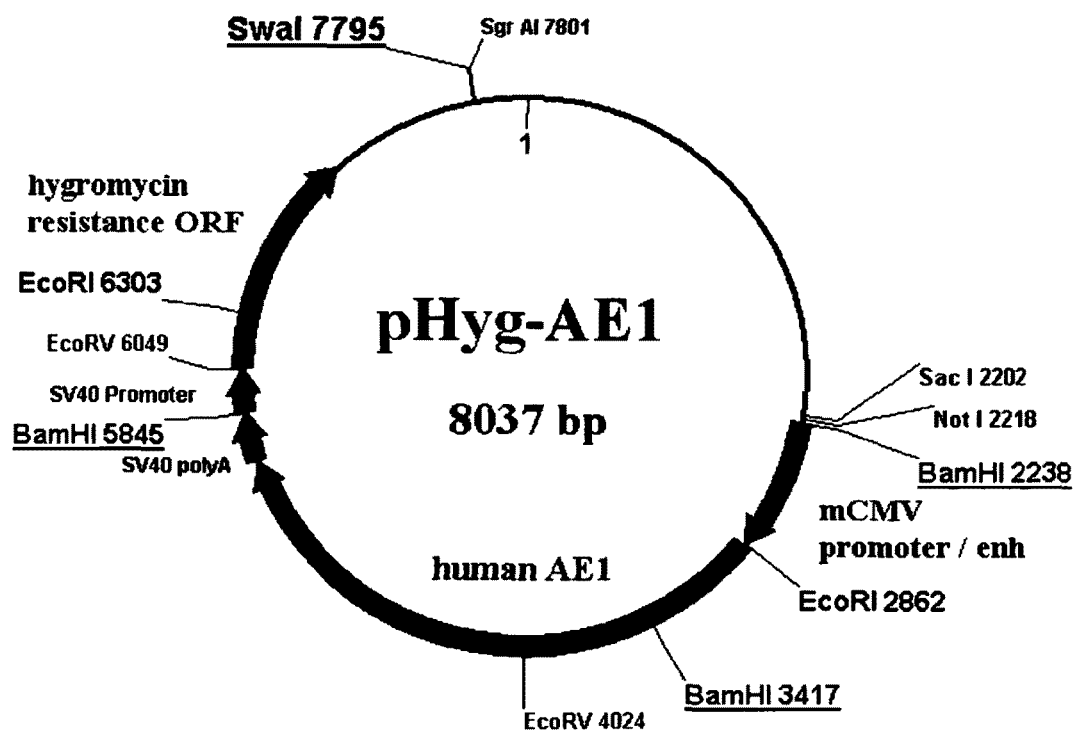
FIG. 2 shows a plasmid for Hygromycin-selection, in which human AE1 (911 amino acids) has been expressed.
Figure 3:
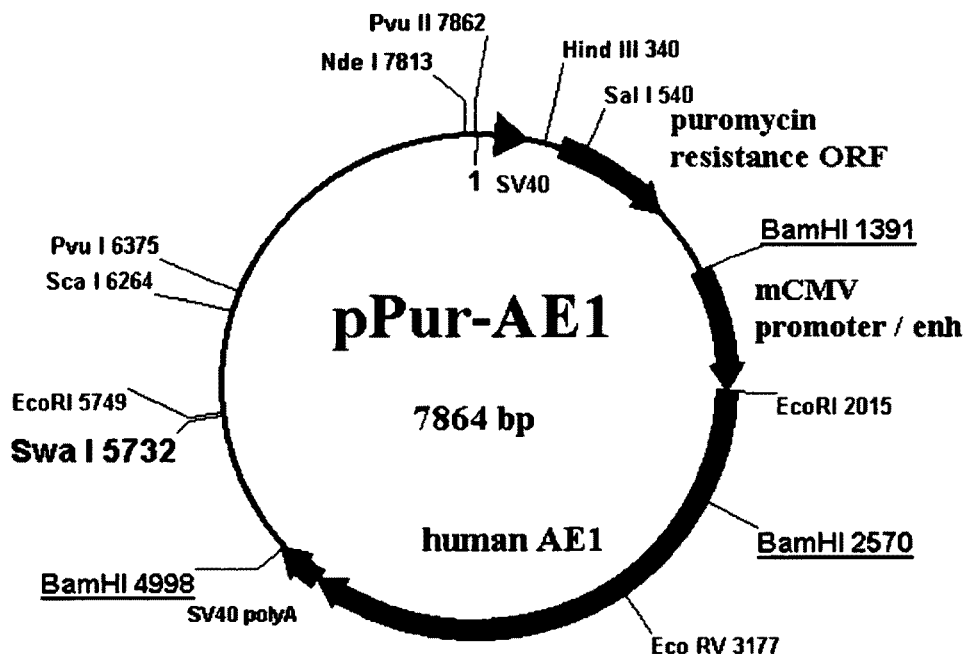
FIG. 3 shows a plasmid for Puromycin-selection, in which human AE1 (911 amino acids) has been expressed.
Figure 4:
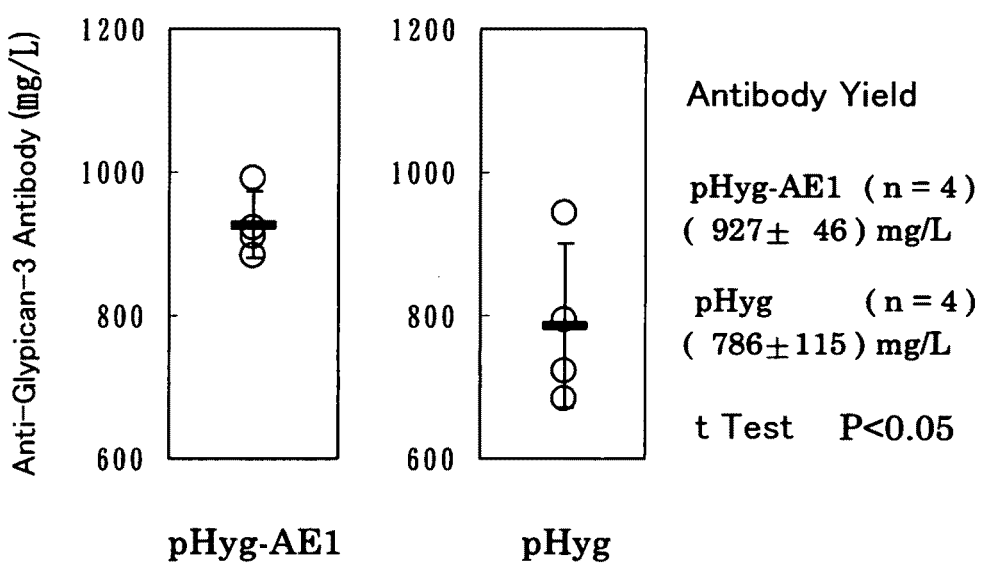
FIG. 4 is a plot of the amount of anti-glypican-3 antibody production on day 12 of fed-batch culture in a 50-mL shaker flask. The amount of an anti-glypican-3 antibody produced by pHyg-AE1-transformed cells (n=4) was significantly greater than that produced by pHyg-transformed cells (n=4) (P<0.05).

Increase in the Amount of Antibody Production by Introduction of a Human Anion Exchanger Gene By adding a Kozak sequence to the human AE1 gene obtained by PCR cloning in Example 1 (which is hereinafter called AE1), pHyg-AE1 (FIG. 2) and pPur-AE1 (FIG. 3) were constructed as CMV promoter expression plasmids. The pHyg-AE1 or pHyg expression plasmids that did not contain the AE1 gene (which was obtained by first introducing Hygromycin-resistance gene expression units derived from pTK5 provided by Clontech Laboratories, Inc. into pSV2-dhfr plasmids (ATCC No. 37146) and then removing the dhfr expression units from the constructed plasmids) were introduced into anti-glypican-3 antibody-producing CHO cells as a parent strain (see International Publication WO 2006/006693) by electroporation. Then, strains that exhibited high proliferation in static culture in the presence of Hygromycin (200 µg/ml) were selected. After amplification, a total RNA was prepared from the pHyg-AE1 strains, and five strains expressing human AE1 at high levels were selected by a TaqMan method. Further, a comparison was made for the amount of antibody production between pHyg-transformed cells as a control (four strains) and four strains of human AE1-transformed cells that proliferated at a level equivalent to that observed with control during shake culture. During fed-batch culture in a 50-ml shaker flask under the condition of $2 \times 10^5$ cells/mL in an initial stage, the amount of an anti-glypican-3 antibody produced by pHyg-AE1-transformed cells (four strains) on day 12 after initiation of the shake culture was significantly greater than that produced by pHyg-transformed cells (four strains) (t-test: P<0.05, FIG. 4).

Figure 6:
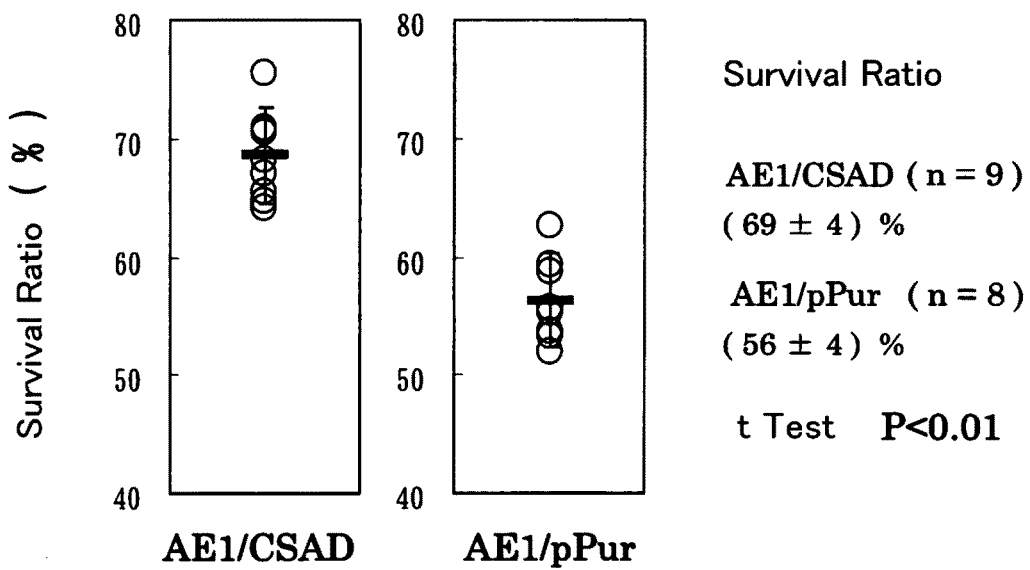
FIG. 6 is a plot of survival rates on day 10 of fed-batch culture in a 50-mL shaker flask. The survival rate of an AE1/CSAD co-expressing cell strain (n=9) which was obtained by introducing pPur-CSAD into a pHyg-AE1-42 strain, or a pHyg-AE1-transformed cell capable of high-yield antibody production, was significantly higher than that of AE1/pPur co-expressing cells (n=8) which were obtained by introducing pPur into a pHyg-AE1-42 strain (P<0.01).

Then, using as a parent strain the AE1 expressing strain that produced the largest amount of an antibody among the four pHyg-AE1-transformed strains, pPur-CSAD or a cysteine sulfinic acid decarboxylase (CSAD) expression plasmid containing a Puromycin-resistance gene (FIG. 10, see Referential Example 2 described later), pPur-ALT1 or an alanine aminotransferase (ALT1) expression plasmid containing Puromycin-resistance gene (FIG. 11, see Referential Example 4 described later), and a control plasmid pPur (pPUR, Puromycin resistance expression vector, provided by Clontech Laboratories, Inc.) were introduced by electroporation. Then, strains that exhibited high proliferation in static culture in the presence of Puromycin (6 µg/ml) were selected. After amplification, a total RNA was prepared from the strains thus selected. Then, AE1/CSAD co-expressing strains (nine strains), AE1/ALT1 co-expressing strains (10 strains), and AE1/pPur co-expressing strains (eight strains), which expressed the newly introduced genes at high levels, were selected and compared for the amount of antibody production and the survival rate. In fed-batch culture in 50-mL shaker flasks under the condition of $2\times10^5$ cells/mL in an initial stage, the AE1/CSAD co-expressing strains (nine strains) showed significantly greater amounts of anti-glypican-3 antibody production (t-test P<0.05, FIG. 5) and significantly higher survival rates (t-test P<0.01, FIG. 6) than the control AE1/pPur co-expressing strain (eight strains) on day 10 at the late stage of the shake culture. Among the three kinds of co-expressing strains, AE1/ALT1 co-expressing strains (10 strains) produced the largest amount of an anti-glypican-3 antibody, which was significantly greater than that produced by the control AE1/pPur co-expressing strains (eight strains) on day 8 of the shaker fed-batch culture (t-test P<0.01, FIG. 7). Subsequently, AA53, which produced the largest amount of an antibody (1497 mg/L/8 days) and expressed ALT1 mRNA at the highest level among the AE1/ALT1 co-expressing strains (10 strains) in the study using the shaker fed-batch culture, was subjected to fed-batch culture in a 1-L jar ($10\times 10^5$ cells/mL in an initial stage). Then, the amount of an antibody produced by AA53 on day 7 of the culture was found to be 1.9 g/L/7 days, revealing that AA53 was capable of high-yield antibody production in short-term culture (FIG. 8). Considering that TA41, which was a TauT/ALT1 co-expressing strain that produced 5.3 g/L of an antibody on day 21 of the culture (see Referential Example 4 described later), produced 1.5 g/L of an antibody on day 7 of the culture, AA53 has a potential to produce a greater amount of an antibody in a short time than does TA41, and hence, AA53 is considered to be suitable for practical production.

The above results show that cells capable of high-yield antibody production can be obtained by strongly expressing an anion exchanger (AE) artificially, and by strongly expressing AE1 and CSAD or ALT1 simultaneously.

Also, the effect of strongly expressing AE1 was shown by construction of a strain capable of producing an anti-IL-6R antibody using an AE1 strongly expressing host cell. Into an ordinary host cell DXB11, pHyg-AE1 (FIG. 2) was introduced by electroporation. Then, strains that exhibited high proliferation in static culture in the presence of Hygromycin (200 µg/ml) were selected. After amplification, cells expressing human AE1 at high levels were established as an AE1/DXB11 host cell by a TaqMan method. Anti IL-6R antibody expression plasmids were introduced into the AE1/DXB11 host cells, and AE1-S08 was obtained by single cell cloning. AE1-S08 thus obtained was capable of high-yield production of an anti-IL-6R antibody, and the amount of its production on day 14 of fed-batch culture in a 1 L-jar ($7\times10^5$ cells/mL in an initial stage) was 3.0 g/L as shown in FIG. 12. It has been confirmed that AE1-S08 capable of high-yield antibody production and the host cells, AE1/DXB11, were both stable in a stability test performed by subculturing and maintained AE1 expression at high levels.

The above results suggest that the effect of introduction of an AE1 gene acts positively both before and after introduction of an antibody gene.

The present invention can be applied to all types of cells capable of producing a polypeptide (preferably an antibody).

Referential Example 1

Cloning of CHO Cell-Derived Hamster Cysteine Sulfinic Acid Decarboxylase (CSAD) and Cysteine Dioxygenase, type I (CDO1) Genes Total RNA was extracted from anti-IL-6 receptor antibody-producing cells (A CHO DMB11 cell line into which an anti-IL-6 receptor antibody gene had been transferred) (Japanese Unexamined Patent Publication No. Hei 8-99902), and then cDNA was synthesized therefrom in a poly(A) dependent manner. Hamster CSAD and CDO1 genes were obtained by PCR using as a template the cDNA fragmented with three restriction enzymes, SalI, XhoI and EcoRI. As PCR primers, those containing the 5'-end and the 3'-end sequence conserved between rat and mouse CSADs or CDO1s were designed. The nucleotide sequences of the cloned genes were determined. From its homology with other CSAD or CDO1 genes of known species, the cloned gene was confirmed to encode hamster CASD (FIG. 9). The amino acid sequence of hamster CSAD has high homology with the known amino acid sequences of mouse CSAD (96% identity), rat CSAD (96% identity) and human CSAD (91% identity); it was predicted that hamster CSAD is an enzyme having the same activity. The nucleotide sequence of hamster CSAD is shown in SEQ ID NO: 3. The amino acid sequence of hamster CSAD is shown in SEQ ID NO: 4.

Referential Example 2

Construction of a Hamster CSAD Expressing Plasmid for Puromycin-Selection

By adding a Kozak sequence to the hamster CSAD (which is hereinafter called CSAD) gene obtained by PCR cloning in Referential Example 1, a CMV promoter expression plasmid pPur/CSAD (FIG. 10) was constructed.

Referential Example 3

Cloning of Human Hepatic Cell Alanine Aminotransferase Gene

Using a commercial Human Liver QUICK-Clone cDNA (Clontech Laboratories, Inc.) as a template, alanine aminotransferase (ALT1) gene derived from a human liver was obtained by a PCR method. The gene thus cloned was sequenced and confirmed to encode ALT1 based on its homology with published human ALT1. The ALT1 gene thus obtained had mutations at five sites in the sequence of 1488 bases (c157a, a215g, c765t, t857c, t995a) and coded for 496 amino acids including four different amino acids (R53S, Q72R, F286S, M332K), but this was used as a PCR clone of the human liver derived ALT1 for cell modulation.

Referential Example 4

Increase in Antibody Yield by Transfer of Human Alanine Aminotransferase

By adding a Kozak sequence to the human ALT1 obtained by cloning in Referential Example 3 (which is hereinafter called ALT1), pPur-ALT1, which was a CMV promoter expression plasmid, was constructed (FIG. 11). The pPur-ALT1 or pPur expression plasmids that did not contain the ALT1 gene were introduced into anti-glypican-3 antibody-producing CHO cells as parent strains (see International Publication WO 2006/006693) by electroporation, and cell strains that exhibited high proliferation in static culture in the presence of Puromycin (6 µg/ml) (pPur-ALT1: seven strains, pPur: three strains) were selected. After expansion, a total RNA was prepared from the pPur-ALT1 cell strains, and six strains expressing human ALT1 at high levels were selected by a TaqMan method. Further, a comparison was made for the antibody yield between pPur-transferred cells as a control (three strains) and four strains of human ALT1-transferred cells that proliferated at a level equivalent to that observed with the pPur-transferred cells during the shake culture. During fed-batch culture in a 50 ml shaker flask with an initial cell density of $2 \times 10^5$ cells/mL, the anti-glypican-3 antibody yield of pPur-ALT1-transferred cells (four strains, 1236±149 mg/L) on day 17 at the late stage of the shaker culture was significantly higher than that of pPur-transferred cells (three strains, 871±119 mg/L) (t-test: p<0.01). A72, a pPur-ALT1 expressing strain, and P41, a pPur expressing strain, were each found to have produced the largest amount of an antibody in the study using shaker fed-batch culture, and they were subjected to fed-batch culture in 1 L jars (an initial cell density of $10 \times 10^5$ cells/mL). As a result, the antibody yield of A72 was 2.9 g/L on day 19 of the culture, which was greater than the antibody yield of P41 (2.2 g/L). Since no increase was observed in the antibody yield of P41 on day 14 or subsequent days after the initiation of the culture, the high-yield production of an antibody by A72 was considered to be attributable to the survival ratio maintaining effect (The survival rates of pPur-ALT1 expressing strain A72 and pPur expressing strain P41 were 60% and 23%, respectively, on day 14 of the culture).

Then, pPur-ALT1 or pPur was co-transferred into T10 which was a pHyg-TauT-transferred cell used as a parent strain (see Referential Example 6 described later). TauT/ALT1 co-expressing cells that exhibited high proliferation and expressed human ALT1 at high level (six strains) and TauT/pPur co-expressing cells that exhibited high proliferation (eight strains) were selected and subjected to fed-batch culture in 50 mL shaker flasks (an initial cell density of $10 \times 10^5$ cells/mL). The anti-glypican-3 antibody yield (745±87 mg/L) of TauT/ALT1 co-expressing cells, which were ALT expressing cells, on day 4 of the shaker culture was significantly higher than that of TauT/pPur cells (616±29 mg/L) (t-test: p<0.01).

TA41, which was a TauT/ALT1 co-expressing strain that produced the largest amount of an antibody (881 mg/L/4 days) and expressed ALT1 mRNA at the highest level in the study using the shaker fed-batch culture, was subjected to fed-batch culture in a 1 L jar (an initial cell density of $10 \times 10^5$ cells/mL). The antibody yields were as high as 1.3 g/L on day 7 of the culture, 3.0 g/L on day 10 of the culture, 3.5 g/L on day 12 of the culture, 4.6 g/L on day 17 of the culture, and 5.3 g/L on day 21 of the culture, which were clearly higher than the values for TP08 (656 mg/L/4 days), which was a control strain that produced the largest amount of an antibody among the TauT/pPur co-expressing strains (2.4 g/L on day 10 of the culture).

Referential Example 5

Cloning of CHO Cell-Derived Hamster Taurine Transporter Gene

Total RNA was extracted from anti-IL-6 receptor antibody-producing cells (A CHO DXB11 cell line into which an anti-IL-6 receptor antibody gene had been transferred) (Japanese Unexamined Patent Publication No. Hei 8-99902), and then cDNA was synthesized therefrom in a poly(A) dependent manner. Hamster taurine transporter (TauT) gene was obtained by PCR using as a template the cDNA fragmented with three restriction enzymes, SalI XhoI and EcoRI. As PCR primers, those containing the 5'-end and the 3'-end sequence conserved between rat and mouse TauTs were designed. The nucleotide sequence of the cloned gene was determined. From its homology with other TauT genes of known species, the cloned gene was confirmed to encode hamster TauT (FIG. 13). The amino acid sequence of hamster TauT has high homology with mouse TauT (96% identity), rat TauT (96% identity) and human TauT (93% identity); it was predicted that hamster TauT is a transporter with 12 transmembrane regions (FIG. 14).

Referential Example 6

Increase in Viable Cell Density, Inhibition of Lactate Production and Increase in Antibody Yield, as Caused by Transfer of Hamster Taurine Transporter CMV promoter expression plasmid pHyg/TauT was constructed (FIG. 15) by adding Kozak sequence to the hamster TauT (hereinafter, TauT) gene obtained by cloning in Referential Example 5. Control plasmid pHyg without pHyg/TauT or TauT gene was introduced by electroporation into the parent strain anti-glypican-3 antibody producing CHO cell (see WO 2006/006693). After selection of expression plasmid-transferred cells in the presence of hygromycin (400 µg/ml), all of the stably growing cell strains were expanded (pHyg/TauT: 8 strains; pHyg: 7 strains). TauT mRNA was prepared. Subsequently, 7 strains were confirmed to express TauT more strongly than the parent strain by the TaqMan method; they were selected as pHyg/TauT transferred cells. The mean mRNA expression level of these transferred cells (7 strains) was about 40 times larger than the control (7 strains). Cells of the total 14 strains were subjected to batch culture and fed-batch culture in 50 ml shaker flasks with an initial cell density of $2 \times 10^5$ cells/ml. On day 7 of culture (late-stage), viable cell densities, lactate yields and anti-glypican-3 antibody yields in those strains were compared. In batch culture, growth inhibitory substances such as lactate accumulate in culture broth as cells grow and their growth is inhibited. However, the viable cell densities ($9.28 \pm 3.27 \times 10^5$ cells/ml) and lactate yields (1.54±0.20 g/L) in pHyg/TauT transferred cells were superior to those in pHyg transferred cells (viable cell densities: $5.69 \pm 2.09 \times 10^5$ cells/ml, lactate yields: 1.54±0.20 g/L) (t test; p<0.05). With respect to anti-glypican-3 antibody yield, 4 out of the 7 strains of pHyg/TauT-transferred cell showed antibody yields (mean antibody yield: 440.6 mg/L) higher than the highest yield in pHyg-transferred cell (389.6 mg/L). Further, since superiority of pHyg/TauT transferred cells in anti-glypican-3 antibody yield became more evident (t test; P<0.01) in fed-batch culture, pHyg/TauT transferred T10 strain (which showed the highest growth ability among the above 4 strains) and the parent strain were subjected to fed-batch culture in 1 L jar. As a result, the viable ratio of T10 was maintained at 80% or more even on day 32 of culture, with inhibited lactate production. Consequently, its anti-glypican-3 antibody yield achieved 2.9 g/L on day 35 of culture. It was confirmed by flow cytometric analysis that TauT-transferred T10 cell was expressing TauT molecules on the cell membrane. These results suggest that by artificially expressing hamster Taut, it is possible to raise the potential of antibody-producing cells and create strains capable of enhanced antibody production.

All publications, patent and patent applications cited herein are incorporated herein by reference in their entirety.

INDUSTRIAL APPLICABILITY

The present invention is applicable to production of polypeptides.

SEQUENCE LISTING FREE TEXT

<SEQ ID NO: 1>
SEQ ID NO: 1 shows the nucleotide sequence of a gene encoding human AE1 (GenBank M27819).
<SEQ ID NO: 2>
SEQ ID NO: 2 shows the amino acid sequence of human AE1 (UniProtKB/Swiss-Prot P02730).
<SEQ ID NO: 3>
SEQ ID NO: 3 shows the nucleotide sequence of a gene encoding hamster CSAD.
<SEQ ED NO: 4>
SEQ ID NO: 4 shows the amino acid sequence of hamster CSAD.
<SEQ ID NO: 5>
SEQ ID NO: 5 shows the nucleotide sequence of a gene encoding human ALT1 (KEGG/ENZYME: 2.6.1.2/*Homo sapiens* (human): 2875)<
<SEQ ID NO: 6>
SEQ ID NO: 6 shows the amino acid sequence of human ALT1 (KEGG/ENZYME: 2.6.1.2/*Homo sapiens* (human): 2875).
<SEQ ID NO: 7>
SEQ ID NO: 7 shows the nucleotide sequence of a gene encoding hamster taurine transporter.
<SEQ ID NO: 8>
SEQ ID NO: 8 shows the amino acid sequence of hamster taurine transporter.

The invention claimed is:

1. A method of producing an antibody comprising culturing an isolated mammalian cell which is transfected with a heterologous DNA encoding a bicarbonate transporter and is transfected with a heterologous DNA encoding a desired antibody and allowing the cell to produce said antibody,
wherein the bicarbonate transporter exchanges Cl⁻ outside of a plasma membrane for $HCO_3^-$ inside a plasma membrane, and wherein the bicarbonate transporter is anion exchanger 1 (AE1), anion exchanger 2 (AE2), or anion exchanger 3 (AE3).

2. The method of claim 1, wherein the cell is further transfected with a DNA encoding a cysteine sulfinic acid decarboxylase or alanine aminotransferase.

3. The method of claim 1, wherein the bicarbonate transporter is anion exchanger 1 (AE1).

4. The method of claim 1, wherein the cell is a Chinese hamster ovary cell.

5. The method of claim 1, wherein the anion exchanger 1 (AE1) is encoded by a DNA of any one of the following (a) to (d):
(a) a DNA encoding a polypeptide having the amino acid sequence as shown in SEQ ID NO: 2;
(b) a DNA encoding a polypeptide which has an amino acid sequence derived from the amino acid sequence as shown in SEQ ID NO: 2 by substitution, deletion, addition and/or insertion of no more than one to ten amino acid residues;
(c) a DNA encoding a polypeptide having 96% or more amino acid sequence homology with the amino acid sequence as shown in SEQ ID NO: 2; and
(d) a DNA having the nucleotide sequence as shown in SEQ ID NO: 1.

6. An isolated mammalian cell which is transfected with a heterologous DNA encoding a bicarbonate transporter and is transfected with a heterologous DNA encoding a desired antibody,
wherein the bicarbonate transporter exchanges Cl⁻ outside of a plasma membrane for $HCO_3^-$ inside a plasma membrane, and wherein the bicarbonate transporter is anion exchanger 1 (AE1), anion exchanger 2 (AE2), or anion exchanger 3 (AE3).

7. The cell of claim 6, wherein the cell is further transfected with a DNA encoding a cysteine sulfinic acid decarboxylase or alanine aminotransferase.

* * * * *